United States Patent [19]
Sanghvi et al.

[11] Patent Number: 5,808,023
[45] Date of Patent: Sep. 15, 1998

[54] MODIFIED OLIGONUCLEOTIDES

[75] Inventors: Yogesh S. Sanghvi; Phillip Dan Cook, both of Carlsbad, Calif.

[73] Assignee: ISIS Pharmaceuticals, Inc., Carlsbad, Calif.

[21] Appl. No.: 335,046

[22] Filed: Nov. 7, 1994

Related U.S. Application Data

[60] Division of Ser. No. 40,903, Mar. 31, 1993, Pat. No. 5,386,023, which is a continuation-in-part of Ser. No. PCT/US92/04294 May 21, 1992 and a continuation-in-part of Ser. No. 903,160, Jun. 24, 1992, abandoned, which is a continuation-in-part of Ser. No. 703,619, May 21, 1991, Pat. No. 5,378,825, which is a continuation-in-part of Ser. No. 566,836, Aug. 13, 1990, Pat. No. 5,223,618, and a continuation-in-part of Ser. No. 558,663, Jul. 27, 1990, Pat. No. 5,138,045.

[51] Int. Cl.$^6$ .................................................. C07H 21/00
[52] U.S. Cl. .................... 536/23.1; 536/25.3; 536/25.32; 536/25.33; 536/25.34; 536/25.6
[58] Field of Search ............................... 536/25.34, 25.6, 536/27.14, 28.2, 4.1, 25.3, 25.33, 26.26, 26.7, 26.8

[56] References Cited

U.S. PATENT DOCUMENTS

| | | |
|---|---|---|
| Re. 33,887 | 4/1992 | Tam et al. . |
| 3,687,808 | 8/1972 | Merigan et al. . |
| 4,511,713 | 4/1985 | Miller et al. . |
| 4,707,440 | 11/1987 | Stavrianopoulos . |
| 5,378,825 | 1/1995 | Cook et al. . |
| 5,386,023 | 1/1995 | Sanghvi et al. . |
| 5,466,786 | 11/1995 | Buhr et al. . |
| 5,541,307 | 7/1996 | Cook et al. . |

FOREIGN PATENT DOCUMENTS

| | | |
|---|---|---|
| 0 269 574 A2 | 6/1988 | European Pat. Off. . |
| US91/05720 | 3/1992 | WIPO . |
| WO 93/18052 | 9/1993 | WIPO . |

OTHER PUBLICATIONS

Comprehensive Organic Synthesis: Ed. by B.M. Trost & J. Fleming, vol. 4, p. 760.
Curran, Radical Addition Reactions, In Comprehensive Organic Synthesis: Trost, B.M. and Fleming, I., Eds. vol. 4, 715–832 Pergamon Press, Oxford (1991).
Egholm M. "Peptide nucleic acids (PNA). Oligonucleotide analogues with an achiral peptide backbone", *J. Am. Chem. Soc.* 1992, 114, 1895–1897.
Egholm et al., "Recognition of Guanine and Adenine in DNA by Cytosine and Thymine Containing Peptide Nucleic Acids (PNA)[1,2]" J. Am. Chem. Soc. 114: 9677–9678 (1992).
Giannis, A. et al., "Fragmentation and wittig olefination of glucosamine derivatives–a simple routine to open chain amino sugars and chiral glycerols", *Tetrahedron Letters* 1988, 44(23), 7177–7180.
Greene and Wuts in *Protective Groups in Organic Synthesis*, John Wiley and Sons, Inc. 1991 175–223.
Hart et al., "Bis (Trimethylstannyl) Benzopinacolate–mediated" J. Am. chem. Soc. 110: 1631–1633 (1988).
Yamamoto, I, Sekine and Hata, "One–step synthesis of 5'–azido–nucleosides", *J.C.S. Perkin* 1980, I, 306–310.
Hyrup et al., "Modification of the Binding Affinity of Peptide Nucleic Acids (PNA). PNA with Extended Backbones Consisting of 2–Aminoethyl–β–alanine or 3–Aminopropylglycine Units" *J. Chem. Soc. Chem. Commun.* 1993, 518–519.
Inouye et al., "Selective Coloration of Spiro Pyridopyrans for Guanosine Derivatives," *J. Am. Chem. Soc.*, 114:778–780, 1992.
Prakash, G. and Kool, E.t., "Molecular recognition by circular oligonucleotides. Stong binding of single–stranded DNA and RNA", *J. Chem. Soc. Chem. Commun.* 1991, 1161–1163.
Ma et al., "Design and synthesis of RNA miniduplexes via a synthetic linker approach. 2. Generation of covalently closed, double–stranded cyclic HIV–1 TAR RNA analogs with high Tat–binding affinity," *Nucleic Acids Research*, 21:2585–2589, 1993.
March, J. in Advanced Organic Chemistry, Reactions, Mechanisma, and Structure; John Wiley & Sons; New York, 1992 pp. 293–369.
Nair and Buenger "Regiospecific 5'–Silylation of Nucleosides," *Org. Prep. Proc. Int.*, 22:57–61, 1990.
Pauling, L., "Molecular Architecture and Biological Reactions", *Biological Science* 1946 24(10), 1375–1377.
Perkins et al., "Accelerated Displacement of Duplex DNA strands by a synthetic circular Oligodeoxynucleotide" *J. Chem. Soc., Chem. Commun.* 1993 215–215.
Pon, R. T. "Solid Phase Supports in Olig.nucleotide Synthesis" Ch. 24 in Oligonucleotide Synthesis Protocols, Ed. S. Agrawal, Humana press, 1993, 465–496.
Poopeiko et al., "A Simple Method for Azido Group Reduction," *Syn. Lett.* 1991 p. 342.
Rebek, J. "Molecular Recognition and Biophysical Organic Chemistry", *Account of Chemical Research* 1990, 23(12), 399–404.
Rentzeperis et al., "Contribution of loops and nicks to the formation of DNA dumbbells: Melting behavior and ligand binding", *Biochemistry* 1993, 32, 2564–2572.
Secrist, III, John et al., "Synthesis and Biological Activity of 4'–Thionucleosides" Abstract 21 (Session IV) 10th International Roundtable: Nucleosides, Nucleotides and their Biological Applications, Park city Utah, Sep. 16–20, 1992).

(List continued on next page.)

*Primary Examiner*—James O. Wilson
*Attorney, Agent, or Firm*—Woodcock Washburn Kurtz Mackiewicz & Norris LLP

[57] ABSTRACT

Novel compounds that mimic and/or modulate the activity of wild-type nucleic acids are provided. The novel compounds have modified internucleoside linkages which preferably replace naturally-occurring phosphodiester-5'-methylene linkages with four atom linking groups. Preferred linkages have structures such as, for example, $CH_2-R_A-NR_1-CH_2$, $CH_2-NR_1-R_A-CH_2$, $R_A-NR_1-CH_2-CH_2$, $CH_2-CH_2-NR_1-R_A$, $CH_2-CH_2-R_A-NR_1$, or $NR_1-R_A-CH_2-CH_2$ where $R_A$ is O or $NR_2$. These linkages are prepared from appropriately functionalized nucleosides and oligonucleotides.

20 Claims, 2 Drawing Sheets

OTHER PUBLICATIONS

Sproat et al., 2'-O-Methyloliogrobionucleotides: Synthesis and Applications, Oligonucleotides and Analgos, F. Eckstein Ed., IRL Press, 1991, pp. 49–86.

Trapani et al., "N–1 Alkenyl–N,S–Diacyl–2–Aminobenzenethiols (Enamides) by Ring–Opening of 2,3–Dihydro–1,3–benothiazoles with Aliphatic Carboxylic Anhydrides", *Communications* 1988, 6, 84–87.

Tuladhar, S. M. and D'Silva, C., "A synthetic route to poly–N,N$^1$–dimthylethylenediamines", *Tetrahedron Letters* 1992, 33(16), 2203–2206.

Zon et al., "Phosphorothioate Oligonucleotides" Oligonucleotides and Analogs, A Practical Approach, F. Eckstein, Ed., IRL Press, pp. 87–108 (1991).

Zuckerman, R. et al., "Efficient method for the preparation of peptoids [oligo(N–substituted glycines)] by submonomer solid–phase synthesis", *J. Am. Chem. Soc.* 1992, 114, 10646–10647.

Divakar et al., *J. Chem. Soc. Perkin Trans.* 1982, 1625.

Khurshid et al., *FEBS Letters* 1972, 28:1,25.

Kielanowska et al., *Nucleic Acids Research* 1976, 3:3,817.

Kusmierek et al., *ACTA Biochimica Polonica* 1973, 20:4, 365.

Pike et al., *J. Org. Chem.* 1974, 39:25,3674.

Ransford et al., *J. Carbohydrates—Nucleosides—Nucleotides* 1974, 1:3,275.

Rottman et al., *Biochemistry* 1974, 13,2762.

Singer et al., *Biochemistry* 1976, 15:23,5052.

Tazawa et al., *Biochemistry* 1972, 11,4931.

MODIFIED OLIGONUCLEOTIDES

CROSS REFERENCE TO RELATED APPLICATIONS

This application is a division of application Ser. No. 08/040,903, filed Mar. 31, 1993, (now U.S. Pat. No. 5,386,023, issued Jan. 31, 1995), which is a continuation-in-part of PCT/US92/04294,filed May 21, 1992, (now U.S. Pat. No. 5,610,289, issued Mar. 11, 1997), and of application Ser. No. 07/903,160, filed Jun. 24, 1992, abandoned which are continuations-in-part of application Ser. No. 07/703,619 filed May 21, 1991, (now U.S. Pat. No. 5,378,825, issued Jan. 3, 1995), which is a continuation-in-part of application Ser. No. 07/566,836, filed Aug. 13, 1990, (now U.S. Pat. No. 5,223,618, issued Jun. 29, 1993), and application Ser. No. 07/558,663, filed Jul. 27, 1990 (now U.S. Pat. No. 5,138,045, issued Aug. 11, 1992). This application also is related to the subject matter disclosed and claimed in the following patent applications filed by the present inventors: application Ser. No. 039,979, filed Mar. 30, 1993; U.S. Ser. No. 040,526, filed Mar. 31, 1993, (now U.S. Pat. No. 5,489,677, issued Feb. 6, 1996); and U.S. Ser. No. 040,933, filed Mar. 31, 1993.

FIELD OF THE INVENTION

This invention relates to the design, synthesis and application of nuclease resistant oligonucleotide analogs which are useful for therapeutics, diagnostics and as research reagents. Oligonucleotide analogs are provided having modified linkages replacing the phosphorodiester bonds that normally serve as inter-sugar linkages in wild type nucleic acids. Such analogs are resistant to nuclease degradation and are capable of modulating the activity of DNA and RNA. Methods for synthesizing these oligonucleotide analogs and for modulating the production of proteins are also provided, as are intermediate compositions and synthetic methods.

BACKGROUND OF THE INVENTION

It is well known that most of the bodily states in mammals, including most disease states, are effected by proteins. Proteins, either acting directly or through their enzymatic functions, contribute in major proportion to many diseases in animals and man.

Classical therapeutics generally has focused upon interactions with proteins in an effort to moderate their disease causing or disease potentiating functions. Recently, however, attempts have been made to moderate the production of proteins by interactions with the molecules (i.e., intracellular RNA) that direct their synthesis. These interactions have involved hybridization of complementary "antisense" oligonucleotides or certain analogs thereof to RNA. Hybridization is the sequence-specific hydrogen bonding of oligonucleotides or oligonucleotide analogs to RNA or to single stranded DNA. By interfering with the production of proteins, it has been hoped to effect therapeutic results with maximum effect and minimal side effects.

The pharmacological activity of antisense oligonucleotides and oligonucleotide analogs, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modification of oligonucleotides to render them resistant to nucleases therefore is greatly desired.

Modification of oligonucleotides to enhance nuclease resistance generally has taken place on the phosphorus atom of the sugar-phosphate backbone. Phosphorothioates, methyl phosphonates, phosphoramidates and phosphorotriesters have been reported to confer various levels of nuclease resistance. Phosphate-modified oligonucleotides, however, generally have suffered from inferior hybridization properties. See, e.g., Cohen, J. S., ed. *Oligonucleotides: Antisense Inhibitors of Gene Expression,* (CRC Press, Inc., Boca Raton, Fla., 1989).

Another key factor is the ability of antisense compounds to traverse the plasma membrane of specific cells involved in the disease process. Cellular membranes consist of lipid-protein bilayers that are freely permeable to small, nonionic, lipophilic compounds and are inherently impermeable to most natural metabolites and therapeutic agents. See, e.g., Wilson, *Ann. Rev. Biochem.* 1978, 47, 933. The biological and antiviral effects of natural and modified oligonucleotides in cultured mammalian cells have been well documented. It appears that these agents can penetrate membranes to reach their intracellular targets. Uptake of antisense compounds into a variety of mammalian cells, including HL-60, Syrian Hamster fibroblast, U937, L929, CV-1 and ATH8 cells has been studied using natural oligonucleotides and certain nuclease resistant analogs, such as alkyl triesters and methyl phosphonates. See, e.g., Miller, et al., *Biochemistry* 1977, 16, 1988; Marcus-Sekura, et al., *Nucleic Acids Research* 1987, 15, 5749; and Loke, et al., *Top. Microbiol. Immunol.* 1988, 141, 282.

Often, modified oligonucleotides and oligonucleotide analogs are internalized less readily than their natural counterparts. As a result, the activity of many previously available antisense oligonucleotides has not been sufficient for practical therapeutic, research or diagnostic purposes. Two other serious deficiencies of prior art compounds designed for antisense therapeutics are inferior hybridization to intracellular RNA and the lack of a defined chemical or enzyme-mediated event to terminate essential RNA functions.

Modifications to enhance the effectiveness of the antisense oligonucleotides and overcome these problems have taken many forms. These modifications include base ring modifications, sugar moiety modifications and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the pro-chiral phosphate moiety. For example, Matteucci, *Tetrahedron Letters* 1990, 31, 2385 disclosed the replacement of the phosphorus atom with a methylene group. However, this replacement yielded unstable compounds with nonuniform insertion of formacetal linkages throughout their backbones. Cormier, et al., *Nucleic Acids Research* 1988, 16, 4583, disclosed replacement of phosphorus with a diisopropylsilyl moiety to yield homopolymers having poor solubility and hybridization properties. Stirchak, et al., *Journal of organic Chemistry* 1987, 52, 4202 disclosed replacement of phosphorus linkages by short homopolymers containing carbamate or morpholino linkages to yield compounds having poor solubility and hybridization properties. Mazur, et al., *Tetrahedron* 1984, 40, 3949, disclosed replacement of a phosphorus linkage with a phosphonic linkage yielded only a homotrimer molecule. Goodchild, *Bioconjugate Chemistry* 1990, 1, 165, disclosed ester linkages that are enzymatically degraded by esterases and, therefore, are not suitable for antisense applications.

The limitations of available methods for modification of the phosphorus backbone have led to a continuing and long felt need for other modifications which provide resistance to nucleases and satisfactory hybridization properties for antisense oligonucleotide diagnostics and therapeutics.

OBJECTS OF THE INVENTION

It is an object of the invention to provide oligonucleotide analogs for diagnostic, research, and therapeutic use.

It is a further object of the invention to provide oligonucleotide analogs capable of forming duplex or triplex structures.

It is a further object of the invention to provide oligonucleotide analogs having enhanced cellular uptake.

Another object of the invention is to provide oligonucleotide analogs having greater efficacy than unmodified antisense oligonucleotides.

It is yet another object of the invention to provide methods for synthesis and use of oligonucleotide analogs.

These and other objects will become apparent to persons of ordinary skill in the art from a review of the present specification and the appended claims.

SUMMARY OF THE INVENTION

The present invention provides novel compounds that mimic and/or modulate the activity of wild-type nucleic acids. In general, the compounds contain a selected nucleoside sequence which is specifically hybridizable with a targeted nucleoside sequence of single stranded or double stranded DNA or RNA. At least a portion of the compounds of the invention has structure I:

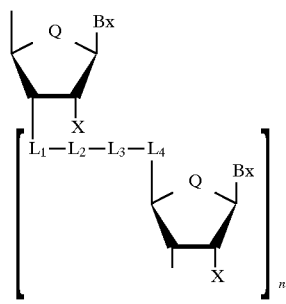

wherein:

$L_1$—$L_2$—$L_3$—$L_4$ is $CH_2$—$R_A$—$NR_1$—$CH_2$, $CH_2$—$NR_1$—$R_A$—$CH_2$, $R_A$—$NR_1$—$CH_2$—$CH_2$ or $NR_1$—$R_A$—$CH_2$—$CH_2$;

$R_A$ is O or $NR_2$;

$R_1$ and $R_2$ are the same or different and are H; alkyl or substituted alkyl having 1 to about 10 carbon atoms; alkenyl or substituted alkenyl having 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms; alicyclic; heterocyclic; a reporter molecule; an RNA cleaving group; a group for improving the pharmacokinetic properties of an oligonucleotide; or a group for improving the pharmacodynamic properties of an oligonucleotide;

$B_X$ is a nucleosidic base;

n is an integer greater than 0;

Q is O, S, $CH_2$, CHF or $CF_2$;

X is H; OH; alkyl or substituted alkyl having 1 to about 10 carbon atoms; alkaryl, substituted alkaryl, aralkyl, or substituted aralkyl having 7 to about 14 carbon atoms; F; Cl; Br; CN; $CF_3$; $OCF_3$; OCN; O-alkyl; S-alkyl; N-alkyl; O-alkenyl; S-alkenyl; N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino or substituted silyl; an RNA cleaving group; a group for improving the pharmacokinetic properties of an oligonucleotide; or a group for improving the pharmacodynamic properties of an oligonucleotide.

The compounds of the invention are prepared by coupling preselected 3'-functionalized and 4'-functionalized nucleosides and/or oligonucleotides under conditions effective to form the above-noted $L_1$—$L_2$—$L_3$—$L_4$ linkages. In certain embodiments, a 3'-formyl nucleoside or oligonucleotide synthon is reacted with a 5'-hydroxylamino or 5'-hydrazino nucleoside or oligonucleotide synthon. In other embodiments, a 5'-formyl synthon is reacted with a 3'-methylhydroxylamino or 3'-methylhydrazino synthon. In still further embodiments, linkages having structure CH=N—$R_A$—$CH_2$, $CH_2$—CH=N—$R_A$, $CH_2$—$R_A$—N=CH, or $R_A$—N=CH—$CH_2$ where $R_A$ is O or $NR_1$ are formed by coupling synthons having structures II and III:

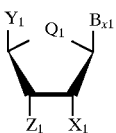

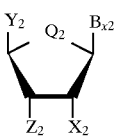

wherein:

$Z_1$ and $Y_2$ are selected such that
(i) $Z_1$ is C(O)H and $Y_2$ is $CH_2R_ANH_2$; or
(ii) $Z_1$ is $CH_2R_ANH_2$ and $Y_2$ is C(O)H;
(iii) $Z_1$ is $CH_2C(O)H$ and $Y_2$ is $R_ANH_2$; or
(iv) $Z_1$ is $R_ANH_2$ and $Y_2$ is $H(O)CCH_2$;

$Y_1$ is aminomethyl, hydrazinomethyl, hydroxymethyl, C-formyl, phthalimidohydroxymethyl, aryl-substituted imidazolidino, aminohydroxylmethyl, ortho-methylaminobenzenethio, methylphosphonate, methylalkylphosphonate, a nucleoside, a nucleotide, an oligonucleotide, an oligonucleoside, or a hydroxyl-protected or amine-protected derivative thereof;

$Z_2$ is hydroxyl, aminomethyl, hydrazinomethyl, hydroxymethyl, C-formyl, phthalimidohydroxy $Z_2$ is hydroxyl, aminomethyl, hydrazinomethyl, hydroxymethyl, C-formyl, phthalimidohydroxymethyl, aryl-substituted imidazolidino, aminohydroxylmethyl, ortho-methylaminobenzenethio, methylphosphonate, methylalkylphosphonate, a nucleoside, a nucleotide, an oligonucleotide, an oligonucleoside, or a hydroxyl-protected or amine-protected derivative thereof;

$B_{X1}$ and $B_{X2}$ are, independently, nucleosidic bases; $Q_1$ and $Q_2$ are, independently, O, S, $CH_2$, CHF or $CF_2$; and $X_1$ and $X_2$ are, independently, H, OH, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligonucleotide, or a group for improving the pharmacodynamic properties of an oligonucleotide.

In preferred embodiments, the resulting compounds are reduced to produce the linkages $CH_2$—Nh—$R_A$—$CH_2$, $CH_2$—$R_A$—NH—$CH_2$, or $R_A$—NH—$CH_2$—$CH_2$, respectively.

DETAILED DESCRIPTION OF THE INVENTION

Figure 1:
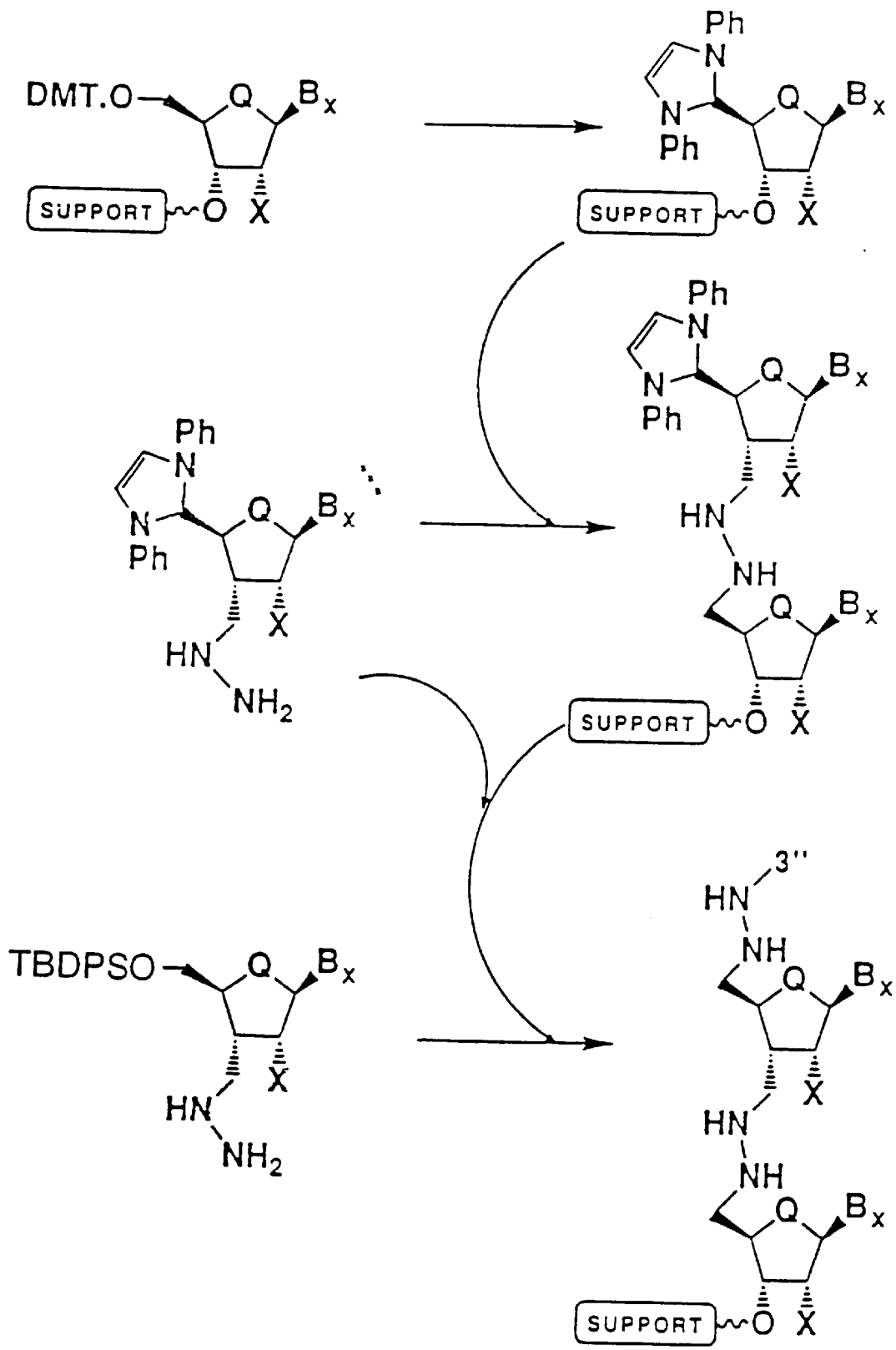
FIG. 1 is a schematic, synthetic scheme in accordance with certain embodiments of the invention.

The term "nucleoside" as used in connection with this invention refers to a unit made up of a heterocyclic base and its sugar. The term "nucleotide" refers to a nucleoside having a phosphate group on its 3' or 5' sugar hydroxyl group. Thus nucleosides, unlike nucleotides, have no phosphate group. "Oligonucleotide" refers to a plurality of joined nucleotide units formed in a specific sequence from naturally occurring bases and pentofuranosyl groups joined through a sugar group by native phosphodiester bonds. This term refers to both naturally occurring and synthetic species formed from naturally occurring subunits.

The compounds of the invention generally can be viewed as "oligonucleotide analogs", that is, compounds which function like oligonucleotides but which have non-naturally occurring portions. oligonucleotide analogs can have altered sugar moieties, altered base moieties or altered inter-sugar linkages. For the purposes of this invention, an oligonucleotide analog having non-phosphodiester bonds, i.e., an altered inter-sugar linkage, is considered to be an "oligonucleoside." The term "oligonucleoside" thus refers to a plurality of nucleoside units joined by linking groups other than native phosphodiester linking groups. The term "oligomers" is intended to encompass oligonucleotides, oligonucleotide analogs or oligonucleosides. Thus, in speaking of "oligomers" reference is made to a series of nucleosides or nucleoside analogs that are joined via either natural phosphodiester bonds or other linkages, including the four atom linkers of this invention. Although the linkage generally is from the 3' carbon of one nucleoside to the 5' carbon of a second nucleoside, the term "oligomer" can also include other linkages such as 2'-5' linkages.

Oligonucleotide analogs also can include other modifications consistent with the spirit of this invention, particularly modifications that increase nuclease resistance. For example, when the sugar portion of a nucleoside or nucleotide is replaced by a carbocyclic moiety, it is no longer a sugar. Moreover, when other substitutions, such as a substitution for the inter-sugar phosphorodiester linkage are made, the resulting material is no longer a true nucleic acid species. All such compounds are considered to be analogs. Throughout this specification, reference to the sugar portion of a nucleic acid species shall be understood to refer to either a true sugar or to a species taking the structural place of the sugar of wild type nucleic acids. Moreover, reference to inter-sugar linkages shall be taken to include moieties serving to join the sugar or sugar analog portions in the fashion of wild type nucleic acids.

This invention concerns modified oligonucleotides, i.e., oligonucleotide analogs or oligonucleosides, and methods for effecting the modifications. These modified oligonucleotides and oligonucleotide analogs exhibit increased stability relative to their naturally occurring counterparts. Extracellular and intracellular nucleases generally do not recognize and therefore do not bind to the backbone-modified compounds of the invention. In addition, the neutral or positively charged backbones of the present invention can be taken into cells by simple passive transport rather than by complicated protein-mediated processes. Another advantage of the invention is that the lack of a negatively charged backbone facilitates sequence specific binding of the oligonucleotide analogs or oligonucleosides to targeted RNA, which has a negatively charged backbone and will repel similarly charged oligonucleotides. Still another advantage of the present invention is it presents sites for attaching functional groups that initiate cleavage of targeted RNA.

The modified internucleoside linkages of this invention preferably replace naturally-occurring phosphodiester-5'-methylene linkages with four atom linking groups to confer nuclease resistance and enhanced cellular uptake to the resulting compound. Preferred linkages have structure $CH_2$—$R_A$—$NR_1$—$CH_2$, $CH_2$—$NR_1$—$R_A$—$CH_2$, $R_A$—$NR_1$—$CH_2$—$CH_2$, or $NR_1$—$R_A$—$CH_2$—$CH_2$ where $R_A$ is O or $NR_2$.

Generally, these linkages are prepared by functionalizing the sugar moieties of two nucleosides which ultimately are to be adjacent to one another in the selected sequence. In a 4' to 3' sense, an "upstream" synthon such as structure II is modified at its terminal 3' site, while a "downstream" synthon such as structure III is modified at its terminal 4' site. More specifically, the invention provides efficient syntheses of oligonucleosides via intermolecular reductive coupling.

$B_{X1}$ and $B_{X2}$ can be nucleosidic bases selected from adenine, guanine, uracil, thymine, cytosine, 2-aminoadenosine or 5-methylcytosine, although other non-naturally occurring species can be employed to provide stable duplex or triplex formation with, for example, DNA. Representative bases are disclosed in U.S. Pat. No. 3,687,808 (Merigan, et al.), which is incorporated herein by reference.

$Q_1$ and $Q_2$ can be S, $CH_2$, CHF $CF_2$ or, preferably, O. See, e.g., Secrist, et al., Abstract 21, Synthesis and Biological Activity of 4'-Thionucleosides, Program & Abstracts, Tenth International Roundtable, Nucleosides, Nucleotides and their Biological Applications, Park City, Utah, Sep. 16–20, 1992.

$X_1$ and $X_2$ are, independently, H, OH, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligonucleotide, or a group for improving the pharmacodynamic properties of an oligonucleotide. It is intended that the term "alkyl" denote branched and straight chain hydrocarbyl residues, including alkyl groups having one or more $^3H$ and/or $^{14}C$ atoms. It is preferred that X is H or OH, or, alternatively F, O-alkyl or O-alkenyl, especially where Q is O. Preferred alkyl and alkenyl groups have from 1 to about 10 carbon atoms.

$Y_1$ and $Z_2$ can be aminomethyl, hydrazinomethyl, hydroxymethyl, C-formyl, phthalimidohydroxymethyl, aryl-substituted imidazolidino, aminohydroxylmethyl, orthomethylaminobenzenethio, methylphosphonate, methylalkylphosphonate, a nucleoside, a nucleotide, an oligonucleotide, an oligonucleoside, or a hydroxyl-protected or amine-protected derivative thereof. In addition, $Z_2$ can be hydroxyl. Preferably, $Y_1$ is a protected hydroxymethyl group or a nucleoside or oligonucleoside attached by, for example, a phosphodiester-5'-methylene linkage or some other four atom linking group, and $Z_2$ is a protected hydroxyl group or a nucleoside or oligonucleoside attached by, for example, a phosphodiester-3'-hydroxyl linkage or some other four atom linking group.

It is preferred that the oligonucleotide analogs of the invention comprise from about 5 to about 50 subunits having the given structure (i.e., n=5–50). While each subunit of the oligonucleotide analogs can have repetitive structure I, such need not be the case. For example, the subunits can have alternating or more random structures.

The invention is also directed to methods for the preparation of oligonucleosides with modified inter-sugar linkages. These modifications may be effected using solid supports which may be manually manipulated or used in conjunction with a DNA synthesizer using methodology commonly known to those skilled in DNA synthesizer arts. Generally, the procedure involves functionalizing the sugar moieties of two nucleosides which will be adjacent to one another in the selected sequence. In a 5' to 3' sense, an "upstream" synthon such as structure II is modified at its terminal 3' site, while a "downstream" synthon such as structure III is modified at its terminal 5' site.

More specifically, certain linkages can be formed by selecting a 3'-C-formyl derivatized compound as the upstream synthon and a 5'-aminohydroxy derivatized compound as the downstream synthon. Coupling then is effected to provide, for example, a dinucleoside having an oxime linkage. In this instance, the oxime is present as E/Z isomers, which are separated by HPLC. The oxime nitrogen atom is adjacent to a carbon atom on the 3' end of the upstream nucleoside. Dinucleosides having the oxime nitrogen adjacent to a carbon atom on the 5' or downstream nucleoside are synthesized utilizing a 5'-C-formyl derivatized compound as the upstream synthon and a 3'-deoxy-3'-aminohydroxymethyl derivatized compound as the downstream synthon, again providing E/Z isomers. In both instances the oxime linked compound can be incorporated directly into an oligomer and/or can be reduced to a corresponding hydroxyamino linked species. Reduction of oxime linked dinucleosides either as the dinucleoside or as a dinucleoside moiety in an oligomer with sodium cyanoborohydride yields the corresponding hydroxylamino linked compounds. Hydroxylamino linked compounds can be alkylated at the amino moiety of the hydroxylamino linkage to yield a corresponding N-alkylamino linkage.

3'-C-formyl derivatized nucleosides can be formed via several synthetic pathways. The presently preferred method utilizes a radical carbonylation of the corresponding 3'-deoxy-3'-iodo nucleoside. The iodo compound is treated with CO, 2,2'-azobisisobutrylonitrile (AIBN), and tris (trimethylsilyl)silane (TTMS). Alternately, 3'-C-formyl derivatized compounds can be synthesized from either a 3'-deoxy-3'-cyano sugar or nucleoside. Both 5'-C-formyl (also identified as 5'-aldehydo) and 3'-C-formyl group can be blocked in a facile manner utilizing o-methylaminobenzenthiol as a blocking group. The 5'- and 3'-C-formyl groups can be deblocked with silver nitrate oxidation.

An alternate method of 3'-C-formyl nucleoside synthesis employs 1-O-methyl-3'-deoxy-3'-O-methylaminobenzene thiol-5'-O-trityl-β-D-erythro-pento furanoside, which serves as a precursor for any 3'-deoxy-3'-C-formyl nucleoside. The 1-O-methyl-3'-deoxy-3'-O-methyl amino benzenethiol-5'-O-trityl-β-D-erythro-pentofuranoside is reacted with an appropriate base utilizing standard glycosylation conditions and then deblocked to yield the nucleoside. In yet another method, a 3'-deoxy-3'-cyano nucleoside is prepared from either the corresponding 3'-deoxy-3'-iodo nucleoside or by glycosylation with 1-O-methyl-3'-deoxy-3'-O-cyano-5'-O-trityl-β-D-erythro-pentofuranoside.

Resulting dinucleosides from any of the above described methods, linked by hydrazines, hydroxyl amines and other linking groups, can be protected by a dimethoxytrityl group at the 5'-hydroxyl and activated for coupling at the 3'-hydroxyl with cyanoethyldiisopropylphosphite moieties. These dimers can be inserted into any desired sequence by standard, solid phase, automated DNA synthesis utilizing phosphoramidite coupling chemistries. The protected dinucleosides are linked with the units of a specified DNA sequence utilizing normal phosphodiester bonds. The resulting oligonucleotide analog or oligomer has a "mixed" backbone containing both phosphodiester linkages and four atoms linkages of the inventions. In this manner, a sequence-specific 15-mer oligonucleotide can be synthesized to have seven hydroxylamine, hydrazine or other type linked dinucleosides attached via alternating phosphodiester linkages. Such a structure will provide increased solubility in water compared to fully modified oligomers, which may contain linkages of the invention.

Oligonucleosides containing a uniform backbone linkage can be synthesized by use of CPG-solid support and standard nucleic acid synthesizing machines such as Applied Biosystems Inc. 380B and 394 and Milligen/Biosearch 7500 and 8800s. The initial nucleoside (number 1 at the 3'-terminus) is attached to a solid support such as controlled pore glass. In sequence specific order, each new nucleoside is attached either by manual manipulation or by the automated synthesizer system. In the case of a methylenehydrazine linkage, the repeating nucleoside unit can be of two general types—a nucleoside with a 5'-protected aldehydic function and a 3'-deoxy-3'-C-hydrazinomethyl group, or a nucleoside bearing a 5'-deoxy-5'-hydrazino group protected by an acid labile group and a 3'-deoxy-3'-C-formyl group. In each case, the conditions which are repeated for each cycle to add the subsequent sequence required base include: acid washing to remove the 5'-aldehydo protecting group; addition of the next nucleoside with a 3'-methylenehydrazino group to form the respective hydrazone connection; and reduction with any of a variety of agents to afford the desired methylenehydrazine linked CPG-bound oligonucleosides. One such useful reducing agent is sodium cyanoborohydride.

A preferred method is depicted in FIG. 1. This method employs a solid support to which has been bound a downstream synthon having a protected 5' site. Preferably, the 5' site of said synthon is protected with DMT. Thereafter, the 5' site of the synthon is liberated with mild acid, washed, and oxidized to produce an intermediate product. In one preferred method, the aldehyde derivative reacts with N,N-diphenylethylene diamine to produce an intermediary product, a 5'-diphenylimidazolidino protected synthon. In a more preferred method the 5'-diphenylimidazolidino protected synthon is directly loaded on the support. With either method, the intermediary product can be subsequently deblocked to provide a synthon with a nucleophilic 5' position.

An upstream synthon having a protected 5'-aldehyde group, such as a 5'-diphenylimidazolidino protected 3'-deoxy-3'-C-hydrazine base, is coupled with the bound downstream synthon by, for example, the addition of sodium cyanoborohydride. Following a wash step, a dinucleoside linked through a hydrazino moiety is formed. Thereafter, the cycle can be repeated by the addition of an upstream synthon, followed by acid/ base deprotection to create a polymeric synthon of a desired sequence containing modified inter-sugar linkages. In some preferred embodiments of this invention, the upstream synthon is a 5'-DMT protected 3'-C-hydrazine base.

One preferred process employs a diphenylethyldiamine adduct (1,3-disubstituted imidazolidino) to protect the electrophilic center of the downstream synthon during attachment to the solid support.

Moffatt, et al., *J. Am. Chem. Soc.* 1968, 90, 5337. The downstream synthon can be attached to a solid support such as a controlled pore glass support or other suitable supports known to those skilled in the art. Attachment can be effected via standard procedures. Gait, M. J., ed., *Oligonucleotide Synthesis, A Practical Approach* (IRL Press 1984). Alternatively, the protected bound nucleoside can be oxidized by standard oxidizing procedures. Bound downstream synthons preferably are reacted with hydrazine to produce a Schiff's base, which can be reduced. Hydroxylamine is also a preferred reactant in this method.

Figure 2:
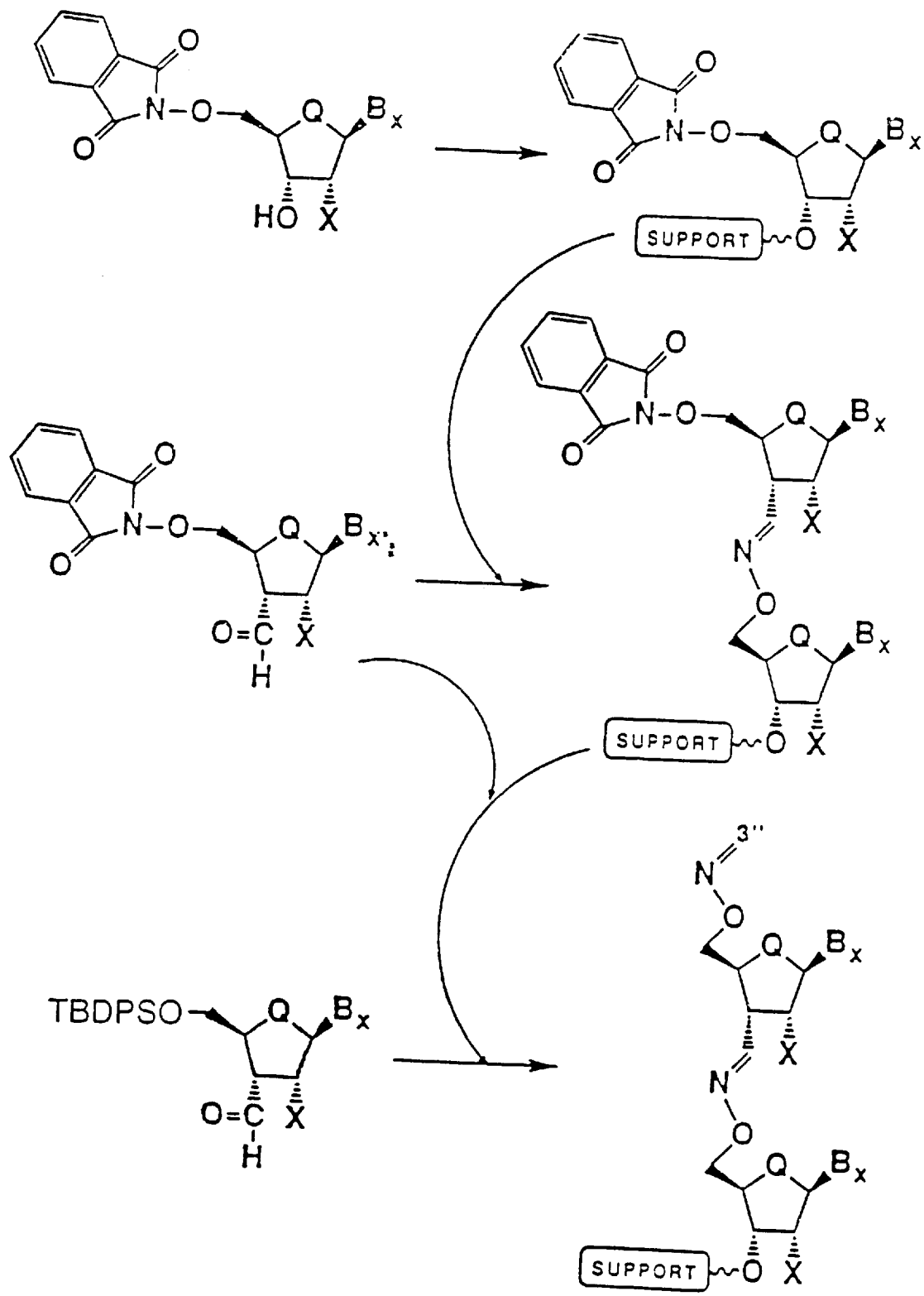
FIG. 2 is a schematic, synthetic scheme in accordance with further embodiments of the invention.

A further method of synthesizing uniform backbone linked oligonucleosides is depicted in FIG. 2. This method also employs a solid support to which has been bound a downstream synthon with a protected 5' site. The 5' site preferably is protected with a phthalimido group. The 5' site of the downstream synthon is liberated with methylhydrazine in DCM and washed with DCM:methanol. The aminohydroxyl group at the 5' position of the upstream synthon also is protected with a phthalimido group to yield a 5'-phthalimido protected 3'-deoxy-3'-C-formyl nucleoside, which is reacted with the downstream synthon. Deprotection at the 5' position and washing liberates the next 5'-aminohydroxy reaction site. The cycle is repeated with the further addition of upstream synthon until the desired sequence is constructed. Each nucleoside of this sequence is connected with oxime linkages. The terminal nucleoside of the desired oligonucleoside is added to the sequence as a 5'-OTBDMSi blocked 3'-deoxy-3'-C-formyl nucleoside. The oxime linked oligonucleoside can be removed from the support. If a aminohydroxyl linked oligonucleoside is desired, the oxime linkages are reduced with sodium cyanoborohydride. Alternately reduction can be accomplished while the oxime linked oligonucleoside is still connected to the support.

The reactions of Examples 25–27 represent improved syntheses of 3'-O-NH$_2$ nucleosides. In forming —O— moieties on sugars, it is theoretically possible to displace a leaving group, as for instance a tosyl group, with hydroxylamine. However, Files, et al., *J. Am. Chem. Soc.* 1992, 14, 1493 have shown that such a displacement leads to a preponderance of —NHOH moieties and not to the desired —O—NH$_2$ moieties. Further, the reaction sequence of Examples 25–27 represents an improved synthesis compared to that illustrated in European Patent Application 0 381 335. The synthetic pathway of that patent application requires the use of a xylo nucleoside as the staring material. Xylo nucleosides are less readily obtainable than the ribonucleoside utilized in Examples 25–27.

The methods of the invention can be modified for use with either solution-phase or solid-phases techniques. For example, the compounds of the invention can be synthesized using controlled pore glass (CPG) supports and standard nucleic acid synthesizing machines such as Applied Biosystems Inc. 380B and 394 and Milligen/Biosearch 7500 and 8800s. Each new nucleoside is attached either by manual manipulation or by automated techniques.

A wide variety of protecting groups can be employed in the methods of the invention. See, e.g., Beaucage, et al., *Tetrahedron* 1992, 12, 2223. In general, protecting groups render chemical functionality inert to specific reaction conditions, and can be appended to and removed from such functionality in a molecule without substantially damaging the remainder of the molecule. Representative hydroxyl protecting groups include t-butyldimethylsilyl (TBDMSi), t-butyldiphenylsilyl (TBDPSi), dimethoxytrityl (DMTr), monomethoxytrityl (MMTr), and other hydroxyl protecting groups as outlined in the above-noted Beaucage reference.

Scheme I illustrates the conversion of a 4'-aldehydo nucleoside to a 5'-aldehydo nucleoside. This reaction is exemplified in Example 31. Scheme II illustrates the generation of a 5'-aldehydo methyl sugar. This is exemplified in Example 29. Scheme III illustrates the formation of an 5'-iodo nucleoside. Similar methodology is used to generate an active iodo group on a terminal hydroxyl of a dimeric unit in Scheme IX. In Scheme III, the iodo nucleoside is further derivatized to a 6'-aldehydo nucleoside via an allyl substituted nucleoside. This is exemplified in Examples 46 and 47.

Scheme IV illustrates a free radical reaction of a —O-methyleneamino nucleoside of Scheme 1 to a 5'-amino 5'-homo nucleoside. This is exemplified in Example 45. Scheme V illustrates use of a Mitsunobu reaction on a 5'-homo nucleoside to synthesize an oxyamine homonucleoside, i.e. a 6'—O=13 NH$_2$ 5'-homo nucleoside. This is exemplified in Examples 49, 50, and 51. Scheme VI illustrates N-alkylation of the amino moiety of a 6'-amino-5'-deoxy-5'-homo nucleoside. This is exemplified in Examples 56, 57, and 58. Such N-alkylation is desirable where the amino moiety subsequently will be reacted with a thiol moiety. The N-alkylated product of such a reaction exhibits greater stability to acid than does the non-alkylated S—N bond. This is particularly useful in solid support synthesis wherein acid removal of trityl groups is commonly practiced. However, for other synthesis, such as solution synthesis, this may not be a concern.

Schemes VII to XV illustrate the use of nucleosides for the assembly of dimeric, trimeric and other, higher order oligonucleosides. In Scheme VII, nucleosides 3 and 31 are joined via an acid catalyzed coupling reaction to form an —O-nitrilomethylidyne linkage between the respective two nucleosides. This is exemplified in Example 32. Dimeric oligonucleoside 32 can be reduced to an iminomethylene linkage that, in turn, can be alkylated to a (methylimino) methylene linkage, as exemplified in Example 33.

Scheme VIII illustrates the coupling of nucleoside 3 to nucleoside 5. This scheme is analogous to Scheme VII with the exception that in Scheme VII a three atom linkage is created whereas in Scheme VII a four atom linkage is created. Nucleosides 3 and 5 are joined in Step 1 to form an —O-nitrilo linkage that is reduced in Step 2 to an —O-imino linkage. Alkylation occurs in Step 3 to a —O-methylimino linkage, with final deblocking in Step 4. These steps are exemplified in Example 28. The alkylation reaction in Step 3 is accompanied by deblocking the t-butyldimethylsilyl protecting group at the 5' terminus of the dimer. Advantageous use of this deblocking reaction also is utilized in other Schemes. Deblocking of the t-butyldiphenylsilyl group used to protect the 3' terminus of the dimer is effected using tetra-n-butylammonium fluoride.

The alkylation step can be used to introduce other, useful, functional molecules on the macromolecule. Such useful functional molecules include but are not limited to reporter molecules, RNA cleaving groups, groups for improving the pharmacokinetic properties of an oligonucleotide, and groups for improving the pharmacodynamic properties of an oligonucleotide. Such molecules can be attached to or conjugated to the macromolecule via attachment to the nitrogen atom in the backbone linkage. Alternatively, such molecules can be attached to pendent groups extending from the 2' position of the sugar moiety of one or more of the nucleosides of the marcromolecules. Examples of such other useful functional groups are provided by U.S. patent application Ser. No. 782,374, filed Oct. 24, 1991, entitled Derivatized Oligonucleotides Having Improved Uptake & Other Properties, assigned to the same assignee as this application, herein incorporated by reference, and in other of the above-referenced patent applications.

Scheme IX illustrates a synthetic scheme utilized to prepare dimers, trimers, and other, higher order oligonucleosides having homogenous linkages between nucleosides. In this scheme, nucleosides 10 and 12 are linked to form an iminomethylene linkage. Advantageous use of the alkylating-5' terminus deblocking step of Scheme VII is effected to remove the blocking group at the 5' terminus of the dimeric oligonucleoside 14. Using the iodination reaction of Scheme III, the dimer is then converted to a 5' terminus iodo intermediate. A further 3'-O-methyleneamino nucleosidic unit 10 then can be added to the dimer to form a trimer, followed by deblocking and alkylation. This reaction sequence can be repeated any number of times to form a higher order oligonucleoside. The oligonucleoside is deblocked at the 3' terminus.

Scheme X illustrates the use of an 1-O-alkyl sugar that is first linked to a nucleoside. Reduction followed by alkylation and deblocking yields an —O-(methylimino)methylene linkage joining the 1-O-alkyl sugar and the nucleoside, as exemplified by Example 34. This structure is then blocked at the 5' terminus, as exemplified by Example 35. The fully blocked, linked sugar-nucleoside structure is then subjected to glycosylation to add a heterocyclic base to the sugar moiety and thus form a dimeric nucleoside structure, as in Example 36. After glycosylation, removal of the 5' terminus blocking group and chromatographic separation of α and β anomers, as exemplified by Example 37, yields a dimer. This dimer can be further elongated as per the procedure of Scheme IX. Examples 39 and 40 exemplify the addition of an adenine, cytosine and guanine base to a thymidine-methyl sugar dimer to form T-A, T-C and T-G dimers in addition to the T-T dimer of Scheme IX. Examples 41, 42, and 43 exemplify the formation of A-T, A-A, A-C, A-G, C-T, C-A, C-C, C-G, G-T, G-A, G-C and G-G dimers. Each may be further elongated as per the procedures of Scheme IX.

Scheme XI illustrates the formation of an iminooxymethylene linkage. Example 48 describes the preparation of the 5'-O-trityl protected xylo starting nucleoside and Example 52 describes the reaction of compound 50 with compound 54 to form a dimeric unit. Continuing within Scheme XI, to prepare dimeric units that can be used as solid support building blocks (Example 53), the backbone nitrogen atom is alkylated, followed by simultaneous removal of both the 5'-O-trityl and the 3'-O-(t-butyldiphenylsilyl) protecting groups with trifluoroacetic acid. The 5'-terminus hydroxyl group is blocked with dimethoxytriryl (Example 54), followed by forming an active phosphoramidate dimer (Example 55).

Scheme XII illustrates the preparation of a thiol intermediate and the use of that intermediate with an amino nucleoside to form a S-iminomethylene linkage (Example 58). As with the reactions of Scheme XI, a dimeric unit having an active phosphoramidate moiety can be formed. This is exemplified by Examples 59 and 60.

Scheme XIII illustrates the preparation of a nucleoside intermediate and coupling of that intermediate to a further nucleoside, as exemplified in Example 61, to form a nitrilo-1,2-ethanediyl linkage. This linkage can be reduced to an imino-1,2-ethanediyl linkage, as exemplified in Example 62. Further, in a manner similar to Schemes XI and XII, Scheme XIII illustrates the preparation of an active phosphoramidate species, as exemplified in Examples 63, 64, and 65.

Scheme XIV illustrates the preparation of a 2' substituted nucleoside, as exemplified in Example 66, and conversion of that 2' substituted nucleoside to a further nucleoside having an active linkage forming moiety (Example 67). Linkage of this 2' substituted nucleoside to a further nucleoside (Example 68) is followed by conversion to an active phosphoramidate (Example 69). Substitution of the 2' position in a macromolecule of the invention, as noted above, is useful for the introduction of other molecules, including the introduction of reporter molecules, RNA cleaving groups, groups for improving the pharmacokinetic properties of an oligonucleotide, and groups for improving the pharmacodynamic properties of an oligonucleotide as well as other groups including but not limited to O, S and NH alkyl, aralkyl, aryl, heteroaryl, alkenyl, alkynyl and $^{14}$C containing derivatives of these groups, F, Cl, Br, CN, $CF_3$, $OCF_3$, OCN, $SOCH_3$, $SO_2CH_3$, $ONO_2$, $NO_2$, $N_3$, $NH_2$, heterocycloalkyl, heterocycloalkaryl, aminoalkylamino, polyalkylamino and substituted silyl.

Further illustrated in Scheme XIV is the preparation of a carbocyclic nucleoside (Example 70), joining of that carbocyclic nucleoside with a further nucleoside via a linkage of the invention (Example 71), and formation of an active phosphoramidate (Example 76). A further sequence of reactions are also illustrated in Scheme XIV, wherein a carbocyclic nucleoside is derivatized at its 2' positions (Example 73) and converted to a further nucleoside (Example 74). As with the other reactions of this scheme, a dimer is first formed (Example 75), and then derivatized with an active phosphoramidate (Example 76). The dimers of this scheme having a 3' phosphoramidite moiety are used as in Schemes XII, XII and XIII to link the oligonucleosides of the invention to other nucleosides via a phosphodiester, phosphorothioate or other similar phosphate based linkage.

Scheme XV illustrates a further carbocyclic containing, dimeric nucleoside. Internucleoside conversion is exemplified in Examples 77 and 78, and formation of a dimeric structure is exemplified in Example 79. The dimeric structure of Scheme XV shows a carbocyclic nucleoside as the 5' nucleoside of the dimer, while Scheme XIV shows a carbocyclic nucleoside as the 3' nucleoside of the dimer. Use of carbocyclic nucleosides for both nucleoside intermediates, in the manner as described for other of the reaction schemes, results in a dimer having a carbocyclic nucleoside at both the 3' and 5' locations.

Scheme XVI illustrates generic structures that are prepared from the nucleosides and oligonucleoside of the previous schemes. Exemplary macromolecules of the invention are described for both solid support and solution phase synthesis in Example 81.

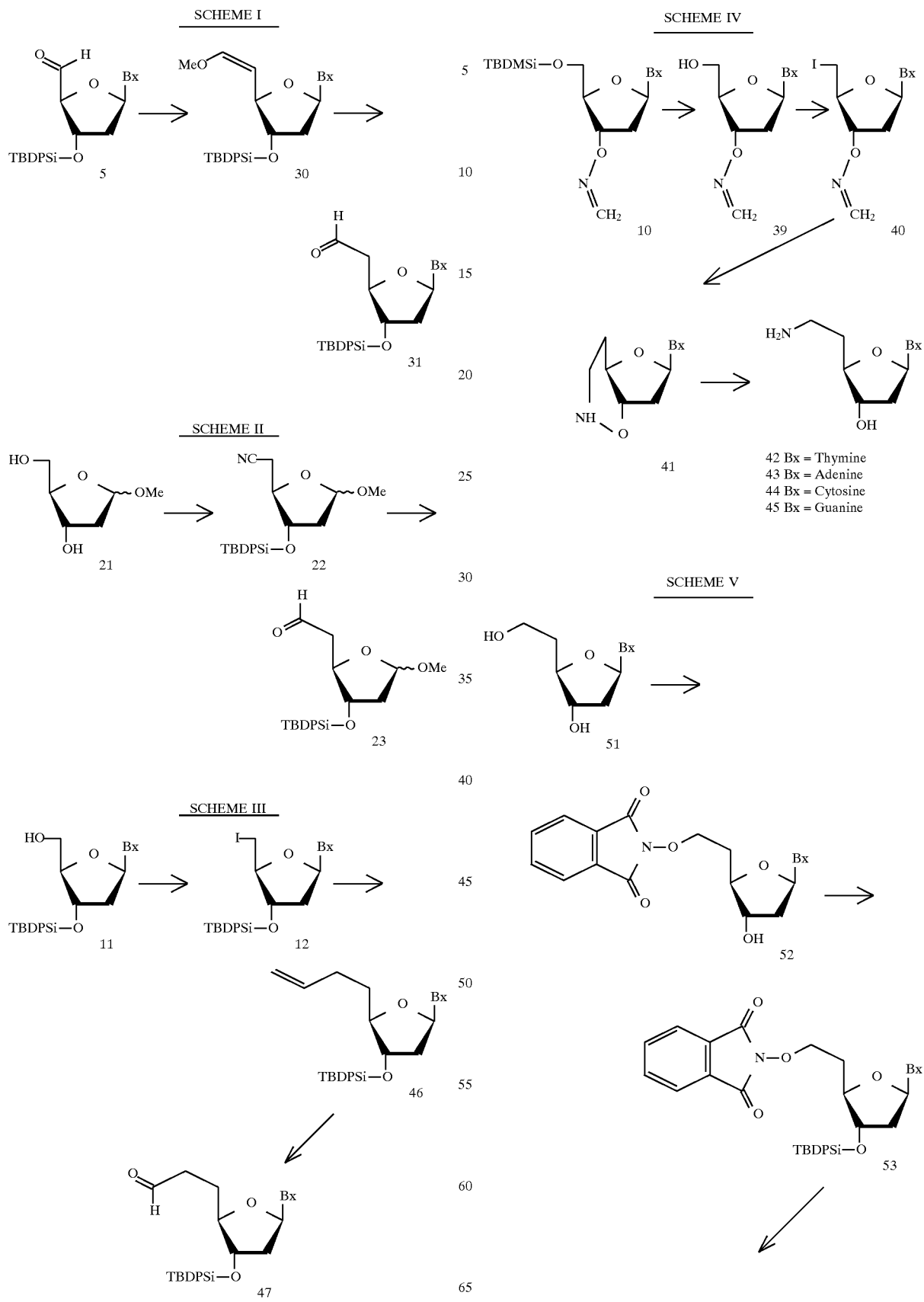

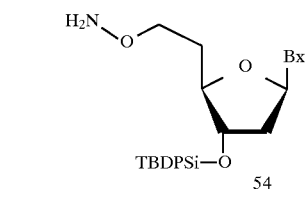
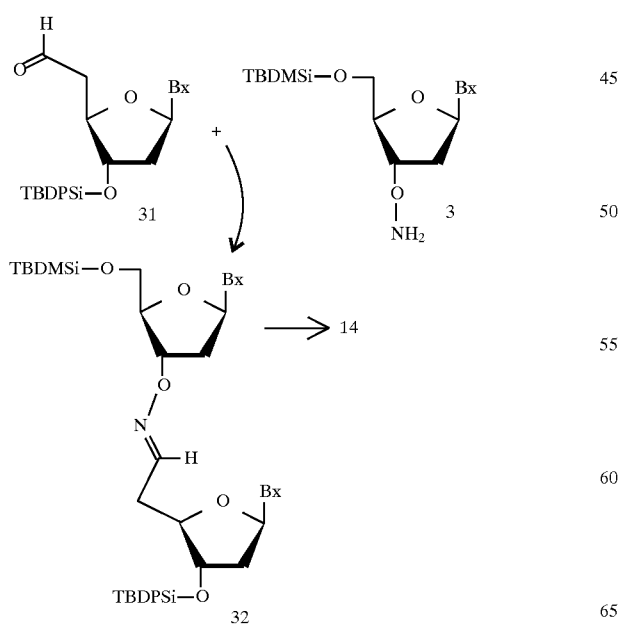
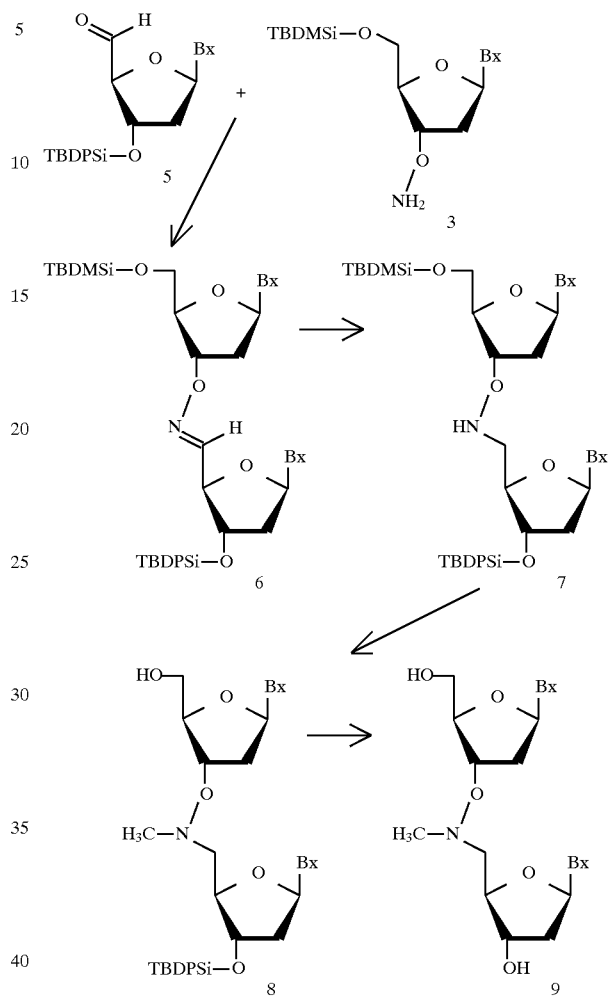

SCHEME IX
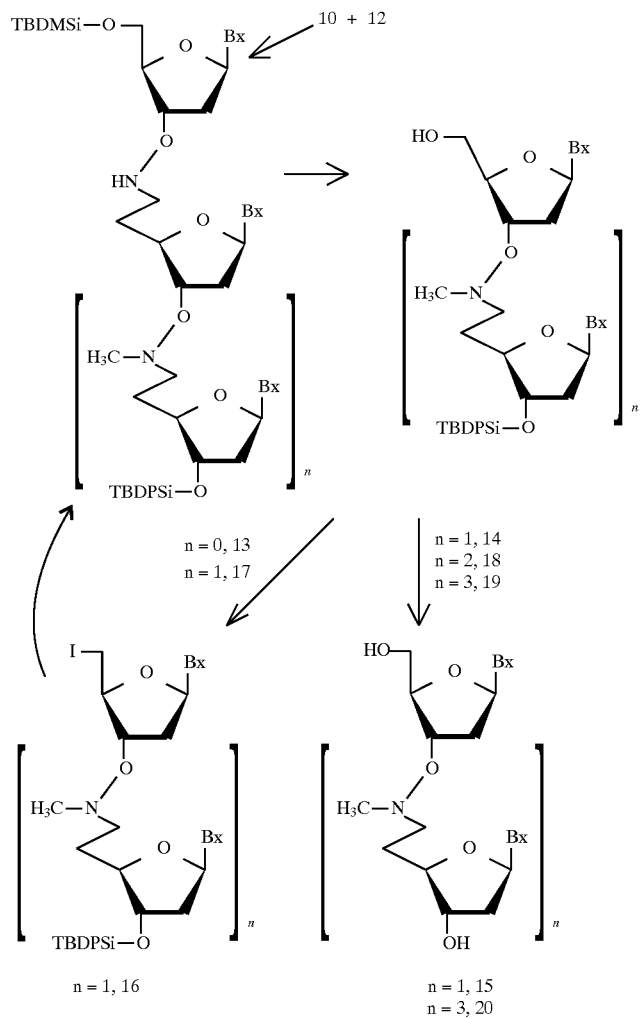

19
SCHEME X
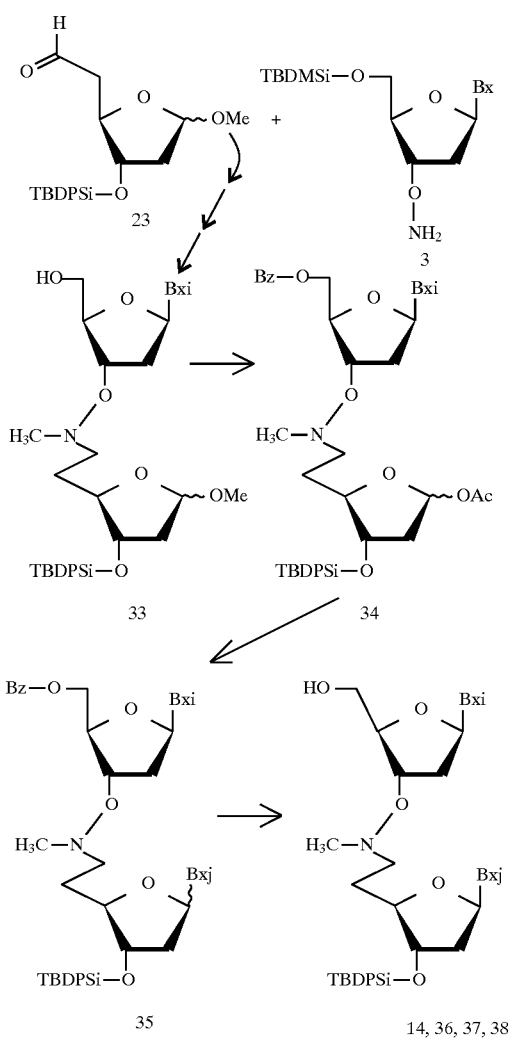
SCHEME XI
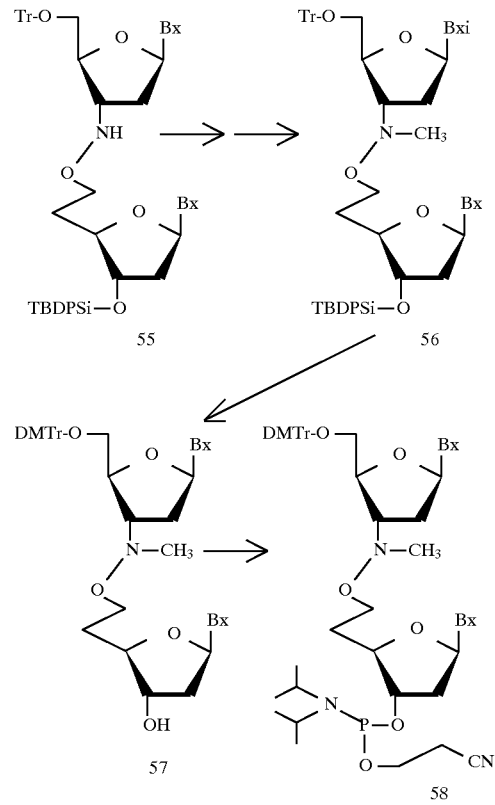
20
-continued
SCHEME XI
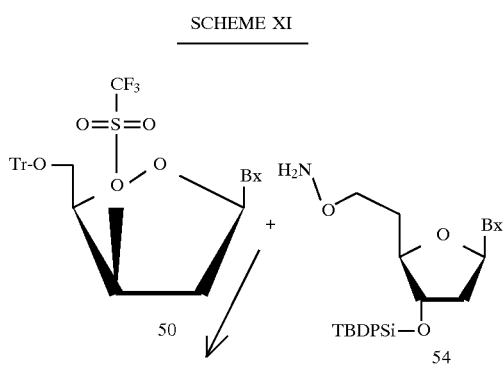
SCHEME XII
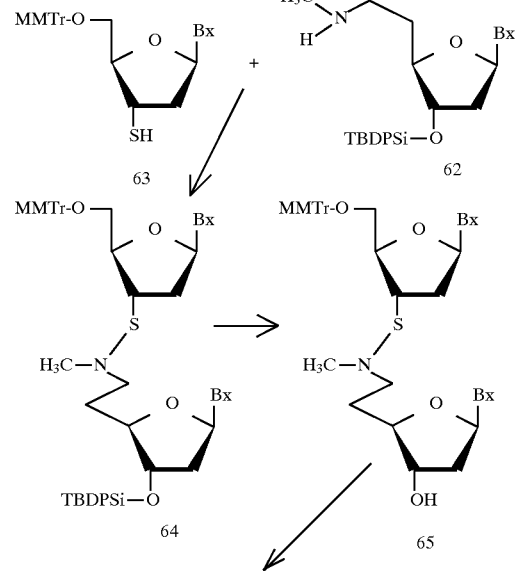

-continued
SCHEME XII
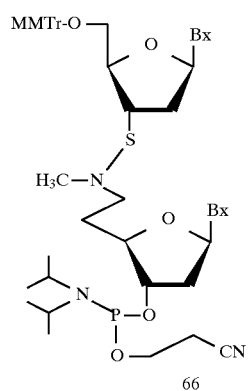
66
SCHEME XIV
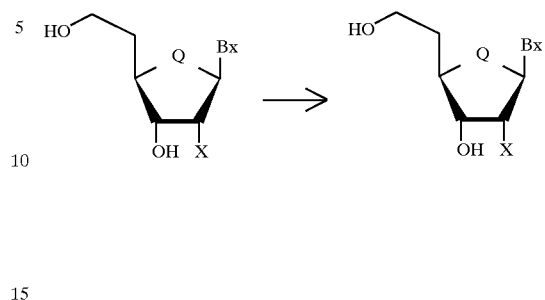
SCHEME XIII
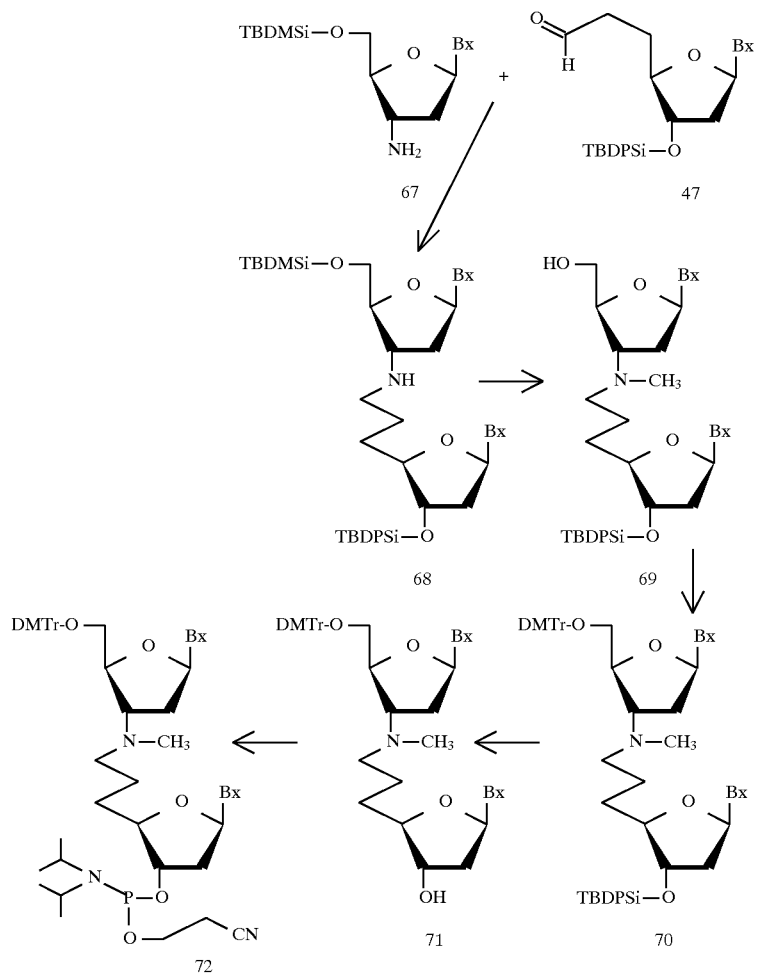

SCHEME XIV
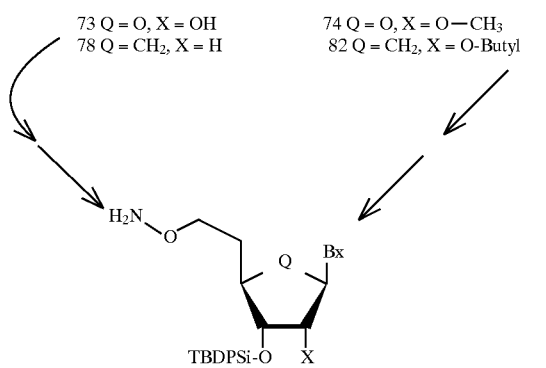
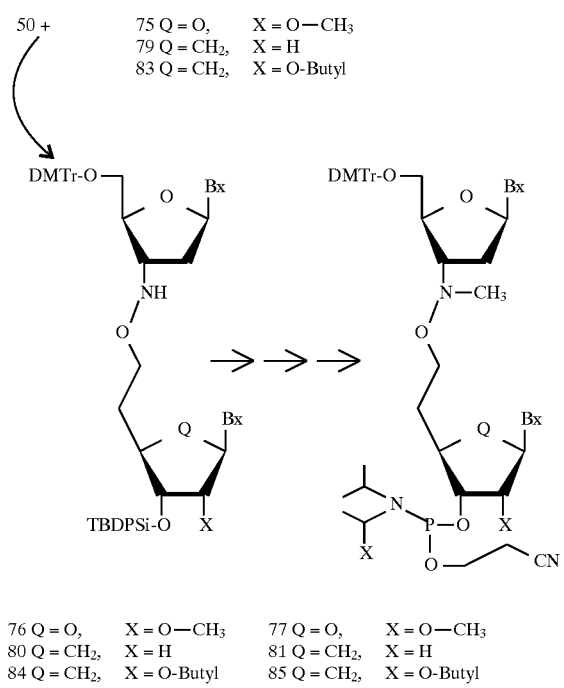
SCHEME XV
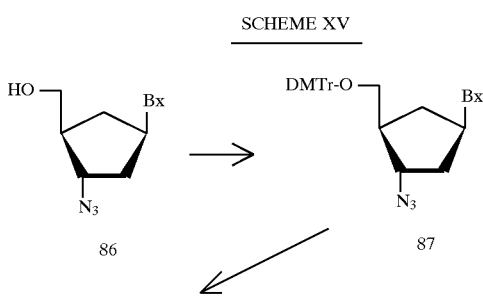
SCHEME XV -continued
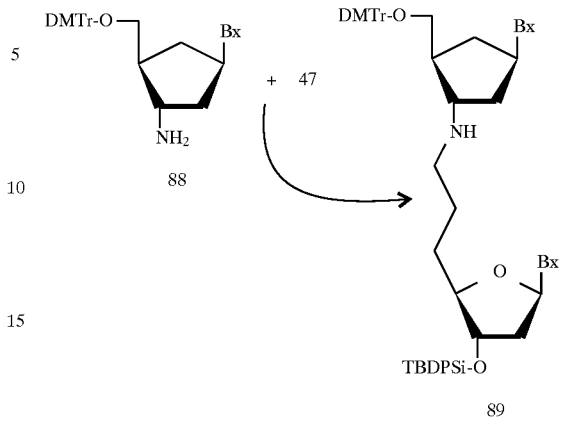
SCHEME XVI
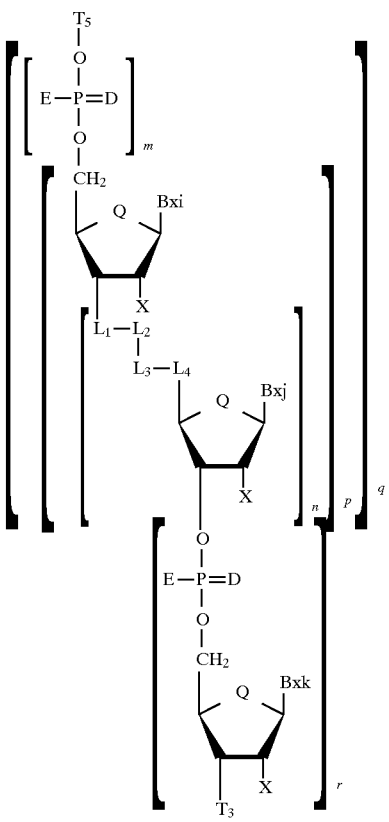
The compounds of this invention can be used in diagnostics, therapeutics, and as research reagents and kits. For therapeutic use the oligonucleotide analog is administered to an animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

It is preferred that the RNA or DNA portion which is to be modulated be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

In accordance with one preferred embodiment of this invention, the compounds of the invention hybridize to HIV mRNA encoding the tat protein, or to the TAR region of HIV mRNA. In another preferred embodiment, the compounds mimic the secondary structure of the TAR region of HIV mRNA, and by doing so bind the tat protein. Other preferred compounds complementary sequences for herpes, papilloma and other viruses.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

This invention is also directed to methods for the selective binding of RNA for research and diagnostic purposes. Such selective, strong binding is accomplished by interacting such RNA or DNA with compositions of the invention which are resistant to degradative nucleases and which hybridize more strongly and with greater fidelity than known oligonucleotides or oligonucleotide analogs.

Additional objects, advantages, and novel features of this invention will become apparent to those skilled in the art upon examination of the following examples thereof, which are not intended to be limiting, wherein parts and percents are by weight unless otherwise indicated. For NMR analysis of dimers and other higher oligonucleosides, monomeric units are numbered (e.g., $T_1$, $T_2$) from the 5' terminus towards the 3' terminus nucleoside. Thus, the 5' nucleoside of a T-T dimer is $T_1$ and the 3' nucleoside is $T_2$.

EXAMPLE 1
Synthesis of 5'-deoxy-5'-hydrazino nucleosides
(a) 5'-Deoxy-5'-hydrazinothymidine hydrochloride To provide 5'-benzylcarbazyl-5'-deoxythymidine, 5'-O-tosylthymidine, [*Nucleosides & Nucleotides* 1990, 9, 89] (1.98 g, 5 mmol), benzylcarbazide (4.15 g, 25 mmol), activated molecular sieves (3A, 2 g), and anhydrous dimethylacetamide (100 ml) were stirred together with exclusion of moisture at 110° C. (bath temperature) for 16 hours. The products were cooled and concentrated under reduced pressure (bath temperature<50° C.). The residue was purified on a silica gel column (5×45 cm) with $CH_2Cl_2$/MeOH (9:1, v/v) as the solvent. The homogeneous fractions were pooled, evaporated to dryness and the foam recrystallized from EtOH to yield 0.7 g (36%) of 5'-benzylcarbazyl-5'-deoxythymidine; mp 201° C.; $^1$H NMR ($Me_2SO$-$d_6$) δ 1.79 (s, 3, $CH_3$), 2.00–2.18 (m, 2, $C_2,CH_2$), 2.95 (t, 2, $C_5,CH_2$), 3.75 (m, 1, $C_4,H$), 4.18 (m, 1, $C_3,H$), 4.7 (brs, 1, $O'_2NH$), 5.03 (s, 2, $PhCH_2$), 5.2 (d, 1, $C_3,H$), 6.16 (t, 1, $C_1,H$), 7.2–7.4 (m, 5, $C_6H_5$), 7.6 (s, 1, $C_6H$), 8.7 (brs, 1, $CH_2NH$), 11.2 (brs, 1, $C_3NH$).

To provide the hydrochloride salt of 5'-deoxy-5'-hydrazinothymidine as a hygroscopic powder, a mixture of the above carbazate (0.78 g, 2 mmol) and palladium on charcoal (10%, 150 mg) in anhydrous MeOH/HCl (30 ml, 2%, HCl by weight) was stirred under an atmosphere of hydrogen at room temperature for 1.5 hours. The methanolic solution was filtered through Celite to remove the catalyst. The filter cake was washed with EtOH (2×25 ml). The filtrate was concentrated under vacuum and the residue was dried overnight to remove traces of HCl. The yellow residue was dissolved in methanol (3 ml) and added dropwise to a rapidly stirred solution of ethyl acetate (150 ml). The filtered precipitate was washed with ethyl acetate (3×100 ml) and the pale yellow solid was dried under vacuum to yield 0.51 g (88%) of 5'-deoxy-5'-hydrazinothymidine hydrochloride (hygroscopic powder); $^1$H NMR ($Me_2SO$-$d_6$) δ 1.81 (s, 3, $CH_3$), 2.02–2.22 (m, 2, $C_2,CH_2$), 3.2 (m, 2, $C_5,CH_2$), 3.8, (m, 1, $C_4,H$), 4.2 (m, 1, $C_3,H$), 6.17 (t, 1, $C_1,H$), 7.54 (s, 1, $C_6H$), 11.18 (brs, 1, $C_3NH$), the hydrazino and 3'-OH were masked by $H_2O$.

EXAMPLE 2
Synthesis of 5'-O-trityl-1-[2,3-dideoxy-3-C-(formyl)-β-D-erythro-pentofuranosyl]-thymine and -uracil
Method A
3'-C-Cyano-3'-deoxy-5'-O-tritylthymidine The following preparation should to be performed under a hood and all precautions taken not to inhale any of reagent fumes. A suspension of 3'-deoxy-3'-iodo-5'-O-tritylthymidine (Verheyden, et al., *J. Org. Chem.* 1970, 35, 2868) (60 g, 0.1 mol), hexamethylditin (36 g, 22.7 ml, 0.11 mol), t-butylisocyanide (166 g, 225 ml, 2 mol), and AIBN (1.6 g, 10 mmol) in toluene (freshly distilled over Na/benzophenone, 2 lt) was thoroughly deoxygenated by bubbling argon through the reaction mixture for 30 min. and then heated at 80° C. for 13 h. The reaction mixture was cooled at 60° C. and AIBN (1.6 g, 10 mmol) was added and heating continued for 24 h. During this period addition of AIBN was repeated for 3 times in an identical manner. The reaction mixture was cooled to room temperature and transferred on the top of a prepacked silica gel column (1.5 kg, in hexanes) and eluted with hexanes: $Et_2O$ (100% hexanes→100% $Et_2O$ with a 10% gradient change each time using 1 lt of eluent). Most of the impurities were removed during the gradient elution as non-polar compounds. Final elution with $Et_2O$ (2 lt), pooling and evaporation of appropriate fractions gave two compounds in the order these were collected. (i) 12.93 g (25%) of 3'-C-Cyano-3'-deoxy-5'-O-tritylthymidine as white powder (crystallized from toluene/$Et_2O$, mp 153°–157° C.); $^1$H NMR ($CDCl_3$) δ 8.83 (s, 1, NH), 7.04–7.4 (m, 18.5, TrH, $C_6H$, and 0.5 ArH from toluene), 6.10 (dd, 1, $H_1$, $J_{1',2''}$=4.1 Hz, $J_{1',2''}$=7.1 Hz), 4.20 (m, 1, $H_4$, $J_{3',4'}$=8.4 Hz, $J_{4',5'}$=2.8 Hz), 3.33–3.60(m, 3, $H_{5',5'',3'}$), 2.68 (m, 1, $H_{2'}$, $J_{2',2''}$=13.8 Hz), 2.52 (m, 1, $H_{2''}$), 2.28 (s, 1.5, 0.5 $CH_3$ from toluene), and 1.50 (s, 3, $CH_3$). Anal. Calcd. for $C_{30}H_{27}N_3O_4 \cdot 0.5\ C_7H_8$ (toluene from crystallization): C, 74.56; H, 5.79; N, 7.78. Found: C, 74.27; H, 5.78; N, 7.66.

The reaction mixture also gave 4.82 g, (10%) of 1-(3'-C-cyano-2',3'-dideoxy-5'-O-trityl-β-D-threopentofuranosyl) thymine; $^1$H NMR ($CDCl_3$) δ 8.72 (s, 1, NH), 7.03–7.44 (m, 18.5, TrH, $C_6H$, and 0.5 ArH from toluene), 6.13 (pseudo t, 1, $H_1$, $J_{1',2''}$=6.7 Hz, $J_{1',2''}$=5.7 Hz), 4.09 (m, 1, $H_4$, $J_{3',4'}$=6.7 Hz, $J_{4',5'}$=4.9 Hz), 3.56 (m, 2, $H_{5',5''}$, 3.28 (m, 1, $H_3$, $J_{3',2''}$=8.2 Hz, $J_{3',2''}$=5.2 Hz), 2.70 (m, 1, $H_{2',2''}$=14 Hz), 2.28 (s, 1.5, $CH_3$ from toluene) and 1.60 (s, 3, $CH_3$). Anal. Calcd. for $C_{30}H_{27}N_3O_4 \cdot 0.5\ C_7H_8$ (toluene from crystallization): C, 74.56; H, 5.79; N, 7.78. Found: C, 74.10; H, 5.74; N, 7.52.

Epimerization: To a suspension of 1-(3'-C-Cyano-2',3'-dideoxy-5'-O-trityl-β-D-threo-pentofuranosyl)thymine (0.30 g, 0.61 mmol) in methanol (20 ml) was added dropwise a 1N solution of NaOMe until the pH of solution reached≈9. The resulting mixture was heated to reflux for 20 h. The solution was cooled (0° C.) and neutralized with 1N HCl/MeOH and evaporated under reduced pressure. The residue was purified as described above to furnish 0.185 g (62%) of 3'-C-cyano-3'-deoxy-5'-O-tritylthymidine. (A synthesis for 3'-deoxy-3'-C-cyano-5'-O-tritylthymine was reported in *Tetrahedron Letters* 1988, 29, 2995. This report suggested 3'-deoxy-3'-C-cyano-5'-O-tritylthymine is formed as a single product, however, we found a mixture of threo- and erythro-3'-cyano isomers are produced. (see, Bankston, et al., *J. Het. Chem.* 1992, 29, 1405. By the above epimerization, the xylo component of this mixture is converted to the compound of interest, 3'-deoxy-3'-C-cyano-5'-O-tritylthymine.)

3'-Deoxy-3'-C-formyl-5'-O-tritylthymine

DIBAL-H (1M in toluene, 50 ml, in 5 portions over a period of 5 h) was added to a stirred solution of 3'-C-cyano-3'-deoxy-5'-O-tritylthymidine (9.92 g, 20 mmol) in dry THF (10 ml) under argon at 0° C. The solution was stirred at room temperature for 1 h and cooled again to 0° C. MeOH (25 ml) was added dropwise to the cold solution while stirring and after complete addition the solution was brought to room temperature. A saturated aqueous $Na_2SO_4$ solution (11 ml) was added to the reaction mixture and stirred for 12 h. Powdered anhydrous $Na_2SO_4$ (30 g) was added to the reaction mixture and suspension was stirred for 30 min. The suspension was filtered and residue was thoroughly washed with MeOH:$CH_2Cl_2$ (1:9 v/v) until all of the product was washed off. The filtrates were combined and concentrated under vacuum, to furnish a gummy residue. The residue was purified by silica gel chromatography using $CH_2Cl_2$:MeOH (100% $CH_2Cl_2\rightarrow$9:1, v/v) for elution to obtain 5.45 g (55%) of 3'-deoxy-3'-C-formyl-5'-O-tritylthymine as a white foam. $^1$H NMR ($CDCl_3$) δ 9.61 (d, 1, CHO, $J_{3',3''}$=1.5 Hz), 8.44 (s, 1, NH), 7.46 (s, 1, $C_6H$), 7.17–7.45 (m, 15, TrH), 6.04 (pseudo t, 1, $H_1'$, $J_{1',2'}$=5.3 Hz, $J_{1',2''}$=6.6 Hz), 4.31 (m, 1, $H_4'$, $J_{4',5'}$=3.3 Hz, $J_{3',4'}$=7 Hz), 3.28–3.55 (m, 3, $H_{5',5'',3'}$), 2.69 (m, 1, $H_2'$), 2.28 (m, 1, $H_{2''}$), 1.48 (s, 3, $CH_3$). Anal. Calcd. for $C_{30}H_{28}N_2O_5H_2O$: C, 70.03; H, 5.88; N, 5.44. Found: C, 70.40; H, 6.00; N, 5.33.

1-[3-Deoxy-3-C-(formyl)-5-O-trityl-β-D-erythropentofuranasyl]uracil

To a stirred solution of 3'-cyano-2',3'-dideoxy-5'-O-trityluridine (0.96 g, 2 mmol), (prepared in a manner equivalent to that of the thymidine analog above) in dry THF (20 ml) under argon, was added a solution of DIBAL-H in toluene (Aldrich) (1M, 4 ml) at −10° C. over a period of 10 min. After 30 mins the reaction was quenched with MeOH (5 ml) at −10° C. The mixture was further stirred at ambient temperature for 30 mins and diluted with $CH_2Cl_2$ (25 ml) before concentrating under vacuum. This process was repeated with $CH_2Cl_2$ (3×25 ml) in order to remove the residual THF. The residue was purified by flash chromatography on silica gel (25 g). Elution with $CH_2Cl_2$ (9:1, v/v) and crystallization from $CH_2Cl_2$/MeOH gave 5'-O-trityl-3'-C-formyl-2',3'-dideoxyuridine (0.53 g, 53%); mp 100° C.; $^1$H NMR ($CDCl_3$) δ 2.25–2.8 (m, 2, $CH_2$), 3.4 (m, 1, $C_3H$), 3.45–3.6 (m, 2, $C_5,CH_2$), 4.37 (m, 1, $C_4,H$), 5.4 (d, 1, $C_5H$), 6.1 (m, 1, $C_1,H$), 7.2–7.4 (m, 15, $C_6H_5$), 7.81 (d, 1, $C_6H$), 7.95 (br s, 1, NH), 9.61 (s, 1, HC=O).

Method B

1-[3-deoxy-3-C-(formyl)-5-O-trityl-β-D-erythropentofuranosyl]thymine

1-Methyl-5-O-(t-butyldiphenylsilyl)-2,3-dideoxy-3-C-(formyl)-D-erythro-pentofuranose was obtained as an oil in 90% yield using the DIBAL-H reduction of 1-methyl-5-(t-butyldiphenylsilyl)-2,3-dideoxy-3-C-cyano-D-erythro-pentofuranose as described in *Tetrahedron* 1900, 44, 625. The 3-C-formyl group is derivatized to the oxime with methoxyamine. The oxime blocked intermediate was glycosylated with silyated thymine to give an α and β mixture of the title compound. After deblocking, the β anomer compares to that prepared via method A.

Method C

1-[3-deoxy-3-C-(formyl)-5-O-trityl-β-D-erythropentofuranosyl]-uracil and -thymine A mixture of 3'-deoxy-3'-iodo-5'-O-tritylthymidine (0.59 g, 4 mmol), tris(trimethylsilyl) silane (2.87 g, 1.2 mmol), AIBN (12 mg, 0.072 mmol), and toluene (20 ml) were mixed in a glass container and saturated with argon (bubbling at room temperature). The glass vessel was inserted into a stainless steel pressure reactor, and pressurized with carbon monoxide (80 psi), closed and heated (90° C., bath) for 26 hrs. The reaction mixture was cooled (0° C.) and the CO was allowed to escape carefully (under the fume hood). The product was purified by flash column chromatography on silica gel (20 g). Elution with EtOAc:Hexanes (2:1, v/v) and pooling the appropriate fractions furnished 0.30 g (61%) of the title compound as a foam.

A radical carbonylation of 2',3'-dideoxy-3'-iodo-5'-trityluridine in a similar manner gives the 3'-C-formyl uridine derivative.

EXAMPLE 3

Synthesis of methylenehydrazone linked (3'-CH=NH—NH—$CH_2$-5'), methylenehydrazine linked (3'-$CH_2$—NH—NH—$CH_2$-5') and methylene(dimethylhydrazo) linked (3'-$CH_2$—N($CH_3$)—N($CH_3$)—$CH_2$-5') dinucleosides 3'-De(oxyphosphinico)-3'-[methylene(hydrazone)]-5'-O-tritylthymidylyl-(3'→5')-5'-deoxythymidine A mixture of 3'-deoxy-3'-C-formyl-5'-O-tritylthymidine, 0.645 g, 1.30 mmol, 5'-deoxy-5'-hydrazinothymidine hydrochloride (0.397 g, 1.36 mmol) in dry $CH_2Cl_2$/MeOH/AcOH (20 ml/ 10 ml/0.5 ml) was stirred for 30 min at room temperature. The solvent was evaporated under vacuum and the hydrazone intermediate was analyzed by $^1$H NMR (DMSO-$d_6$) δ1.1 (br s, 2 NH), 8.3 (s, 1, C=N—NH), 7.5–7.74 (m, 17, Tr H, $2C_6H$), 6.8 (1d, 1t, 1, HC=N, two isomers), 6.0–6.1 (2m, 2, $H_1'$,), 5.30 (br t, 1, OH), 3.8–4.2 (3m, 3, $H_3'$, 2 $H_4'$) 3.0–3.3 (m, 5, $2H_{5',5''}$, $H_3'$), 2.0–2.4 (m, 4, $2H_{2',2'}$), 1.5 and 1.7 (2s, 6, 2 $CH_3$).

3'-De(oxyphosphinico)-3'-[methylene(dimethylhydrazo)]-5'-O-tritylthymidylyl-(3'→5')-5'-deoxythymidine The above hydrazone dimer was dissolved in AcOH (10 ml) and to this was added small portions of $NaBH_3CN$ (4×0.12 g, 7.74 mmol) while stirring at room temperature for 30 min. The solution was stirred for an additional 15 min before the addition of aqueous HCHO (20%, 3.9 ml, 26 mmol), $NaBH_3CN$ (3.9 mmol), and AcOH (10 ml). The suspension was further stirred for 15 min. and solution evaporated under vacuum. The residue was coevaporated with MeOH (3×25 ml) to give the methylenehydrazo dimer; $^1$H NMR ($CDCl_3$) δ 6.8–7.8 (m, 15, TrH, 2 $C_6H$), 6.12 (m, 2, $2H_1'$), 4.20 ((m, 1, T2 $H_3'$), 4.05 (m, 1, T2 $H_4'$), 3.89 (m, 1, T1 $H_4'$), 3.80 (s, 6, 2 $OCH_3$), 3.21–3.53 (m, 2, T1 $H_{5',5''}$), 2.11–2.75 (m, 10, T2 $H_{5'5''}$H, T1 $H_3'$, T1 $H_3'$, T1 T2 $H_{2'2''}$), 2.26 (s, 6, 2N—$CH_3$), 1.88 and 1.49 (2s, 6, 2 $CH_3$), and other protons.

3'-De(oxyphosphinico)-3'-[methylene(dimethylhydrazo)]-thymidylyl-(3'→5')-5'-deoxythymidine The above hydrazine dimer was then stirred with 37% aqueous HCl (1 ml) in MeOH (25 ml) at room temperature for 24 h. The resulting mixture was neutralized with $NH_4OH$ (pH≈8) and evaporated to dryness. The residue was purified by reverse phase HPLC (supelcosil LC18, 5 m, H$_2$O: CH$_3$CN gradient) to furnish 0.61 g of the title methylene (dimethylhydrazine) linked dimer (89%). $^1$H NMR (90° C., DMSO-d$_6$+1 drop of D$_2$O) δ7.66 and 7.43 (2s, 2, 2 C6$\underline{H}$), 6.02 (pseudo t, 1, T2 $\underline{H}_{1'}$, J$_{1',2'}$=7.2 Hz, J$_{1',2''}$=7.7 Hz), 5.96 (pseudo t, 1, T1 $\underline{H}_{1'}$, J$_{1',2'}$=5.6 Hz, J$_{1',2''}$=6.2 Hz), 4.12 (m, 1, T2 $\underline{H}_{3'}$), 3.90 (m, 1, T2 $\underline{H}_{4'}$), 3.71 (m, 1, T1 $\underline{H}_{4'}$), 3.61 (m, 2, T1 $\underline{H}_{5',5''}$), 2.4–2.8 (m, 5, T2 $\underline{H}_{5',5''}$, T1 $\underline{H}_{3''}$, T1 $\underline{H}_{3'}$), 2.29 (2s, 6, 2 N→C$\underline{H}_3$), 2.12 (m, 4, 2$\underline{H}_{2',2''}$), 1.76 and 1.74 (2s, 6, 2 C$\underline{H}_3$). Anal. Calcd. for C$_{23}$H$_{34}$N$_6$O$_8$,H$_2$O: C, 51.10, H, 6.71; N, 15.54. Found: C, 51.05; H, 6.68; N, 15.54. MS FAB m/z 523 (M+H)$^+$.

EXAMPLE 4
Synthesis of methylene(dimethylhydrazine) linked (3'-CH$_2$—N(CH$_3$)—N(CH$_3$)—CH$_2$-5') 5'-dimethoxytrityl-3'-β-cyanoethoxydiisopropylphosphoramidite dinucleosides 3'-De(oxyphosphinico)-3'-[methylene(dimethylhydrazo)]-thymidylyl-5'-O-(dimethoxytriphenylmethyl)-(3'→5')-3'-O-(β-cyanoethyl-N-diisoproppylaminophosphiryl)thymidine The methylene(dimethylhydrazine) dimer of Example 3 was dimethyoxytritylated following the standard procedure described in Oligonucleotide Synthesis: a practical approach, Ed. M. J. Gait, IRL Press, 1984, to furnish a homogenous foam $^1$H NMR (CDCl$_3$) δ 6.8–7.8 (m, 20, DMTr, 2$\underline{H}_6$), 6.12 (m, 2, 2$\underline{H}_{1'}$), 4.20 (m, 1, T$_2$ $\underline{H}_{3'}$), 4.05 (m, 1, T$_2$ $\underline{H}_{4'}$), 3.89 (m, 1, T$_1$ $\underline{H}_{4'}$), 3.80 (s, 6, 2 OC$\underline{H}_3$ of DMTr), 3.21–3.53 (m, 2, T$_1$ $\underline{H}_{5'5''}$), 2.11–2.75 (m, 9, T$_1$ $\underline{H}_{5'5''}$, $\underline{H}_{3''}$, T$_1$ $\underline{H}_{3'}$, 2$\underline{H}_{2'2''}$), 2.26 (2s, 6, 2 N—C$\underline{H}_3$) and 1.88 and 1.49 (2s, 2, C$_5$ C$\underline{H}_3$)] which on phosphitylation via the procedure described in Oligonucleotide Synthesis: a practical approach, Ed. M. J. Gait, IRL Press, 1984, provided a 65% yield of the title compound. $^1$H NMR (CDCl$_3$) δ 6.14 (m, 1, T2 $\underline{H}_{1'}$), 6.01 (m, 1, T1 $\underline{H}_{1'}$), 3.80 (s, 6, 2 O C$\underline{H}_3$), 2.23 (m, 6, 2 N—C$\underline{H}_3$), 1.78 and 1.45 (2s, 6, 2 C$\underline{H}_3$), and other protons. $^{31}$P NMR (CDCl$_3$) δ 149.43 and 148.85 ppm.

EXAMPLE 5
Synthesis of intermittent methylene(dimethyhydrazine) (3'-CH$_2$—NCH$_3$—NCH$_3$—CH$_2$-5') linked oligonucleosides CPG-bound thymidine (or any other nucleoside that is to become the 3'-terminal base) was placed in an Applied Biosystems, Inc. (ABI) column (250 mg, 10 micromoles of bound nucleoside) and attached to an ABI 380B automated DNA Synthesizer. The standard, automated (computer controlled) steps utilizing phosphoramidite chemistries are employed to place the methylenehydrazine thymidine dimer into the sequence at any desired location.

EXAMPLE 6
Synthesis of 5'-O-phthalimido nucleosides 5'-O-Phthalimidothymidine To a stirred solution of thymidine (24.22 g, 0.1 mol), N-hydroxyphthalimide (21.75 g, 0.13 mol), triphenylphosphine (34 g, 0.13 mol) in dry DMF (400 ml) was added diisopropylazodicarboxylate (30 ml, 0.15 mol) over a period of 3 h at 0° C. After complete addition the reaction mixture was warmed up to room temperature and stirred for 12 h. The solution was concentrated under vacuum (0.1 mm, <40° C.) to furnish an orange-red residue. The residual gum was washed several times with Et$_2$O and washing were discarded. The semi-solid residue was suspended in EtOH (500 ml) and heated (90° C.) to dissolve the product. On cooling 30.98 g (80%) of 5'-O-phthalimidothymidine was collected in 3-crops as white crystalline material, mp 233°–235° C. (decomp.); $^1$H NMR (DMSO-d$_6$) δ 11.29 (s, 1, N$\underline{H}$), 7.85 (m, 4, Ar$\underline{H}$), 7.58 (s, 1, C$_6\underline{H}$), 6.20 (t, 1, $\underline{H}_{1'}$, J$_{1',2'}$=7.8 Hz, J$_{1',2''}$=6.5 Hz), 5.48 (d, 1, O$\underline{H}_3$), 4.36 (m, 3, $\underline{H}_{4',5',5''}$), 4.08 (m, 1, $\underline{H}_{3'}$), 2.09–2.13 (m, 2, $\underline{H}_{2',2''}$), and 1.79 (s, 3, C$\underline{H}_3$). Anal. Calcd. for C$_{18}$H$_{17}$O$_7$N$_3$.0.7 H$_2$O: C, 54.05; H, 4.64; N, 10.51. Found: C, 53.81; H, 4.25; N, 10.39.

2'-deoxy-5'-O-phthalimidouridine

An analogous reaction on 2'-deoxyuridine gave the corresponding 2'-deoxy-5'-$\underline{O}$-phthalimidouridine; mp 241°–242° C.

EXAMPLE 7
Synthesis of 5'-O-phthalimido-3'-O-(t-butyldiphenylsilyl) thymidine and 2'-deoxy-5'-O-phthalimido-3'-O-(t-butyldiphenylsilyl)uridine 3'-O-(t-butyldiphenylsilyl)-5'-O-phthalimidothymidine A mixture of 5'-$\underline{O}$-phthalimidothymidine (8.54 g, 22 mmol), t-butyldiphenylsilylchloride (6.9 ml, 26.5 mmol), imidazole (3.9 g, 57.3 mmol) and dry DMF (130 ml) was stirred at room temperature for 16 h under argon. The reaction mixture was poured into ice-water (600 ml) and the solution was extracted with CH$_2$Cl$_2$ (2×400 ml). The organic layer was washed with water (2×250 ml) and dried (MgSO$_4$). The CH$_2$Cl$_2$ layer was concentrated to furnish a gummy residue which on purification by silica gel chromatography (eluted with EtOAc:Hexanes; 1:1, v/v) furnished 12.65 g (92%) of 3'-$\underline{O}$-(t-butyldiphenylsilyl)-5'-$\underline{O}$-phthalimidothymidine as crystalline material (mp 172°–173.5° C.). $^1$M NMR (DMSO-d$_6$) δ 11.31 (s, 1, N$\underline{H}$), 7.83 (m, 4, Ar$\underline{H}$), 7.59 (m, 4, TBDPh$\underline{H}$), 7.51 (s, 1, C$_6\underline{H}$), 7.37–7.45 (m, 6, TBDPh$\underline{H}$), 6.30 (dd, 1, $\underline{H}_{1'}$, J$_{1',2'}$=8.8 Hz, J$_{1',2''}$=5.6 Hz), 4.55 (m, 1, $\underline{H}_{4'}$), 4.15 (m, 1, $\underline{H}_{3'}$), 3.94–4.04 (m, 2, $\underline{H}_{5',5''}$), 2.06–2.13 (m, 2, $\underline{H}_{2',2''}$), 1.97 (s, 3, C$\underline{H}_3$), 1.03 (s, 9, C(C$\underline{H}_3$)$_3$). Anal. Calcd. for C$_{34}$H$_{35}$O$_7$N$_3$Si: C, 65.26; H, 5.64; N, 6.71. Found: C, 65.00; H, 5.60; N, 6.42.

3'-O-(t-butyldiphenylsilyl)-2'-deoxy-5'-O-phthalimidouridine

An analogous reaction of 2'-deoxy-5'-$\underline{O}$-phthalimidouridine will give the corresponding 3'-$\underline{O}$-(t-butyldiphenylsilyl)-2'-deoxy-5'-$\underline{O}$-phthalimidouridine.

EXAMPLE 8
Synthesis of 5'-O-amino nucleoside
5'-O-amino-3'-O-(t-butyldiphenylsilyl)thymidine To a stirred solution of 3'-$\underline{O}$-(t-butyldiphenylsilyl)-5'-$\underline{O}$-phthalimidothymidine (10 g, 16 mmol) in dry CH$_2$Cl$_2$ (100 ml) was added methylhydrazine (1.3 ml, 24 mmol) under argon at room temperature and solution stirred for 12 h. The solution was cooled (0° C.) and filtered. The white residue was washed with CH$_2$Cl$_2$ (2×25 ml) and combined filtrates were evaporated to furnish gummy residue. The residue on purification by silica gel column chromatography (elution with CH$_2$Cl$_2$:MeOH, 98:2, v/v) furnished 7.03 g (89%) of 5'-O-amino-3'-$\underline{O}$-(t-butyldiphenylsilyl)thymidine that crystallized from CH$_2$Cl$_2$/MeOH mp 141°–143° C. $^1$H NMR (DMSO-d$_6$) δ 11.29 (s, 1, N$\underline{H}$), 7.42–7.62 (m, 11, TBDPh$\underline{H}$, C$_6$ $\underline{H}$), 6.25 (dd, 1, $\underline{H}_{1'}$, J$_{1',2'}$=8.4 Hz, J$_{1'2''}$=6.3 Hz), 6.02 (s, 2, N$\underline{H}_2$), 4.35 (m, 1, $\underline{H}_{4'}$), 4.04 (m, 1, $\underline{H}_{3'}$), 3.34–3.51 (m, 2, $\underline{H}_{5',5''}$), 2.04 (m, 2, $\underline{H}_{2',2''}$) 1.73 (s, 3, C$\underline{H}_3$), 1.03 (s, 9, C(C$\underline{H}_3$)$_3$). Anal. Calcd. for C$_{26}$H$_{33}$O$_5$N$_3$Si: C, 63.00; H, 6.71; N, 8.48. Found: C, 62.85; H, 6.67; N, 8.32.

EXAMPLE 9
Synthesis of (3'-CH=N—O—CH$_2$-5') linked oligonucleoside (an oxime linked dimer)

3'-De(oxyphosphinico)-3'-(methylidynenitrilo)-thymidylyl-(3'→5')-thymidine

A mixture of 3'-deoxy-3'-C-formyl-5'-O-tritylthymine (0.99 g, 2 mmol), 5'-amino-3'-$\underline{O}$-(t-butyldiphenylsilyl) thymidine (0.99 g, 2 mmol) and AcOH (0.3 ml) in dry CH$_2$Cl$_2$ (20 ml) was stirred for 1 h at room temperature. The solvent was evaporated under vacuum and the crude blocked 3'-de(oxyphosphinico)-3'-(methylidynenitrilo)thymidylyl-(3'→5')-3'-(t-butyldiphenylsilyl)thymidine product was dissolved in THF (20 ml). A THF solution of nBu$_4$NF (1M, 5 ml) was added to the stirred reaction mixture at room temperature. After 1 h solution was purified by silica gel chromatography (elution with CH$_2$Cl$_2$:MeOH; 99:4, v/v) to furnish 3'-deblocked dimer. The dimer was dissolved in anhydrous MeOH (50 ml) and to this a MeOH/HCl solution (0.14M, 2.5 ml) was added. The reaction mixture was stirred at room temperature for 15 h. Anhydrous pyridine (10 ml) was added to the above solution and solvents were evaporated to dryness to furnish crude oxime dimer. The crude product was purified by silica gel chromatography (elution with CH$_2$Cl$_2$:MeOH; 92:8, v/v) to furnish the title compound, 3'-De(oxyphosphinico)-3'-(methylidynenitrilo) thymidylyl-(3'→5')-thymidine, (0.87 g, 89%) as a mixture of E/Z isomers. The two geometrical isomers were separated by reverse phase HPLC (Supelcosil LC18, 5μ, H$_2$O:CH$_3$CN gradient). (Z-isomer of title compound) $^1$H NMR (DMSO-d$_6$) δ 11.28 (br s, 2, 2NH), 7.39 and 7.78 (2s, 2, 2C6H), 6.92 (d, 1, T1 H$_{3''}$, J$_{3',3''}$=6.7 Hz), 6.15 (pseudo t, 1, T2 H$_{1'}$, J$_{1',2'}$=7.8 Hz, J$_{1',2''}$=6.3 Hz), 6.04 (dd 1, T1 H$_{1'}$, J$_{1',2''}$=7.1 Hz, J$_{1',2''}$=6.3 Hz), 5.34 (d, 1, T2 OH), 5.12 (t, 1, T1 OH), 4.11–4.25 (m, 3, T2 H$_{5',5''}$, T2 H$_{3'}$) 3.96 (m, 1, T2 H$_{4'}$), 3.90 (m, 1, T1 H$_{4'}$), 3.49–3.69 (m, 3, T1 H$_{5',5''}$, T1 H$_{3'}$), 2.06–2.31 (m,4, T1 H$_{2',2''}$, T2 H$_{2',2''}$), 1.73 (s, 6, 2CH$_3$). Anal. Calcd. for C$_{21}$H$_{27}$N$_5$O$_9$.H$_2$O: C, 49.31; H, 5.72; N, 13.69. Found: C, 49.32; 5.57; N, 13.59. (E-isomer of the title compound) $^1$H NMR (DMSO-d$_6$) δ 11.3 (2 br s, 2, 2NH), 7.81 (s, 1, C$_6$H), 7.52 (d, 1, T1 H$_{3''}$, J$_{3',3''}$=6.7 Hz), 7.45 (s, 1, C$_6$H), 6.10 (pseudo t, 1, T2 H$_{1'}$, J$_{1'2'}$=7.6 Hz, J$_{1',2'}$=6.4 Hz), 6.04 (dd, 1, T1 H$_{1'}$,J$_{1',2'}$=7.3 Hz, J$_{1',2'}$=3.4 Hz), 5.36 (d, 1, T2 OH), 5.16 (t, 1, T1 OH), 4.07–4.22 (m, 3, T2 H$_{3',5',5''}$), 3.91 (m, 2, T1 T2 H$_{4'}$), 3.50–3.73 (m, 2, T1 H$_{5',5''}$), 3.12 (m, 1, T1 H$_{3'}$), 2.05–2.44 (m, 4, T1 T2 H$_{2',2''}$), and 1.76 (s, 6, 2CH$_3$). MS FAB: M/z 494 (M+H)$^+$.

EXAMPLE 10

Synthesis of phosphoramidate containing (3'-CH=N—O—CH$_2$-5') linked oligonucleoside 3'-De(oxyphosphinico)-3'-(methylidynenitrilo)-5'-O-(dimethyoxytriphenylmethyl)-thymidylyl-(3'→5') -3'-O-(β-cyanoethyldiisopropylaminophospiryl)thymidine The isomeric dimer of Example 9 was further dimethyoxytrityled at the hydroxyl group of the 5' terminus nucleoside followed by conversion to its 3'-O-β-cyanoethyldiisopropylphosphoramidite derivative at the hydroxyl group at the 3' terminus nucleoside of the dimer following the procedure described in Oligonucleotide Synthesis: a practical approach, Ed. M. J. Gait, IRL Press, 1984, to yield the title compound. $^1$H NMR (CDCl$_3$) δ 8.77 (br s, 2, 2NH), 7.68 (s, 0.77, T1 C$_6$H E-isomer), 7.59 (s, 0.23, T1 C$_6$H E-isomer), 6.3 (ps t, 1, T2 CH$_{1'}$), 6.14 (m, 0.77, T1 CH$_1$, E-isomer), 6.08 (m, 0.23, T$_1$CH$_1$, Z-isomer), 1.80 and 1.50 (2S, 6, 2 CH$_3$) and other protons. $^{31}$P NMR (CDCl$_3$) 150.77 and 150.38 (Z-isomer); 150.57 and 150.38 (E-isomer).

The protected dimer can be conveniently stored and used for coupling utilizing an automated DNA synthesizer (ABI 380B) as and when required for specific incorporation into oligomers of therapeutic value. Further as per further examples of the specification, the oxime linked dimer is reduced to a dimer bearing a corresponding hydroxylamine linkage and this in turn can be alkylated to a hydroxylmethylamine or other hydroxyalkylamine linkage.

EXAMPLE 11

Synthesis of (3'-CH$_2$—NH—O—CH$_2$-5') linked oligonucleoside

3'-De(oxyphosphinico)-3'-(methyleneimino)thymidylyl-(3'→5')-thymidine

To a stirred solution of blocked dimer 3'-de(oxyphosphinico)-3'-(methylidynenitrilo)thymidylyl-(3'→5')-3'-O-(t-butyldiphenylsilyl)thymidine (0.49 g, 1 mmol) in glacial AcOH (5 ml) was added NaBH$_3$CN (0.19 g, 3 mmol) in 3-portions under argon at room temperature. The suspension was stirred for 1 h until bubbling of solution ceased. Additional NaBH$_3$CN (0.19 g, 3 mmol) was added in a similar manner and stirring continued for 1 h. The AcOH was removed under reduced pressure to furnish 3'-de(oxyphosphinico)-3'-(methyleneimino)-thymidylyl-(3'→5')-3'-O-(t-butyldiphenylsilyl)thymidine. Deblocking of this dimer as described before using nBu$_4$NF/THF and HCl/MeOH furnished the title compound, 3'-de(oxyphosphinico)-3'-(methyleneimino)thymidylyl-(3'→5')-thymidine, (0.44 g, 90%) as white powder. This dimer was further purified by HPLC (as described for the 3'-de(oxyphosphinico)-3'-(methylidynenitrilo)thymidylyl-(3'→5')-thymidine dimer of Example 9) to obtain an analytically pure sample. $^1$H NMR (DMSO-d$_6$) δ 11.23 (br s, 2, 2NH), 7.83 and 7.49 (2s, 2, 2C$_6$H), 6.82 (t, 1, NHO), 6.14 (pseudo t, 1, T2 H$_{1'}$, J$_{1'2'}$=7.6 Hz, J$_{1',2''}$=6.5 Hz), 5.96 (dd, 1, T1 H$_{1'}$, J$_{1',2'}$=6.9 Hz, J$_{1',2''}$=4.3 Hz), 5.28 (s, 1, T2 OH), 5.08 (s, 1, T1 OH), 4.18 (m, 1, T2 H$_{3'}$), 3.89 (m, 1, T1 H$_{4'}$), 3.54–3.78 (m, 5, T1 T2 H$_{5',5''}$, T2 H$_{4'}$), 2.76–2.94 (m, 2, T1 H$_{3'}$), 2.42 (m, 1, T1 H$_{3'}$), 2.0–2.17 (m, 4, T1, T2 H$_{2',2''}$), 1.77 and 1.74 (2s, 6, 2 CH$_3$). MS FAB: M/z 496 (M+H)$^+$. Anal. Calcd. for C$_{21}$H$_{29}$N$_5$O$_9$H$_2$O: C, 49.12; H, 6.09; N, 13.64. Found: C, 48.99; H, 5.96; N, 13.49.

EXAMPLE 12

Synthesis of methylated [3'-CH$_2$—N(CH$_3$)—O—CH$_2$-5'] linked oligonucleoside 3'-De(oxyphosphinico)-3'-[methylene(methylimino)] thymidylyl-(3'→5')thymidine To a stirred solution of 3'-de(oxyphosphinico)-3'-(methyleneimino)thymidylyl-(3'→5')-3'-O-(t-butyldiphenylsilyl)thymidine dimer (0.99 g, 1 mmol) in glacial AcOH (10 ml) was added aqueous HCHO (20%, 3 ml). The solution was stirred for 5 min. at room temperature and to this was added NaBH$_3$CN (0.19 g, 3 mmol) in 3-portions under argon at room temperature. The addition of NaBH$_3$CN (0.19 g) was repeated once more and solution was further stirred for 1 h. The reaction mixture was concentrated to furnish crude 3'-de(oxyphosphinico)-3'-[methylene(methylimino)]-thymidylyl-(3'→5')-3'-O-(t-butyldiphenylsilyl)thymidine dimer, which on deblocking (nBu$_4$NF/THF, HCl/MeOH) furnished the title compound, 3'-de(oxyphosphinico)-3'-[methylene(methylimino)] thymidylyl-(3'→5') thymidine, (0.44 g, 87%) as white solids. The 3'-de(oxyphosphinico)-3'-(methylene(methylimino) ]thymidylyl-(3'→5') thymidine dimer was further purified by preparative HPLC furnishing an analytically pure sample. $^1$H NMR (DMSO-d$_6$) δ 11.30 and 11.24 (2s, 2, 2NH), 7.82 and 7.50 (2s, 2, 2C$_6$H), 6.15 (pseudo t, 1, T2 H$_{1'}$, J$_{1',2'}$=6.3 Hz, J$_{1',2''}$=7.3 Hz), 6.00 (pseudo t, 1, T1 H$_{1'}$, J$_{1',2'}$=4.2 Hz, J$_{1',2''}$=6.1 Hz), 5.31 (m, 1, T2 OH), 5.08 (m, 1, T1, OH), 4.17 (m, 1, T2 H$_{3'}$), 3.88 (m, 1, T2 H$_{4'}$), 3.57–3.83 (m, 5, T1 T2 H$_{5',5''}$, T1 H$_{4'}$), 2.69 (m, 2, T1 H$_{3'}$), 2.57 (s, 3, N—CH$_3$), 2.50 (m, 1, T1 H$_{3'}$), 2.05–2.14 (m, 4, T1 T2 H$_{2',2''}$), 1.79 and 1.76 (2s, 6, 2 CH$_3$). MS FAB: M/z 510 (M+H)$^+$. Anal. Calcd. for C$_{23}$H$_{31}$N$_5$O$_9$.H$_2$O: C, 50.09; H, 6.31; N, 13.28. Found: C, 50.05; H, 6.21, N, 13.08.

EXAMPLE 13

Synthesis of phosphoramidate containing [3'-CH$_2$—N(CH$_3$)—O—CH$_2$-5'] linked oligonucleoside 3'-De(oxyphosphinico)-3'-[methylene(methylimino)]-5'-O-(dimethoxytriphenylmethyl)thymidylyl-(3'→5')-3'-O-(β-cyanoethyldiisopropylaminophosphiryl)thymidine The 3'-de(oxyphosphinico)-3'-[methylene(methylimino)] thymidylyl-(3'→5') thymidine dimer of Example 12 was tritylated and phosphitylated as described in Oligonucleotide Synthesis: a practical approach, Ed. M. J. Gait, IRL Press, 1984, in an overall yield of 82%. The protected dimer was purified by silica gel column chromatography (CH$_2$Cl$_2$:MeOH:Et$_3$N; 9:1:0.1, v/v) and homogenous fractions were pooled and evaporated to furnish pure 3'-de(oxyphosphinico)-3'-[methylene(methylimino)]-thymidylyl-5'-O-(dimethoxytriphenylmethyl)-(3'→5')-3'-O-(β-cyanoethyldiisopropylaminophosphiryl)thymidine as a white foam (used as such for DNA synthesis). The product was isolated as a mixture of diastereoisomer: $^{31}$P NMR (CDCl$_3$) δ 149.62 and 149.11 ppm; $^1$H NMR (CDCl$_3$) δ6.22 (pseudo t, 1, T2 H$_{1'}$, J$_{1',2'}$=J$_{1',2''}$=6.7 Hz), 6.16 (pseudo t, 1, T1 H$_{1',2'}$=J$_{1',2''}$=5.8 Hz), 2.58, 2.56 (2s, 3, N—CH$_3$), 1.82, 1.49 (2s, 6, 2 CH$_3$), and other protons.

The above protected phosphoramidate bearing dimer can be conveniently stored and used for coupling utilizing an automated DNA synthesizer (ABI 380B) as and when required for specific incorporation into oligomers of therapeutic value. Other dimers of the inventions, as for example but not limited the above noted methylidynenitrilo, i.e., oxime, and methyleneimino, i.e., aminohydroxy, dimers are converted to their corresponding phosphoramidate derivatives in the same manner as this example and incorporated into oligonucleotide in the standard manner as noted below. An oligomer bearing the oxime linked nucleoside dimer is reduced to an oligomer bearing a corresponding hydroxylamine linked nucleoside dimer. As noted in other examples, reduction can be effected as an CPG bound oligomer or after removal from the CPG.

EXAMPLE 14

Synthesis of intermittent (3'-CH=N—O—CH$_2$-5'), i.e., oxime; (3'-CH$_2$—NH—O—CH$_2$-5'), i.e., aminohydroxy; (3'-CH$_2$—N(CH$_3$)—O—CH$_2$-5'), i.e., N-methyl-aminohydroxy; (3'-CH$_2$—O—N(CH$_3$)—CH$_2$-5'), i.e., N-methyl-hydroxyamino; or (3'-CH$_2$—N(CH$_3$)—N(CH$_3$)—CH$_2$-5'), i.e., N,N'-dimethyl-hydrazino linked oligonucleosides An appropriate 2'-deoxynucleoside that will become the 3'-terminal nucleoside of an oligonucleoside is bound to a CPG column for use on an ABI 380B automated DNA synthesizer. Standard phosphoramidite chemistry program steps were employed to place the dimer bearing the (3'-CH=N—O—CH$_2$-5'), i.e., oxime; (3'-CH$_2$—NH—O—CH$_2$-5'), i.e., aminohydroxy; (3'-CH$_2$—N(CH$_3$)—O—CH$_2$-5'), i.e., N-methylaminohydroxy; (3'-CH$_2$—O—N(CH$_3$)—CH$_2$-5'), i.e., N-methylhydroxyamino; or (3'-CH$_2$—N(CH$_3$)—N(CH$_3$)—CH$_2$-5'), i.e., N,N'-dimethylhydrazino, linkages into the desired position or positions of choice within the sequence.

EXAMPLE 15

General and specific NaBH$_3$CN reduction for conversion of (3'-CH=N—O—CH$_2$-5') linkage to (3'-CH$_2$—NH—O—CH$_2$-5')

Reduction of a Dimer

To a solution of a dimer (0.49 g, 1 mmol) in glacial acetic acid (AcOH) (5 ml) was added sodium cyanoborohydride (0.19, 3 mmol) in AcOH (1 ml), under an argon atmosphere at room temperature. The suspension was stirred for 1 h, and an additional amount of NaBH$_3$CN in AcOH (1 ml) was added and stirring continued for 1 h. The excess of AcOH was removed under reduced pressure at room temperature. The residue was coevaporated with toluene (2×50 ml) and purified by silica gel (25 g) column chromatography. Elution with CH$_2$Cl$_2$:MeOH (9:1, v/v) and pooling of appropriate fractions, followed by evaporation furnished 0.36 g (75%) of solid dimer.

Reduction of an oligonucleoside

CPG-bound oligonucleoside (1 μM), that contains one (or more) backbone modified linkages is taken off the DNA synthesizer after completion of its synthesis cycles. A 1.0M NaBH$_3$CN solution in THF:AcOH (10 ml, 1:1 v/v) is pumped through the CPG-bound material in a standard way utilizing a syringe technique for 30 min. The column is washed with THF (50 ml), and the reduced oligonucleoside is released from the support column in a standard way.

Alternative Reduction of an oligonucleoside

As an alternative to the above reduction, reduction can also be accomplished after removal from the CPG support. At the completion of synthesis the oligonucleoside is removed from the CPG-support by standard 25 procedures. The 5'-O-trityl-on oligonucleoside is purified by HPLC and then reduced by the NaBH$_3$CN/AcOH/THF method as described above.

EXAMPLE 16

Synthesis of (3'-CH$_2$—N(CH$_3$)—O—CH$_2$-5') linked oligonucleoside having a 2',3'-didehydro nucleoside as its 5' terminal nucleoside 3'-De(oxyphosphinico)-2',3'-didehydro-3'-[methylene(methylimino)]thymidylyl-(3'→5')thymidine.

To a stirred solution of 1-(5'-O-(MMTr)-β-D-glyceropentofuran-3'-ulosyl]thymine (0.13 mmol; prepared according to the procedure of T.-C. Wu, et al., Tetrahedron, 1989, 45:855, 5'-O-(methyleneamino)-3'-O-(t-butyldiphenylsilyl) thymidine (0.13 mmol; prepared according to the procedure of Debart, et al., Tetrahedron Letters 1992, 33, 2645, ethylene glycol (0.5 mmol), and HMPA (0.5 ml) was added SmI$_2$ in THF (0.1 mol, 3 ml, 3 mmol) at room temperature. The color of SmI$_2$ fades out as the reaction proceeds to form the desired adduct. After complete disappearance of starting materials the reaction mixture is worked-up in the usual way. (The product could be purified by silica column chromatography for characterization). The crude mixture of 3'-epimeric adduct is then alkylated (HCHO/NaCNBH$_3$/AcOH) as described in other of these examples. The methylated product is then treated with methylsulfonylchloride in pyridine to obtain a 3'-epimeric mesylate, which on base treatment would furnish the title compound.

EXAMPLE 17

Synthesis of (3'-CH$_2$—CH$_2$—NH—CH$_2$-5') linked oligonucleoside

3'-De(oxyphosphinico)-3'-(1,2-ethanediylimino) thymidylyl-5'-O-(t-butyldimethylsilyl)-(3'→5')-3'-O-t-butyldiphenylsilyl)-5'-deoxythymidine To a stirred solution of aldehyde (2.5 g, 6.5 mmol, freshly prepared according to the procedure described by Fiandor, et al., Tetrahedron Letts. 1990, 33, 597], 5'-amino-3'-O-(t-butyldiphenylsilyl)-5'-deoxythymidine [3.13 g, 6.5 mmol, prepared in two steps via 3'-O-silylation of 5'-azido-5'-deoxythymidine in the manner of Hata, et al., J. Chem. Soc. Perkin I 1980, 306, and subsequently reduction of the product by the method of Poopeiko, et al., Syn. Lett. 1991, 342], AcOH (0.39, and 6.5 mmol) in dicholoroethane (65 ml) was added followed by NaBH(OAc)$_3$ (2.759, 13.08 mmol) under argon. The suspension was stirred for 3 hours at room temperature. The reaction mixture was diluted with $CH_2Cl_2$ (250 ml) and washed with water (2×100 ml). The organic layer was dried ($MgSO_4$) and concentrated to furnish the crude product as a syrup. The product was purified by silica gel column chromatography to furnish the title compound as white foam (3.5 g, 64%). $^1H$ NMR ($CDCl_3$) δ 0.1 [S, 6, $Si(C\underline{H}_3)_2$]; 0.9 and 1.1 (2s, 18, 2 $Si(C\underline{H}_3)_3$]; 1.85 and 1.95 (2s, 6, 2 $C\underline{H}_3$); 2.5 (m, 2, 3"$C\underline{H}_2$); 3.7 (m, 2, 5'$C\underline{H}_2$); 4.0 (m, 2, 3',4'$C\underline{H}$); 4.2 (m, 1, 3'$C\underline{H}$); 6.05 (m, 1, 1'$\underline{H}$); 6.28 (t, 1, 1'$\underline{H}$); 7.1 and 7.57 (2s, 2, C6$\underline{H}$); 7.35–7.7 [2m, 12, Si Ar$\underline{H})_2$], and other sugar protons.

3'-De(oxyphosphinico)-3'-(1,2-ethanediylimino)thymidylyl-(3'→5')-5'-deoxythymidine The protected dimer was deblocked in 81% yield following the standard procedure using $(Bu)_4NF$ in THF. The deblocked dimer was purified by HPLC for analysis. $^1H$ NMR (DMSO-$d_6$) δ 1.76 and 1.78 (2s, 6, $C\underline{H}_3$); 2.0–2.2 (3m, 4, 2'$C\underline{H}_2$); 3.15 (m, 2, $NC\underline{H}_2$); 3.56 (m, 2, 4'$\underline{H}$, 5'$C\underline{H}_2$); 4.18 (br s, 1, 3'$\underline{H}$); 5.17 and 5.22 (2 br s, 2, 2 O$\underline{H}$); 5.95 (t, 1, 1'$\underline{H}$); 6.1 (t, 1, 1'$\underline{H}$); 7.6 and 7.85 (2s, 2, 2($C_6\underline{H}$)); 11.25 (br s, 2 2N$\underline{H}$) and other protons.

EXAMPLE 18

Synthesis of Monomer Unit for (3'-$CH_2$—O—N=CH—5'), (3'-$CH_2$—O—NH—$CH_2$-5') and (3'-$CH_2$—O—N($CH_3$)—$CH_2$-5') Linkages 1-[3'-Deoxy-3'-C-(hydroxymethyl)-5'-O-(trityl)-β-D-erythro-pentofuranosyl]-thymine A suspension of $NaBH_4$ (1.36 g, 9.6 mmol) was added dropwise to a stirred solution of 3'-$\underline{C}$-formyl-5'-$\underline{O}$-tritylthymidine in EtOH:$H_2O$ (22 ml, 3:1, v/v) mixture at room temperature. After 3 h, EtOAc (300 ml) was added and the organic layer was washed with $H_2O$ (2×150 ml). The dried ($MgSO_4$) EtOAc extract was evaporated under reduced pressure and the residue was purified by silica gel column chromatography. Elution with $CH_2Cl_2$:MeOH (9:1, v/v), pooling and concentration of appropriate fractions gave the title compound (1.13 g, 83%). $^1H$-NMR ($CDCl_3$) δ 8.29 (br s, 1, N$\underline{H}$), 7.59 (s, 1, $C_6H$) 7.47–7.22 (m, 15, Tr$\underline{H}$) 6.13 (dd, 1, $\underline{H}_{1'}$, $J_{1',2'}$=6.5 Hz); 3.98 (m, 1, $\underline{H}_{4'}$); 3.62 (m, 2, $\underline{H}_{3'}$); 3.56–3.33 (m, 2, $\underline{H}_{5'},\underline{H}_{5''}$), 2.60 (m, 1, $\underline{H}_{3'}$); 2.33–2.20 (m, 2, $\underline{H}_{2'}, \underline{H}_{2'}$); 1.91 (br s, 1, OH); 1.53 (S, 3, $C\underline{H}_3$).

1-(3'-Deoxy-3'-C-[O-(phthalimidohydroxymethyl)]-5'-O-trityl-β-D-erythro-pentofuranosyl]-thymine Diisopropylazodicarboxylate (0.47 ml, 2.41 mmol) was added to a stirred solution of 3'-deoxy-3'-$\underline{C}$-(hydroxymethyl)-5'-$\underline{O}$-trityl-thymidine (0.8 g, 1.62 mmol), N-hydroxyphthalimide (0.35 g, 2.15 mmol), triphenylphosphine (0.56 g, 2.15 mmol) in dry THF (10 ml) at room temperature. After 48 h, the products were concentrated and the residue was extracted with $CH_2Cl_2$ (2×100 ml). The $CH_2Cl_2$ extracts were washed with $NaHCO_3$ (5%, 100 ml) and water (100 ml).

The dried ($MgSO_4$) extract was evaporated under reduced pressure and the residue was purified by short-silica gel chromatography. Elution with EtOAC:Hexanes (1:1, v/v), pooling and concentration of appropriate fractions gave the title compound as white foam (0.82 g, 79%). $^1H$-NMR ($CDCl_3$) δ8.24 (s, 1, N$\underline{H}$); 7.85–7.20 (m, 20, Tr$\underline{H}$, Ar$\underline{H}$, $C_6\underline{H}$), 6.20 (m, 1, $\underline{H}_{1'}$), 4.22–4.16 (m, 3, $\underline{H}_{4'}$, $\underline{H}_{3'}$), 3.63–3.40 (m, 2, $\underline{H}_{5'}$, $\underline{H}_{5''}$), 3.02 (m, 1, $\underline{H}_{3'}$), 2.50–2.43 (m, 2, $\underline{H}_{2'}$, $\underline{H}_{2''}$); 1.51 (s, 3, $C\underline{H}_3$). Anal. Calcd. for $C_{38}H_{33}N_3O_7$. 0.5 EtOAc:C, 69.86; H, 5.42, N, 6.11. Found: C, 70.19; H, 5.27; N, 5.75

1-{3'-Deoxy-3'-C-[O-(aminohydroxymethyl)]-5'-O-trityl-β-D-erythro-pentofuranosyl}-thymine Methylhydrazine (0.12 ml, 2.25 mmol) was added to a stirred solution of 3'-deoxy-3'-C-[O-(phthalimidohydroxymethyl)]-5'-O-tritylthymidine (0.77 g, 1.2 mmol) in dry $CH_2Cl_2$ (9 ml) at room temperature. After 1 h, the precipitate was filtered and the residue washed with $CH_2Cl_2$ (2×10 ml). The combined filtrates were concentrated and the residue was purified by silica gel column chromatography. Elution with $CH_2Cl_2$:MeOH (97:3, v/v), pooling and evaporation of appropriate fractions gave the title compound as white powder (0.43 g, 70%). $^1H$-NMR ($CDCl_3$) δ 8.59 (br s, 1, N$\underline{H}$), 7.66 (m, 1, $C_6\underline{H}$), 7.40–7.15 (m, 15, Tr$\underline{H}$), 6.06 (pseudo t, 1, $\underline{H}_{1'}$), 5.22 (br s, 2, N$\underline{H}_2$), 3.89 (m, 1, $\underline{H}_{4'}$), 3.65–3.20 (m, 4, $\underline{H}_{5'}$, $\underline{H}_{5''}$, $\underline{H}_{3''}$), 2.81 (m, 1, $\underline{H}_{3'}$), 2.21–2.13 (m, 2, $\underline{H}_{2'}$, $\underline{H}_{2''}$), 1.37 (s, 3, $C\underline{H}_3$).

EXAMPLE 19

Synthesis of (3'-$CH_2$—O—N=CH-5'), (3'-$CH_2$—O—NH—$CH_2$-5') and (3'-$CH_2$—O—N($CH_3$)—$CH_2$-5') linked oligonucleosides 3'-De(oxyphosphinico)-3'-[methyleneoxy(methylimino)] thymidylyl-(3'→5')-5'-deoxythymidine A mixture of 1-[4-$\underline{C}$-formyl-3-$\underline{O}$-(t-butyldiphenylsilyl)-β-D-erythro-pentofuranosyl)thymine [1 mmol, prepared according to the procedure of *Nucleosides and Nucleotides* 1990, 9, 533], 3'-deoxy-3'-$\underline{C}$-[(O-(aminohydroxymethyl)]-5'-O-tritylthymidine (1 mmol), AcOH (0.1 ml), and dry $CH_2Cl_2$ (25 ml) was stirred at room temperature for 1 h. The solvent was evaporated and the residue was dissolved in glacial AcOH (5 ml). $NaBH_3CN$ (3 mmol) was added to the stirred AcOH reaction mixture. After 1 h, an additional amount of $NaBH_3CN$ (3 mmol) was added and the mixture stirred for 1 h. The reaction was concentrated under vacuum and the residue was purified by silica gel column chromatography to furnish 5'-O-Tr-T-3'-$CH_2$—O—NH—$CH_2$-5'-T-3'-O-TBDPSi dimer. $^1H$-NMR ($CDCl_3$) δ 8.73 (br s, 2, 2N$\underline{H}$), 7.67 (s, 1 $C_6\underline{H}$), 7.674–7.23 (m, 20, Tr$\underline{H}$, TBDPh$\underline{H}$), 6.96 (s, 1, $C_6\underline{H}$), 6.23 (pseudo t, 1, T2 $\underline{H}_{1'}$), 6.11 (pseudo t, 1, $T_1$, $\underline{H}_{1'}$) 5.51 (br s, 1, N$\underline{H}$), 4.16 (m, 1, $T_2\underline{H}_{3'}$) 4.02 (m, 1, $T_2\underline{H}_{4'}$), 3.87 (m, 1, $T_1\underline{H}_{4'}$), 3.52 (m, 3, T1 $CH_{23''}$, $T_1\underline{H}_{5''}$), 3.23 (m, 1, $T_1\underline{H}5'$), 2.55–2.76 (m, 3, T1 $\underline{H}_{3'}$, T2 $\underline{H}_{5'}\underline{H}_{5''}$), 2.33–2.27 (m, 1, T2 $\underline{H}_{2'}$), 2.23–2.12 (m, 2, T1 $\underline{H}_{2'}$ $\underline{H}_{2''}$), 1.95–1.85 (m, 1, $T_2\underline{H}_{2''}$), 1.83 (s, 3, $C\underline{H}_3$) 1.45 (s, 3, $C\underline{H}_3$), 1.06 (s, 9, $(C\underline{H}_3)_3CSi$).

The latter dimer was methylated using HCHO/$NaBH_3CN$/AcOH and finally deblocked with $nBu_4NF$/THF and HF/$CH_3CN$ in two-steps to furnish the title compound (65% yield). $^1H$-NMR (DMSO-$d_6$) δ 11.27 (br s, 2, N$\underline{H}$); 7.85 (s, 1, T1 $C_6\underline{H}$); 7.51 (s, 1, $T_2$ $C_6\underline{H}$); 6.15 (pseudo t, 1, T2 $\underline{H}_1$, $J_{1',2'}$=7.8 Hz, $J_{1',2''}$=6.3 Hz); 6.00 (pseudo t, 1, $T_1$ $\underline{H}_{1'}$, $J_{1',2'}$=6.9 Hz, $J_{1',2''}$=4.5 Hz), 5.32 (br s, 1, O$\underline{H}_{3'}$), 5.09 (br s, 1, O$\underline{H}_{5'}$); 4.17 (m, 1, $T_2$ $\underline{H}_{3'}$); 3.90 (m, 1, $T_2$ $\underline{H}_4$); 3.76–3.66 (m, 4, $T_1$ $\underline{H}_{4'}$, $T_1$ $\underline{H}_{5'}$, $CH_{2\ 3''}$); 3.60–3.52 (m, 1, $T_1$ $\underline{H}_{5''}$); 2.82 (m, 2, $T_2$ $\underline{H}_{5'}$, $\underline{H}_{5''}$); 2.57 (s, 3, N—$C\underline{H}_3$); 2.47 (m, 1, $T_1$ $\underline{H}_{3'}$); 2.23–2.02 (m, 4, $\underline{H}_{2'}\underline{H}_{2''}$) 1.81 (s, 3, $C_5C\underline{H}_3$); 1.78 (s, 3, $C_5$ $C\underline{H}_3$). Anal. Calcd. for $C_{22}H_{31}N_5O_9$.0.5 $H_2O$: C, 50.96; H, 6.22; N, 13.50. Found: C, 51.01; H, 6.22; N, 13.19. MS (FAB+, glycerol) M+$H^+$ m/z=510.

EXAMPLE 20

Synthesis of phosphoramidate containing (3'-$CH_2$—O—N($CH_3$)—$CH_3$-5') linked oligonucleoside 3'-De(oxyphosphinico)-3'-[methyleneoxy(methylimino)]-thymidylyl-5'-O-(dimethyoxytriphenylmethyl)-(3'→5')-3-(O-β-cyanoethyldiisopropylaminophosphiryl)thymidine Dimethyoxytritylation of the dimer 5'-OH-T-3'-$CH_2$—O—$NCH_3$—$CH_2$-5'-T-3'-OH following the procedure described in Oligonucleotide Synthesis: a practical approach, Ed. M. J. Gait, IRL Press, 1984, furnished the 5'-O-DMTr protected dimer as white foam. $^1H$-NMR ($CDCl_3$) δ 7.67 (s, 1, $\underline{H}_6$); 7.44–6.82 (m, 14, $\underline{H}_6$, DMTr$\underline{H}$);

6.20 (pseudo t, 2, $H_1$); 4.3 (m, 1, $T_2H_3$·); 4.15 (m, 1, $T_2 H_{4'}$) 4.00 (m, 1, $T_1 H_{4'}$) 3.80 (s, 6, OC$H_3$); 3.77–3.23 (m, 4, $T_1 H_{5'}$, $H_{5''}$, $CH_{2\ 3''}$); 2.89–2.50 (m, 3, $T_2 H_5, H_{5''}$, T1 $H_3'$); 2.62 (s, 3, N—C$H_3$); 2.48–2.08 (m, 4, $H_2, H_{2''}$); 1.9 (s, 3, $C_5CH_3$) 1.48 (s, 3 $C_5CH_3$).

Above compound was phosphitylated following the procedure described in Oligonucleotide Synthesis: a practical approach, Ed. M. J. Gait, IRL Press, 1984, to furnish the title compound in 70% yield over two steps as white powder. $^1$H NMR (CDCl$_3$) δ 8.25 (br s, 2, NH), 7.66 (s, 1, $C_6H$), 7.15–7.45 (m, 10, Ar$H$, $C_6H$), 6.8–6.9 (m, 4, Ar$H$), 6.12 (m, 2, $2C_1H$), 3.79 (s, 6, ArOC$H_3$), 2.56 (s, 3, N—C$H_3$), 1.88, 1.44 (2s, 6, 2 $C_5 CH_3$) and other protons. $^{31}$P NMR (CDCl$_3$) 149.42 and 148.75 ppm.

EXAMPLE 21

Synthesis of oligonucleosides having linkages that include pharmacokinetic and pharmacodynamic property modifying groups located therein on 3'-De(oxyphosphinico)-3'-[methylene(benzylimino)]-thymidylyl-5'-O-(dimethyoxytriphenylmethyl)-(3'→5')-3'-O-β-(cyanoethyldiisopropylaminophosphiryl)thymidine A reductive coupling of 3'-deoxy-3'-C-formyl-5'-O-tritylthymidine (1.5 mmol) with 5'-O-amino-3'-O-(t-butyldiphenylsilyl)thymidine (1.5 mmol) as described in Example 9 furnished 5'-O-Tr-T-3'-CH$_2$—NH—O—CH$_2$-5'-T-3'-O-TBDPSi dimer. This dimer was benzylated with C$_6$H$_5$CHO/NaBH$_3$CN/AcOH in the same manner as the above described methylation to yield N-benzylated dimer 5'-O-Tr-T-3'-CH$_2$—NBz-O—CH$_2$-5'-T-3'-O-TBDPSi. The latter dimer was deblocked using nBu$_4$NF/THF and HCl/MeOH methodology as described in above examples to furnish deblocked dimer 5'-OH-T-3'-CH$_2$—NBn-O—CH$_2$-5'-T-3'-OH, which on dimethoxytritylation and subsequent phosphitylation following the procedure described in Oligonucleotide Synthesis: a practical approach, Ed. M. J. Gait, IRL Press, 1984, gave the title compound (45% overall yield). $^1$H NMR (CDCl$_3$) δ 6.15 (pseudo t, 1, T2 $C_1, H$); 6.09 (m, 1, T1 $C_1, H$); 3.76 (s, 6, 20C$H_3$); 1.7 and 1.48 (2S, 6, 2-C$H_3$) and other protons. $^{31}$p NMR (CDCl$_3$) 149.59 and 149.23 ppm.

The phosphiltylated dimer was successfully incorporated into an oligomer using an automated DNA synthesizer in the manner of Example 8 illustrating the ability to attach of various pharmacokinetic and pharmacodynamic property modifying groups into the backbone linkage prior to the DNA synthesis of an oligonucleotide.

EXAMPLE 22

Synthesis of (3'-CH$_2$—NH—CH$_2$—CH$_2$-5'), (3'-CH$_2$—N(CH$_3$)—CH$_2$—CH$_2$-5'), and Phosphoramidate Derivative 3'-De(oxyphosphinico-3'-[(methyleneimino)-methylene]-5'-O-(dimethyoxytrityl)thymidylyl-(3'-5')thymidine A reductive amination [according to the procedure of Abdel-Magid, et al., Tetrahedron Letts. 1990, 31, 5595] of 3'-deoxy-3'-C-formyl-5'-O-tritylthymidine (1 mmol) with 1-[6'-amino-2',5',6'-trideoxy-3'-O-(t-butyldiphenylsilyl)-βD-erythro-hexofuranosyl]thymine [1.2 mmol, prepared according to the procedure of Etzold. et al., J.C.S. Chem. Comm. 1968, 422] in presence of AcOH gave a blocked dimer 5'-O-Tr-T-3'-CH$_2$NH—CH$_2$—CH$_2$-5'-T-3'-O-TBDPSi, which on deprotection as described in above examples gave 5'-OH-T-3'-CH$_2$—NH—CH$_2$—CH$_2$-5'-T-3'-OH dimer as white powder (70% yield). $^1$H NMR (D$_2$O, pH 5.6, 20° C.) δ T1 thymidine unit: 7.78 (s, 1, $C_6H$); 6.17 (t, 1, $C_1 H$); 4.45 (m, 1, $C_3H$); 4.08 (m, 1, $C_4H$); 4.00, 3.72 (m, 2, $C_{5'5''}H$); 2.9 (m, 2 $C_{6',6''}H$); 2.34 (m, 2, $C_{2',2}H$); 1.77 (s, 3, C$H_3$); T2 thymidine unit: 7.47 (s, 1 $C_6H$); 6.07 (t, 1, $C_1H$); 3.89 (m, 2, $C_{5'5''}H$); 3.79 (m, 1, $C_4H$); 2.89 (m, 1, $C_{3''H}$); 2.38 (m, 1, $C_2H$); 2.32 (m, 1, $C_3H$); 1.72 (s, 3, C$H_3$); and 2.68 (s, N—C$H_3$).

Pka determination:

The sensitivity of the proton chemical shift of the N-Me group of the foregoing dimer to change in response to change in pH was measured by NMR as an indicator of the pka of the backbone amine. The chemical shift moved downfield as the amino group was protonated. A 4 mg sample of 5'-OH-T-3'-CH$_2$—NCH$_3$—CH$_2$—CH$_2$-5'-T-3'-OH dimer was dissolved in 0.6 ml of 30 mM bicarbonate buffer. The pH was varied between 5.1 and 10.0 using 0.1N NaOH in 6-steps. The chemical shift of the N-methyl proton varied between 2.26 and 2.93 ppm, giving rise to a pka of 7.8±0.1. While we do not wish to be bound by theory, it is thus believed that at physiological pH this backbone will be protonated.

3'-De(oxyphosphinico-3'-[methylene(methylimino) methylene]-5'-O-(dimethyoxytrityl)-thymidylyl-(3'→5')-3'O-(β-cyanoethyldiisopropylaminophosphiryl)thymidine The proceeding dimer was methylated using HCHO/NaBH$_3$CN in AcOH to furnish 5'-OH-T-3'-CH$_2$—N(CH$_3$) —CH$_2$—CH$_2$-5'-T-3'-OH dimer, which on dimethoxytritylation and phosphitylation following the procedure described in oligonucleotide Synthesis: a practical approach, Ed. M. J. Gait, IRL Press, 1984, gave the title compound as foam (68% yield). $^1$H NMR (CDCl$_3$) δ 6.12 (m, 2, $2C_1H$); 2.15, 2.14 (2s, 3, N—C$H_3$); 1.88, 1.45 (2s, 6, 2 $C_5CH_3$) and other protons. $^{31}$P NMR (CDCl$_3$) 149.49 and 148.96 ppm.

EXAMPLE 23

A (3'-CH$_2$—N(labile blocking group)—O—CH$_2$-5') diner and phosphoramidate derivative—a diner Incorporating a 3'-de(oxyphosphinico)-3'-(methyleneimino) (3'→5') linkage having a labile N-protecting group for regeneration of a (3'-CH$_2$—NH—O—CH$_2$-5) linkage 3'-De(oxyphosphinico)-3'-[methylene (phenoxyacetylimino)]-thymidylyl-(3'→5')-thymidine To a stirred solution of 5'-O-Tr-T-3'-CH$_2$—NH—O—CH$_2$-5'-T-3'-O-TBDPSi (1 mmol, prepared according to the procedure of Debart, et al., Tetrahedron Letts. 1992, 33, 2645) in dry pyridine (10 ml) was added phenoxyacetylchloride (1.2 mmol). After 12 h, the products were diluted with CH$_2$Cl$_2$ (200 ml) and washed with sat. NaHCO$_3$ (2×50 ml), water (2×50 ml) and dried (MgSO$_4$). The CH$_2$Cl$_2$ extract was concentrated and residue purified by silica gel column chromatography. Elution with CH$_2$Cl$_2$:MeOH (9:1, v/v), pooling of appropriate fractions and evaporation furnished 5'-O-Tr-T-3'-CH$_2$—N(COCH$_2$OPh)—O—CH$_2$-5'-T-3'-O-TBDPSi dimer as white foam. $^1$H NMR (DMSO-d$_6$) δ 11.35 (br s, 2, NH); 7.6–6.65 (m, 32, Tr, TBDPS, phenoxyacetyl, $C_6H$); 6.3 (pseudo t, 1, $H_1$·); 6.03 (pseudo t, 1, $H_1$·); 4.5 (m, 2, C$H_2$); 4.3 (m, 1, $T_2 H_3$); 3.9–3.3 (m, 6, $T_1 H_{4'}$, $T_2H_{4'}$, $T_2H_{5'}$, $H_{5''}$, CH$_{2\ 3''}$); 3.10 (m, 2, T, $H_{5'}$, $H_{5''}$); 2.65 (m, 1, $T_1 H_3$); 2.2–2.05 (m 4, $H_2$, $H_{2''}$); 1.58 (s, 3, C$H_3$); 1.4 (s, 3, C$H_3$); 1.02 (s, 9, (C$H_3$)$_3$CSi).

The foregoing dimer was sequentially deblocked with HF (48%)/CH$_3$CN (5:95, v/v) treatment to remove the trityl group, and the product on treatment with nBu$_4$NF/THF removed the silyl group to furnish title compound as white powder (70% yield for 3-steps). $^1$H NMR (DMSO-d$_6$) δ 11.35 (br s, 1, NH); 11.25 (br s, 1, NH) 7.92 (s, 1, $C_6H$); 7.5 (s, 1, $C_6H$); 7.2–6.8 (m, 5, ArH); 6.23 (pseudo t, 1, $H_1$·); 5.98 (dd, 1, $H_{1'}$); 5.45 (d, 1, OH$_3$·), 5.15 (t, 1, OH$_{5'}$); 4.9 (m, 2, C$H_2$); 4.3–3.5 (m, 9, $T_2 H_{3'}$, $H_{4'}H_{5'}H_{5''}$, C$H_{23''}$); 2.6 (m, 1, $T_1 H_3$); 2.25–2.00 (m, 4, $H_2, H_{2''}$); 1.75 (s, 3, C$H_3$); 1.65 (s, 3, C$H_2$).

The latter dimer was dimethoxytritylated as per the procedure of described in Oligonucleotide Synthesis: a practical approach, Ed. M. J. Gait, 1984, IRL Press, to furnish 5'-O-DMT-T-3'-CH$_2$—N—(COCH$_2$OPh)—O—CH$_2$-5'-T-3'-OH as pale yellow colored foam. $^1$H NMR (DMSO d$_6$) δ 11.3 (br s, 2, NH); 7.55 (s, 1, C$_6$H). 7.45 (s, 1, C$_6$H); 7.38–6.75 (m, 18, DMTrH, phenoxyacetyl-H); 6.22 (pseudo t, 1, T$_2$ H$_1$·); 6.05 (pseudo t, 1, T$_1$ H$_1$·); 4.75–4.60 (m, 2, CH$_2$); 4.25 (m, 1, T$_2$ H$_5$·); 4.18 (m, 1, T$_2$ H$_3$·); 4.05 (m, 1, T$_2$ H$_5$·); 3.9 (m, 2, H$_4$·); 3.8–3.6 (m, 2, CH$_2$ $_3$·); 3.65 (s, 6, 2OCH$_3$) 3.2 (m, 2, T$_1$, H$_5$H$_5$·) 2.82 (m, 1, T$_1$ H$_3$·); 2.3–2.05 (m, 4, H$_2$H$_2$·); 1.6 (s, 3, T$_2$ CHCH$_3$); 1.38 (s, 3, T1 CH$_3$).

The above dimer on phosphitylation following the procedure described in Oligonucleotide Synthesis: a practical approach, Ed. M. J. Gait, 1984, IRL Press, furnished the phosphoramidate derivatized dimer (appropriate for use on DNA synthesizer) as a foam (75% in 2 steps). $^1$H NMR (CDCl$_3$) δ 7.62 (s, 1, C$_6$H); 7.2–7.45 (2m, 12, ArH); 6.77–7.05 (3m, 7, ArH, C$_6$H); 6.15 (pseudo t, 1, C$_1$H); 6.05 (t, 1, C$_1$H); 4.7 (m, 2, 2C$_4$H); 3.74 (2s, 6, 2ArOCH$_3$); 2.95 (m, 1, C$_3$·H); 1.78, 1.77 (2s, 3, C$_5$CH$_3$); 1.41 (s, 3, C$_5$CH$_3$), and other protons. $^{31}$P NMR (CDCl$_3$) 1.49.76 and 149.56 ppm.

EXAMPLE 24

Regeneration of (3'-CH$_2$—NH—O—CH$_2$-5') linkage from (3'-CH$_2$—N(labile blocking group)—CH$_2$—CH$_2$-5') linkage In an oligonucleotide The phosphitylated dimer of Example 23 will be incorporated within an oligonucleotide as per the procedure of Example 8. After completion of the oligonucleotide on the support, the oligonucleotide is cleaved from the support utilizing standard ammonium hydroxide conditions. Concurrent with the cleavage from the support the ammonium hydroxide treatment will further cleave the phenoxyacetyl blocking group from the imino nitrogen of the incorporated (3'-CH$_2$—N(COCH$_2$OPh)—O—CH$_2$-5') oligonucleoside dimer to yield the (3'-CH$_2$—NH—O—CH$_2$-5') linked oligonucleoside dimer within the oligonucleotide structure.

EXAMPLE 25

5'-O-(t-Butyldimethylsilyl)-3'-O-Phthalimidothymidine, 2

To a solution of 5'-O-t-butyldimethylsilylthymidine [1, 21.36 g, 60 mmol, prepared according to the procedure of Nair, et al., *Org. Prep. Procedures Int.* 1990, 22, 57 in dry THF (750 ml)], triphenylphosphine (17.28 g, 66 mmol) and N-hydroxyphthalimide (10.74 g, 66 mmol) were added. The solution was cooled to 0° C. and diisopropylazodicarboxylate (15.15 g, 75 mmol) was added dropwise over a period of 3 hr while stirring under nitrogen. The reaction mixture was then stirred at room temperature for 12 hr. The solution was evaporated and the residue was dissolved in CH$_2$Cl$_2$ (750 ml), extracted with sat. NaHCO$_3$ (200 ml), and water (200 ml), dried (MgSO$_4$), filtered and concentrated to furnish yellow oily residue. Silica gel column chromatography (100% hexanes, and then hexanes:Et$_2$O gradient to 90% Et$_2$O) of the residue gave compound 2 as a colorless glass (18.68 g, 62%); $^1$H NMR (CDCl$_3$) δ 0.05 [2s, 6, (CH$_3$)$_2$], 0.91 [s, 9, (CH$_3$)$_3$], 2.0 (s, 3, CH$_3$), 2.5–2.65 (m, 2, 2'CH$_2$), 4.05–4.2 (m, 2, 5'CH$_2$), 4.25–4.35 (m, 1, 4'H), 5.0 (m, 1, 3'H) 6.15 (m, 1, 1'H), 8.6 (br s , 1, NH), and aromatic protons. Anal. Calcd. for C$_{24}$H$_{31}$N$_3$O$_7$Si: C, 57.46;H, 6.23; N, 8.37. found: C, 57.20; H, 6.26; N, 8.27.

EXAMPLE 26

3'-O-Amino-5'-O-(t-Butyldimethylsilyl)thymidine, 3

Cold methylhydrazine (1.6 ml, 30 mmol) was added to a stirred solution of 5'-O(t-butyldimethylsilyl)-3'-O-phthalimidothymidine (2, 4.6 g, 9.18 mmol) in dry CH$_2$Cl$_2$ (60 ml) at 5°–10° C. After 10 minutes white precipitation of 1,2-dihydro-4-hydroxy-2-methyl-1-oxophthalizine occurred.

The suspension was stirred at room temperature for 1 h. The suspension was filtered and precipitate washed with CH$_2$Cl$_2$ (2×20 ml). The combined filtrates were concentrated and the residue purified by silica gel column chromatography. Elution with CH$_2$Cl$_2$:MeOH (100:0→97:3, v/v) furnished the title compound (3.40 g, 100%) as white solid. Crystallization from CH$_2$Cl$_2$ gave white needles, m.p. 171° C.; $^1$H NMR (CDCl$_3$) δ 0.05 [s, 6, (CH$_3$)$_2$], 0.90 [s, 9, (CH$_3$)$_3$], 2.22–2.58 (2m, 2, 2'CH$_2$), 3.9–4.08 (m, 3, 5'CH$_2$, and 3'H) 4.30 (m, 1, 4'H) 5.5 (br s, 2, NH$_2$) 6.2 (m, 1, 1'H), 7.45 (s, 1, C$_6$H) 8.9 (br s, 1, NH). Anal. Calcd. for C$_{16}$H$_{29}$N$_3$O$_5$Si: C, 51.72; H, 7.87; N, 11.32. found: C, 51.87, H, 7.81; N, 11.32.

EXAMPLE 27

3'-O-Aminothymidine, 4

3'-O-Amino-(t-butyldimethylsilyl)thymidine was deblocked with (Bu)$_4$NF/THF in standard way to furnish compound 4 (72%). Crystallized from ether/hexanes/ethanol as fine needles, mp 81° C. $^1$H NMR (Me$_2$SO-d$_6$) δ 1.78 (h, 3, CH$_3$), 2.17 and 2.45 (2 m, 2, 2'CH$_2$), 3.70 (m, 2, 5'H$_2$), 3.88 (m, 1, 4'H), 4.16 (m, 1, 3'H), 4.8 (br s, 1, 5'OH), 6.05 (dd, 1, 1'H), 6.2 (br s, 2 NH$_2$), 7.48 (s, 1, C$_6$H), and 11.24 (br s, 1, NH). Anal. Calcd. for C$_{10}$H$_{15}$N$_3$O$_5$: C, 46.69; H, 5.87; N, 16.33; found: C, 46.55; H, 5.91; N, 16.21.

EXAMPLE 28

3'-O-Dephosphinico-3'-O-(Methylimino)thymidylyl-(3→5')-5'-Deoxythymidine, 9

Step 1.

3'-O-Amino-5'-O-(t-butyldimethylsilyl)thymidine (3, 1.85 g, 5 mmol), 3'-O-(t-butyldimethylsilyl)thymidine-5'-aldehyde [5, 2.39 g, 5 mmol; freshly prepared by following the method of Camarasa, et al., *Nucleosides and Nucleotides* 1990, 9, 533] and AcOH (0.25 ml) were stirred together in CH$_2$Cl$_2$ (50 ml) solution at room temperature for 2 h. The products were then concentrated under reduced pressure to give the intermediate oxime linked dimer, compound 6.

Step 2.

The residue obtained from Step 1 was dissolved in AcOH (25 ml). NaCNBH$_3$ (1.55 g, 25 mmol, in 3-portions) was added to the stirred AcOH solution at room temperature. The solution was stirred for 30 min to give the intermediate imine linked dimer, compound 7.

Step 3.

Aqueous HCHO (20%, 2 ml, 66 mmol) and additional NaCNBH$_3$ (1.55 g, 25 mmol, in 3-portions) was added to the stirred reaction mixture of Step 2 at room temperature. After 2 h, the solution was diluted with EtOH (100 ml), and resulting suspension was evaporated under reduced pressure. The residue was dissolved in CH$_2$Cl$_2$ (150 ml) and then washed successively with 0.1M HCl (100 ml), saturated aqueous NaHCO$_3$ (100 ml), and water (2×50 ml). The dried (MgSO$_4$) CH$_2$Cl$_2$ solution was evaporated to give crude methylated imine linked dimer 8.

Step 4.

The residue from Step 3 was dissolved in the THF (30 ml) and a solution of (Bu)$_4$NF (1M in THF, 10 ml) was added while stirring at room temperature. After 1 h, the reaction mixture was evaporated under reduced pressure and the residue was purified by short column chromatography. The appropriate fractions, which eluted with CH$_2$Cl$_2$:MeOH (8:2, v/v) were pooled and evaporated to give compound 9 as a foam (0.74 g, 30%). $^1$H NMR (Me$_2$SO-d$_6$) δ 1.78 (s, 6, 2C H$_3$), 2.10 (m, 4, 2'CH$_2$), 2.5 (s, 3, N—CH$_3$), 2.8 (m, 2, 5'-N-CH$_2$), 3.6–4.08 (5m, 6, 5' CH$_2$, 4' CH, 3' CH), 4.75 and 5.3 (2 br s, 2, 3' and 5' OH), 6.02 (d, 1, 1'H), 6.1 (t, 1, 1'H), 7.4 and 7.45 (2s, 2, 2C$_6$H), 11.3 (br s, 2, NH).

EXAMPLE 29
Methyl 3-O-(t-Butyldiphenylsilyl)-2,5-Dideoxy-5-O-Formylα/β-D-erythro-Pentofuranoside, 23

2-Deoxy-D-ribose, 21, was modified to methyl 2-deoxy-α/β-D-erythro-pentofuranoside (prepared according to the method of Motawai, et al., *Liebigs Ann. Chem.* 1990, 599–602), which on selective tosylation followed by 3-O-silylation gave methyl 3-O-(t-butyldimethylsilyl)-2-deoxy-5-O-tosyl-α/β-D-erythro-pentofuranoside in overall 70% yield. The latter compound on iodination followed by cyanation gave the corresponding 5-C-cyano intermediate compound 22, as a syrup. $^1$H NMR (CDCl$_3$) δ 1.05 (s, 9, (CH$_3$)$_3$), 1.9–2.38 (m, 4, 2 CH$_2$), 3.3 and 3.4 (2s, 3, OCH$_3$), 3.98–4.30 (3m, 2, 3, 4-CH), 4.95 and 5.05 (2m, 1, 1H), 7.4 and 7.7 (2m, 10, Ph H). IR (neat) 2253 cm$^{-1}$ (CH$_2$ CN)]. Compound 22 (stored at 0° C. without any degradation) was reduced(DIBAL-H) freshly every time as and when the title compound 23 was required.

EXAMPLE 30
5'-O-(t-Butyldimethylsilyl)-2',3'-Dideoxy-3'[(Methyleneamino)oxy]adenosine, 27; 5'-O-(t-Butyldimethylsilyl)-2',3'-Dideoxy-3'-[(Methyleneamino)oxy]cytidine, 28; and 5'-O-(t-Butyldimethylsilyl)-2',3'-Dideoxy-3'-[(Methyleneamino)oxy]guanosine, 29

3'-O-Amino-2'-deoxyadenosine, compound 24, 3'-O-amino-2'-deoxycytidine, compound 25, and 3'-O-amino-2'-deoxyguanosine, compound 26, prepared as per the procedures of European Patent Application 0 381 335 or in a manner analogous to the preparation of compound 4 by the procedure of Example 27 above, are blocked at their 5' position with a t-butyldimethylsilyl group according to the procedure of Nair, et al., *Org. Prep. Procedures Int.* 1990, 22, 57, to give the corresponding 3'-O-amino-5'-(t-butyldimethylsilyl)-2'-deoxyadenosine, 3'-O-amino-5'-(t-butyldimethylsilyl)-2'-deoxycytidine and 3'-O-amino-5'-(t-butyldimethylsilyl)-2'-deoxyguanosine nucleoside intermediates. Treatment of the blocked intermediate as per the procedure of Example 5 or as per the procedure of Preparation example 28 of European Patent Application 0 381 335 gives the corresponding 5'-O-(t-butyldimethylsilyl)-2',3'-dideoxy-3'-[(methyleneamino)oxy]adenosine, compound 27; 5'-O-(t-butyldimethylsilyl)-2',3'-dideoxy-3'-[(methyleneamino)oxy]cytidine, compound 28; and 5'-O-(t-butyldimethylsilyl)-2',3'-dideoxy-3'-[(methyleneamino)oxy]guanosine, compound 29.

EXAMPLE 31
3'-O-(t-Butyldiphenylsilyl)thymidine-6'-Aldehyde, 31

The title compound is prepared by homologation of the above described 3'-O-(t-butyldimethylsilyl)thymidine-5'-aldehyde (compound 5) utilizing the procedure of Barton, et al., *Tetrahedron Letters* 1989, 30, 4969. The 5'-aldehyde, compound 5, is treated via a witig reaction with (methoxymethylidene)triphenylphosphate. The resulting enol ether, compound 30, is hydrolyzed with Hg(OAc)$_2$, KI, H$_2$O and THF according to the procedure of Nicolaou, et al., *J. Am. Chem. Soc.* 1980, 102, 1404 to furnish the compound 31.

EXAMPLE 32
5'-O-(t-Butyldimethylsilyl)-3'-O-Dephosphinico-3'-O-(Nitrilomethylidyne)thymidylyl-(3'→5')-3'-O-(t-Butyldiphenylsilyl)-5'-Deoxythymidine, 32

The title compound is prepared by reaction of compound 31 and compound 3 in the manner of Example 28, Step 1 to furnish the dimeric oligonucleoside having an oxime backbone.

EXAMPLE 33
3'-O-Depho3'-O-Dephosphinico-3'-O-[(Methylimino)methylene]thymidyly-(3'→5')-3'-O-(t-Butyldiphenylsilyl)-5'-Deoxythymidine, 14

Method B

Compound 32 when treated as per the procedure of Steps 2 and 3 of Example 28 will also yield compound 14.

EXAMPLE 34
Methyl 3'-O-Dephosphinico-3'-O-[(Methyimino)methylene]thymidylyl-(3'→5')-3-O-(t-Butyldiphenylsilyl)-2,5-Dideoxy-α/β-D-erythro-Pentofuranoside, 33

Compound 23 and compound 3 are linked utilizing the procedure of Example 28, Steps 1 to couple the sugar and the nucleoside via an oxime linkage. The resulting oxime linkage is then reduced utilizing the procedure of Example 28, Step 2 to an iminomethylene linkage and this linkage, in turn, when N-alkylated via the procedure of Example 28, Step 3 will yield compound 33.

EXAMPLE 35
Acetyl 5'-O-Benzoyl-3'-O-Dephosphinico-3'-O-[(Methyimino)methylene]thymidylyl-(3'→5')-3-O-(t-Butyldiphenylsilyl)2,5-Dideoxy-α/β-D-erythro-Pentofuranoside, 34

Compound 33 will be treated with benzoyl chloride according to the procedure of Jenkins, et al., *Synthetic Procedures in Nucleic Acid Chemistry*, Zorbach and Tipson, Ed., Vol. 1, John Wiley & Sons, Pg. 149, to benzoylate the free 5'-hydroxyl of compound 33 which is hydrolyzed and acylated in situ according to the procedure of Baud, et. al, *Tetrahedron Letters* 1990, 31, 4437 to yield compound 34.

EXAMPLE 36
5'-Benzoyl-3'-O-Dephosphinico-3'-O-[(Methylimino)methylene]thymidylyl-(3'→5')-3'-O-(t-Butyldiphenylsilyl)-5'-Deoxythymidine, 35

Compound 34 is reacted with silylated thymine as per the procedure of Baud, et al., *Tetrahedron Letters* 1990, 31, 4437 utilizing dibenzo-18-crown-6 and potassium iodide in acetonitrile-toluene to yield 5'-O-benzoyl-3'-O-dephosphinico-3'-O-[(methylimino)methylene]thymidylyl (3'→5')-3'-O-(t-butyldiphenylsilyl)-5'-deoxythymidine, compound 35 as an anomeric mixture.

EXAMPLE 37
3'-O-Dephosphinico-3'-O-[(Methylimino)methylene]thymidylyl-(3'→5')-3'-O-(t-Butyldiphenylsilyl)-5'-Deoxythymidine, 14

Method C

Compound 35 when treated with methanolic ammonia will also yield compound 14. Further treatment as per the procedure of Example 9 will yield the fully deblocked dimer, from which anomerically pure compound 15 will be isolated by chromatography.

EXAMPLE 38
3'-O-Dephosphinico-3'-O-[(Methylimino)methylene]thymidylyl-(3'→5')-3'-O-(t-Butyldiphenylsilyl)-5'-Deoxyadenosine, 36

Compound 34 is reacted with silylated adenine as per the procedure of Baud, et al., *Tetrahedron Letters* 1990, 31, 4437 utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)methylene]thymidylyl-(3'→5')-3'-O-(t-butyldiphenylsilyl)-5'-deoxyadenosine, 36.

EXAMPLE 39
3'-O-Dephosphinico-3'-O-[(Methylimino) methylene] thymidylyl-(3'→5')-3'-O-(t-Butyldiphenylsilyl)-5'-Deoxycytidine 37

Compound 34 is reacted with silylated cytosine as per the procedure of Baud, et al., *Tetrahedron Letters,* 1990 31, 4437, utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)methylene] thymidylyl-(3'→5')-3'-O-(t-butyldiphenylsilyl)-5'-deoxycytidine, 37.

EXAMPLE 40
3'-O-Dephosphinico-3'-O-[(Methylimino)methylene] thymidylyl-(3'→5')-3'-O-(t-Butyldiphenylsilyl)-5'-Deoxyguanosine 38

Compound 34 is reacted with silylated guanine as per the procedure of Baud, et al., *Tetrahedron Letters* 1990, 31, 4437 utilizing dibenzo-18-crown-6 and potassium iodide in acetonitrile-toluene. Removal of the benzoyl group with methanolic ammonia and chromatographic separation will yield 3'-O-dephosphinico-3'-O-[(methylimino)methylene] thymidylyl-(3'→5')-3'-O-(t-butyldiphenylsilyl)-5'-deoxyguanosine, 38.

EXAMPLE 41
A-(3'→5')-T; A-(3'→5')-A; A-(3'→5')-C; and A-(3'→5')-G 3'-Dephosphinico-3'-(Methylimino)methylene Linked Dimers In a manner analogous to the procedures of Examples 19 and 20, the 5'-(t-butyldimethylsilyl)-3'-O-aminoadenosine intermediate of Example 30 will be reacted with compound 3 to yield a linked nucleoside-sugar compound equivalent to compound 34 wherein Bxi is adenine. The linked nucleoside-sugar intermediate will then be reacted as per the procedures of Examples 21, 23, 24 and 25 to yield the A-T, A-A, A-C and A-G dimers, respectively, of a structure equivalent to that of compound 14 where Bxi is adenine and Bxj is thymine, adenine, cytosine and guanine, respectively.

EXAMPLE 42
C-(3'→5')-T; C-(3'→5')-A; C-(3'→5')-C; and C-(3'→5')-G 3'-Dephosphinico-3'-(Methylimino)methylene Linked Diners In a manner analogous to the procedures of Examples 19 and 20, the 5'-(t-butyldimethylsilyl)-3'-O-aminocytidine intermediate of Example 30 will be reacted with compound 3 to yield a linked nucleoside-sugar compound equivalent to compound 34 wherein Bxi is cytidine. The linked nucleoside-sugar intermediate will then be reacted as per the procedures of Examples 21, 23, 24 and 25 to yield the C-T, C-A, C-C and C-G dimers, respectively, of a structure equivalent to that of compound 14 where Bxi is cytosine and Bxj is thymine, adenine, cytosine and guanine, respectively.

EXAMPLE 43
G-(3'→5')-T; G-(3'→5')-A; G-(3'→5')-C; and G-(3'→5')-G 3'-Dephosphinico-3'-(Methylimino)methylene Linked Dimers In a manner analogous to the procedures of Examples 19 and 20, the 5'-(t-butyldimethylsilyl)-3'-O-aminoguanosine intermediate of Example 30 will be reacted with compound 3 to yield a linked nucleoside-sugar compound equivalent to compound 34 wherein Bxi is guanine. The linked nucleoside-sugar intermediate will then be reacted as per the procedures of Examples 21, 23, 24 and 25 to yield the G-T, G-A, G-C and G-G dimers, respectively, of a structure equivalent to that of compound 14 where Bxi is guanine and Bxj is thymine, adenine, cytosine and guanine, respectively.

EXAMPLE 44
Trimeric, Tetrameric, Pentameric, Hexameric And Other Higher Order Oligonucleosides Having a Selected Nucleoside Sequence The dimers of Examples 21, 23, 24, 25, 26, 27 and 28 are extended by reaction with the 5'-(t-butyldimethylsilyl)-3'-deoxy-3'-[(methyleneamino)oxy]nucleosides, compounds 10, 27, 28 and 29, of Examples 5 and 15 to form trimers utilizing the looping sequence of reactions of Examples 10, 11 and 12. Iteration of this reaction sequence loop adds a further nucleoside to the growing oligonucleoside per each iteration of the reaction sequence loop. The reaction sequence loop of Examples 10, 11 and 12 is repeated "n" number of times to extend the oligonucleoside to the desired "n+1" length. The final 3'-blocked oligonucleoside when treated as per the procedure of Example 9 to remove the terminal 3'-O-(t-butyldiphenylsilyl) blocking group will yield the fully deblocked oligonucleoside of the selected nucleoside sequence and length.

EXAMPLE 45
6'-Amino-6'-Deoxy-5'-Homothymidine, 42; 6'-Amino-2',6'-Dideoxy-5'-Homoadenosine, 43; 6'-Amino-2',6'-Dideoxy-5'-Homocytidine, 44; and 6'-Amino-2',6'-Dideoxy-5'-Homoguanosine, 45 (Via An Intramolecular Free Radical Reaction)

Deblocking of compound 10 is effected by treatment with $Bu_4NF$ in THF. The resulting compound 39 (also reported in Preparation example 4 of European Patent application 0 381 335 A1) will be iodinated upon treatment with methyltriphenoxyphosphonium iodide as per the procedure of Verheyden, et al., *J. Org. Chem.* 1970, 35, 2119 to furnish 5'-deoxy-5'-iodo-3'-O-methyleneamino-thymidine, compound 40. Compound 40 when subjected to an intramolecular free radical reaction according to the procedure of Curran, D. P., Radical Addition Reactions, *In Comprehensive Organic Synthesis*: Trost, B. M. and Fleming I., Eds., vol. 4, p 715–832, Pergamon Press, Oxford (1991), will give the corresponding 3'-O-isoxazolidinethymidine, compound 41 which on DIBAL-H reduction will yield 6'-amino-5'-homothymidine, compound 42 [the 3'-(t-butyldimethylsilyl) derivative of this compound is reported in Rawson, et al., *Nucleosides & Nucleotides* 1990, 9, 89].

When reacted in a like manner compounds 27, 28 and 29 will give 6'-amino-5'-homoadenosine, compound 43; 6'-amino-5'-homocytidine, compound 44; and 6'-amino-5'-homoguanosine, compound 45.

EXAMPLE 46
3'-O-(t-Butyldiphenylsilyl)-5'-Deoxy-5'-C-Allylthymidine 46

A stirred solution of 3'-O-(t-butyldiphenylsilyl)-5'-deoxy-5'-iododthymidine (12, 1.77 g, 3 mmol), allytributyltin (2.97 g, 9 mmol) and AIBN (0.54 g, 3.3 mmol) in dry toluene (30 ml) was degassed completely and heated at 65° C. for 6 hr. The solution was cooled and concentrated under vacuo. The residue was purified by silica gel column chromatography and on elution with hexanes:EtOAc (1:1, v/v) furnished the title compound as homogeneous material. Appropriate fractions were pooled and evaporated to furnish 46, 0.75 g of a white foam, 50% yield. The structure was confirmed by $^1H$ NMR.

EXAMPLE 47

3'-O-(t-Butyldiphenylsilyl)-5'-Deoxy-7'-C-Aldehydothymidine 47

A solution of 46 (1 mmol), $OsO_4$ (0.1 mmol) and n-methylmorpholine oxide (2 mmol) in diethyl ether (4 ml) and water (2 ml) are stirred for 18 hr at room temperature. A solution of $NaIO_4$ (3 ml) is added and the solution further stirred for 12 hr. The aqueous layer is extracted with diethyl ether. Evaporation of the organic layer will give the crude aldehyde 47.

EXAMPLE 48

N3-Benzoyl-1-(5'-O-Dimethoxytrityl-3'-O-Trifluoromethylsulfonyl-threo-Pentofuranosyl)thymine, 50

The method of Horwitz, et al., *J. Org. Chem.* 1964, 29, 2076 will be utilized to prepare the title compound with threo-3'-O-trifluoromethanesulfonate. Also, reaction conditions of Fleet, et al., *Tetrahedron* 1988, 44, 625, will furnish a 3'-leaving group in the threo configuration.

EXAMPLE 49

6'-O-Phthalimida-5'-Homothymidine, 52

To a stirred mixture of 5'-homothymidine [Etzold, et al., *Chemical Communications* 1968, 422] (51, 1.28. g, 5 mmol), N-hydroxyphthalimide (1.09 g, 6.6 mmol) and triphenylphosphine (1.75 g, 6.6 mmol) in dry DMF (25 ml) will be added diisopropylazodicarboxylate (1.5 ml, 7.5 mmol) over a period of 30 min at 0° C. The stirring is continued for 12 hr at room temperature. The solvent is evaporated under vacuo and the residue is washed with diethyl ether (2×50 ml). The residue will then be suspended in hot EtOH (50 ml), cooled and filtered to give the title compound 52.

EXAMPLE 50

6'-O-Phthalimido-3'-O-(t-Butyldiphenylsilyl)-Homothymidine 53

Compound 52 will be treated with t-butyldiphenylchlorosilane in pyridine and imidazole in a standard manner to afford the title compound 53.

EXAMPLE 51

6'-O-Amino-3'-O-(t-Butyldiphenylsilyl)-5'-Homothymidine, 54

To a stirred solution of compound 53 in dry $CH_2Cl_2$ is added methylhydrazine (3 mmol) under anhydrous conditions at room temperature. The solution is stirred for 12 hr, cooled (0° C.) and filtered. The precipitate will be washed with $CH_2Cl_2$ and the combined filtrates will be concentrated. The residue is purified by flash column chromatography (silica gel, 20 g). Elution with $CH_2Cl_2$:MeOH, 9:1, v/v) will furnish the title compound 54.

EXAMPLE 52

3'-De(oxophosphinico)-3'-(iminooxymethylene)-5'-Tritylthymidylyl-(3'→5')-3'-O-(t-Butyldiphenylsilyl)-5'-Deoxythymidine, 55

6'-O-Amino-3'-O-(t-butyldiphenylsilyl)-5'-homothymidine, 54, is converted to the corresponding urethane with ethyl chloroformate ($CH_2Cl_2$-saturated $NaHCO_3$) utilizing the stereospecific conditions of Yang, et al., *J. Am. Chem. Soc.* 1991, 113, 4715. The residue of this reaction will then be stirred in $CH_2Cl_2$ with compound 50. The products are then concentrated in vacuo to yield the dimeric oligonucleoside, compound 55.

EXAMPLE 53

3'-De(oxophosphinico)-3'-[Methyl(iminooxymethylene)]-5'-Tritylthymidylyl-(3'→5')-3'-O-(t-Butyldiphenylsilyl)-5'-Deoxythymidine, 56

Compound 55 will be N-alkylated as per the conditions of Step 3 of Example 4 to yield the N-alkylate iminooxymethylene linked dimeric oligonucleoside 56.

EXAMPLE 54

3'-De(oxophosphinico)-3'-[Methyl(iminooxymethylene)]-5'-Dimethoxytritylthymidylyl-(3'→5')-5'-Deoxythymidine, 57

The 5'-O-trityl and the 3'-O-(t-butyldiphenylsilyl) protecting groups of compound 56 will be removed by treatment with trifluoroacetic acid and the residue dimethoxytritylated as per the procedure of Sproat, B. S. and Lamond, A. I., 2'-O-Methyloligoribonucleotides: Synthesis and Applications, Oligonucleotides and Analogs A Practical Approach, F. Eckstein Ed., IRL Press, pg. 55 (1991), to give the title compound.

EXAMPLE 55

3'-De(oxophosphinico)-3'-[Methyl(iminooxymethylene)]-5-Dimethoxytritylthymidylyl-(3'→5')-3'-[(β-Cyanoethoxy)-N-(diisopropyl)phosphiryl]-5'-Deoxythymidine, 58

Compound 57 (1.89 mmol) will be dissolved in anhydrous dichloromethane under an argon atmosphere.

Diisopropylethylamine (0.82 ml, 4.66 mmol) is added and the reaction mixture cooled to ice temperature. Chloro (diisopropylamino)-β-cyanoethoxyphosphine (0.88 ml, 4.03 mmol) is added to the reaction mixture and the reaction mixture is allowed to warm to 20° C. and stirred for 3 hr. Ethylacetate (80 ml) and triethylamine (1 ml) are added and the solution is washed with brine solution three times (3×25 ml). The organic phase is separated and dried over magnesium sulfate. After filtration of the solids the solvent is evaporated in vacuo at 20° C. to an oil that will then be purified by column chromatography using silica and a solvent such as hexane-ethyl acetate-triethylamine (50:40:1) as eluent. The fractions are then evaporated in vacuo and the residue will be further evaporated with anhydrous pyridine (20 ml) in vacuo (1 torr) at 26° C. in the presence of sodium hydroxide for 24 hr to yield the title compound 58.

EXAMPLE 56

5'-Amino-5'-Homothymidine, 60

5'-Amino-3'-O-(t-butyldimethylsilyl)-5'-homothymidine 59 is prepared as per Rawson, et al., *Nucleosides & Nucleotides* 1990, 9, 89. The t-butyldimethylsilyl group will be removed as per the procedure of Step 4 of Example 4 to give the title compound.

EXAMPLE 57

5'-Methylamino-3'-O-(t-Butyldiphenylsilyl)-5'-Homothymidine, 62

Compound 60 is t-butyldiphenylsilated as per the procedure of 37 to give 5'-Amino-3'-O-(t-butyldiphenysilyl)-5'-homothymidine, compound 61, which will then be treated as per the procedure of Step 3 of Example 4 alkylate the 5'-amino group to yield the title compound 62.

EXAMPLE 58

3'-Dephosphinico-3'-S-[(Methylimino)methylene]-5'-Monomethoxytrityl-3'-Thiathymidylyl-(3'→5')-3'-(t-Butyldiphenylsilyl)-5'-Deoxythymidine, 64

5'-Methylamino-3'-O-(t-butyldiphenylsilyl)-5'-homothymidine 62 (1 mmol) will be added to aqueous sodium hypochloride (4 mmol) to furnish a chloramide intermediate.

The chloramide intermediate is cooled (0° C.) and treated with 5'-O-monomethoxytrity-3'-thiothymidine (0.9 mmol), compound 63, prepared as per Cosstick, et al., *Nucleic Acids Res.* 1990, 18, 829. The reaction mixture is worked up utilizing the procedure of Barton, et al., *J. Org. Chem.* 1991, 56, 6702 and the residue will be purified by chromatography to give the title compound 64.

EXAMPLE 59

3'-Dephosphinico-3'-S-[(Methylimino)methylene]-5'-Monomethoxytrityl-3'-Thiothymidylyl-(3'→5')-5'-Deoxythymidine, 65

Compound 64 will be deblocked at the terminal 3' position utilizing the as per the procedure of Step 4 of Example 4 to give compound 65.

EXAMPLE 60

3'-Dephosphinico-3'-S-[(Methylimino)methylene]-5'-Monomethoxytrityl-3'-Thiothymidylyl-(3'→5')-3-[(β-Cyanoethoxy)-N-(diisopropyl)phosphortityl]-5'-Deoxythymidine 66

Compound 65 will be phosphitylated as per the procedure of Example 55 to give the title compound 66.

EXAMPLE 61

5'-O-t-Butyldimethylsilyl)-3'-De(oxyphosphinico)-3'-(Imino-1,2-Ethanediyl)thymidylyl-(3'→5')3'-O-(t-Butyldiphenylsilyl)-5'-Deoxythymidine, 68

3'-Amino'-5'-O-(t-butyldimethylsilyl)-3'-deoxythymidine, compound 67, prepared according to Matsuda, et al., *Nucleoside & Nucleotides* 1990, 9, 587 will be reductively coupled with compound 47 in the presence of a catalytic amount of acid as per the procedure of Magid, et. al, *Tettrahedron Letters.* 1990, 31, 5595, to yield the Schiff's base intermediate that is reduced in situ to give the amino linkage of the title compound 68.

EXAMPLE 62

3'-De(oxyphosphinico)-3'-[(Methylimino)-1,2-Ethanediyl]thymidylyl-(3'→5')-3'-O-(t-Butyldiphenylsilyl)-5'-Deoxythymidine, 69

Compound 68 will be methylated and deblocked at the 5' position as per the procedure of Step 3 of Example 4 to yield the N-alkylated 5'-deblocked dimer, compound 69.

EXAMPLE 63

3'-De(oxyphosphinico)-5'-Dimethoxytrityl-3'-[(Methylimino)-1,2-Ethanediyl]thymidylyl-(3'→5')-3'-O-(t-Butyldiphenylsilyl)-5'-Deoxythymidine, 70

Compound 69 will be dimethoxytritylated as per the procedure of Sproat, B. S. and Lamond, A. I., 2'-O-Methyloligoribonucleotides: Synthesis and Applications, Oligonucleotides and Analogs A Practical Approach, F. Eckstein Ed., IRL Press, 1991, pg. 55.

EXAMPLE 64

3'-De(oxyphosphinico)-5'-Dimethoxytrityl-3'-[(Methylimino)-1,2-Ethanediyl]thymidylyl-(3'→5')-5'-Deoxythymidine, 71

The dimethoxytritylated intermediate, compound 70 when deblocked at the 3' terminus as per the procedure of Step 4 of Example 4 will give compound 71.

EXAMPLE 65

3'-De(oxyphosphinico)-5'-Dimethoxytrityl-3'-[(Methylimino)-1,2-Ethanediyl]thymidylyl-(3'→5')-3'-[(β-Cyanoethoxy)-N-(diisopropyl)phosphiryl]-5'-Deoxythymidin, 72

Compound 71 will be phosphitylated as per the procedure of Example 55 to give the title compound 72.

EXAMPLE 66

2'-O-Methylhomoadenosine, 74

Homoadenosine, 73, prepared as per the procedure of Kappler, F. and Hampton, A., *Nucleic Acid Chemistry, Part 4*, Ed. L. B. Townsend and R. S. Tipson, Wiley-Interscience Publication, 1991, pg. 240, will be blocked across its 3' and 5' hydroxyl groups with a TIPS, i.e., tetraisopropylsilyl, blocking group followed by alkylation as per the procedures described in U.S. patent applications Ser. No. 566,977, filed Aug. 13, 1990 and PCT/US91/05720, filed Aug. 12, 1991. Removal of the TIPS group with tetra-n-butylammonium fluoride as per the procedure of Step 4 of Example 4 will yield the title compound 74.

EXAMPLE 67

6'-O-Amino-3'-O-(t-Butyldiphenylsilyl)-5'-Homoadenosine, 75

Compound 74 will be treated as per the procedures of Examples 36, 37 and 38 to yield the title compound 75.

EXAMPLE 68

3'-De(oxophosphinico)-3'-(Iminooxymethylene)-5'-Dimethoxytritylthymidylyl-(3'→5')-3'-O-(t-Butyldiphenylsilyl)-5'-Deoxy-2'-O-Methyladenosine, 76

Compound 75 will be treated and reacted with compound 50 as per the procedure of Example 65 to yield the title compound 76.

EXAMPLE 69

3'-De(oxophosphinico)-3'-[Methyl(iminooxymethylene)]-5-Dimethoxytritylthymidylyl-(3'→5')-3'-[(β-Cyanoethoxy)-N-(Diisopropyl)phosphiryl]-5'-Deoxy-2'-O-Methyladenosine, 77

Compound 76 will be reacted as per the reaction sequence of Examples 40, 41 and 42 to yield the title compound 77.

EXAMPLE 70

6'-O-Amino-3'-O-(t-Butyldiphenylsilyl)-2'-Deoxy-5'-Homoaristeromycin, 79

(−)-2'-Deoxy-5'-homoaristeromycin, compound 78, (the carbocyclic analog of 5'-homo-2'-deoxyadenosine) is prepared as per the procedure of Jones, et al., *J. Chem. Soc. Perkin Trans.* 1988, 1, 2927. Compound 78 will be treated as per the procedure of Examples 36, 37 and 38 to yield the 6'-O-amino-3'-blocked carbocyclic analog of 5'-homo-2'-deoxyadenosine, compound 79.

EXAMPLE 71

3'-De(oxophosphinico)-3'-(Iminooxymethylene)-5'-Dimethoxytritylthymidylyl-(3'→5')-3'-O-(t-Butyldiphenylsilyl)-2',5'-Dideoxyaristeromycin, 80

Compound 79 will be treated and reacted with compound 50 as per the procedure of Example 65 to yield the title compound 80.

EXAMPLE 72

3'-De(oxophosphinico)-3'-[Methyl(iminooxymethylene)]-5'-Dimethoxytritylthymidylyl-(3'→5')-3'-[(β-Cyanoethoxy)-N-(Diisopropyl)phosphiryl]-2',5'-Dideoxyaristeromycin, 81

Compound 80 will be reacted as per the reaction sequence of Examples 40, 41 and 42 to yield the title compound 81.

EXAMPLE 73
6'-O-Amino-2'-O-Butyl-5'-Homoaristeromycin, 82

(−)-5'-Homoaristeromycin, compound 78, will be blocked with a TIPS group, alkylated and deblocked as per the procedure of Example 70 to yield compound 82.

EXAMPLE 74
6'-O-Amino-3'-O-(t-Butyldiphenylsilyl)-2'-O-Butyl-5'-Homoaristeromycin, 83

Compound 82 will be treated as per the procedures of Examples 36, 37 and 38 to yield the title compound 83.

EXAMPLE 75
3'-De(oxophosphinico)-3'-(Iminooxymethylene)-5'-Dimethoxytritylthymidylyl-(3'→5')-3'-O-(t-Butyldiphenylsilyl)-2'-O-Butyl-5'-Deoxyaristeromycin, 84

Compound 83 will be treated and reacted with compound 50 as per the procedure of Example 65 to yield the title compound 84.

EXAMPLE 76
3'-De(oxophosphinico)-3'-[Methyl(iminooxymethylene)]-5'-Dimethoxytritylthymidylyl-(3'→5')-3'-[(β-Cyanoethoxy)-N-(Diisopropyl)phosphiryl]-2'-O-Butyl-5'-Deoxyaristeromycin, 85

Compound 84 will be reacted as per the reaction sequence of Examples 40, 41 and 42 to yield the title compound 85.

EXAMPLE 77
(+)-1-[(1R,3S,4S)-3-Azido-5-Dimethoxytrityl-4-(Hydroxymethyl)-Cyclopentyl]-5-Methyl-2,4-(1H,3H)-Pyrimidindione, 87

(+)-1-[1R,3S,4S)-3-Azido-4-(hydroxymethyl)-cyclopentyl]-5-methyl-2,4-(1H,3H)-pyrimidindione, compound 86, prepared as per the procedure of Bodenteich, et al., *Tetrahedron Letters* 1987, 28, 5311, will be dimethoxytritylated utilizing dimethoxytrityl chloride in pyridine at room temperature to give the title compound 87.

EXAMPLE 78
(+)-1-[(1R,3S,4S)-3-Amino-4-(Dimethoxytrityloxymethyl)Cyclopentyl]-5-Methyl-2,4-(1H,3H)-Pyrimidindione, 88

Compound 87 will be reduced with $Ph_3P$ in pyridine at room temperature as per the procedure of Hronowski, et al., *J. Chem. Soc., Chem. Commun.* 1990, 1547, to give the carbocyclic analog of 3'-amino-5'-dimethoxytrityl thymidine, compound 88.

EXAMPLE 79
1-{(1R,3S,4S)-3-[Imino-2-(5'-Deoxythymidylyl-5'-yl)-1,2-Ethanediyl]-4-(Dimethoxtrityloxymethyl)-Cyclopentyl}-5-Methyl-2,4-(1H,3H)-Pyrimidindione, 89

Compound 88 will be reacted with compound 47 as per the procedure of Example 74 to yield the title compound 89.

EXAMPLE 80
Synthesis Of Oligonucleotides Using A DNA Synthesizer

Solid support oligonucleotide and "oligonucleotide like" syntheses are performed on an Applied Biosystems 380 B or 394 DNA synthesizer following standard phosphoramidite protocols and cycles using reagents supplied by the manufacture. The oligonucleotides are normally synthesized in either a 10 pmol scale or a 3×1 μmol scale in the "Trityl-On" mode. Standard deprotection conditions (30% $NH_4OH$, 55° C., 16 hr) are employed. HPLC is performed on a Waters 600E instrument equipped with a model 991 detector. For analytical chromatography, the following reverse phase HPLC conditions are employed: Hamilton PRP-1 column (15×2.5 cm); solvent A: 50 mm TEAA, pH 7.0; solvent B: 45 mm TEAA with 80% $CH_3CN$; flow rate: 1.5 ml/min; gradient: 5% B for the first 5 minutes, linear (1%) increase in B every minute thereafter.

For preparative purposes, the following reverse phase HPLC conditions are employed: Waters Delta Pak Waters Delta-Pak $C_4$ 15 μm, 300A, 25×100 mm column equipped with a guard column of the same material; column flow rate: 5 ml/min; gradient: 5% B for the first 10 minutes, linear 1% increase for every minute thereafter. Following HPLC purification, oligonucleotides are detritylated and further purified by size exclusion using a Sephadex G-25 column.

EXAMPLE 81
Higher Order Mixed Oligonucleosides-Oligonucleosides and Mixed Oligonucleosides-Oligonucleotides A. Solution Phase Synthesis Of 3'-De(oxophosphinico)-3'-[Methyl(iminooxymethylene)]-Thymidylyl-(3'→5')-5'-Deoxythymidylyl-3'-Phosphorothioate-Thymidylyl-(3'→5')-3'-De(oxyphosphinico)-3'-[(Methylimino)-1,2-Ethanediyl]thymidylyl-(3'→5')-3'-O-(t-Butyldiphenylsilyl)-5'-Deoxythymidine, 90, A Mixed Oligonucleoside-Oligonucleotide-Oligonucleoside Polymer Incorporating A Nucleotide Linkage Flanked At Its 5' Terminus By A 3'-De(oxophosphinico)-3'-[Methyl(iminooxymethylene)] Linked oligonucleoside Dimer and At Its 3' Terminus By A 3'-De(oxyphosphinico)-3'-[(Methylimino)-1,2-Ethanediyl] Linked Oligonucleoside Dimer A mixed oligonucleoside-oligonucleotide-oligonucleoside having a 3'-de(oxophosphinico)-3'-[methyl(iminooxymethylene)] linked oligonucleoside dimer and a 3'-de(oxyphosphinico)-3'-[(methylimino)-1,2-ethanediyl] linked oligonucleoside diner coupled together via a phosphorothioate nucleotide linkage will be prepared by reacting compound 58, compound 70 and tetrazole in anhydrous acetonitrile under argon. The coupling reaction will be allowed to proceed to completion followed by treatment with Beaucage reagent and ammonium hydroxide removal of the dimethoxytrityl blocking group according to the procedure of Zon, G. and Stec, W. J., *Phosphorothioate oligonucleotides, oligonucleotides and Analogs A Practical Approach*, F. Eckstein Ed., IRL Press, pg. 87 (1991). The 3' blocking group will then be removed as per the procedure of Step 3 of Example 4 and the product purified by HPLC to yield the title compound 90, wherein utilizing the structure of Scheme XVI, $T_3$ and $T_5$ are OH, D is S, E is OH, X is H, Q is O, r is 0 and q is 2; and for each q, i.e., $q_1$ and $q_2$, n and p are 1 in each instance; and for $q_1$, m is 1; and for $q_2$, m is 0; and Bxj and Bxi are thymine.

B. Solid Support Synthesis of 3'-De(oxophosphinico)-3'-[Methyl(iminooxymethylene)]-Thymidylyl(3'→5')-5'-Deoxythymidylyl-(3'→5')-P-Thymidylyl-3-De(oxophosphinico)-3'-[Methyl(iminooxymethylene)]-(3'→5') Thymidylyl-(3'→5')-P-Thymidylyl-3'-De(oxophosphinico)-3'[Methyl(iminooxymethylene)]-(3'→5')-Thymidylyl-(3'→5')-P-2'-Deoxycytidine, 91, A Mixed Oligonucleotide-Oligonucleoside Polymer Incorporating 3'-De(oxophosphinico)-3'-[Methyl(iminooxymethylene)] Linked oligonucleoside Dimers Flanked By Conventional Linked Nucleotides The dimeric oligonucleoside 58 will be utilized as building block units in a conventional oligonucleotide solid support synthesis as per the procedure of Example 80. For the purpose of illustration a polymer incorporating seven nucleosides is described. A first unit of the dimeric oligonucleoside 58 will be coupled to a first cytidine nucleoside tethered to a solid support via its 3' hydroxyl group and having a free 5' hydroxyl group. After attachment of the first unit of compound 58 to the support, the 5'-dimethoxytrityl group of that first compound 58 unit will be removed in the normal manner. A second compound 58 unit will then be coupled via its β-cyanoethyl-N-diisopropylphosphiryl group to the first compound 58 unit using normal phosphoramidate chemistry. This forms a conventional phosphodiester bond between the first and second compound 58 units and elongates the polymer by two nucleosides (or one oligonucleoside dimer unit). The dimethoxytrityl blocking group from the second compound 58 unit will be removed in the normal manner and the polymer elongated by a further dimeric unit of compound 58. As with addition of the first and second dimeric units, the third unit of compound 58 is coupled to the second via conventional phosphoramidite procedures. The addition of the third unit of compound 58 completes the desired length and base sequence. This polymer has a backbone of alternating normal phosphodiester linkages and the methyl(iminooxymethylene) linkages of compound 58. The 5' terminal dimethoxytrityl group of the third compound 58 unit will be removed in the normal manner followed by release of the polymer from the solid support, also in the normal manner. Purification of the polymer will be achieved by HPLC to yield compound 91 wherein, utilizing the structure of Scheme XVI, $T_3$ and $T_5$ are OH, D is O, E is OH, X is H, Q is O, r is 1 and for the seven nucleoside polymer described, q is 3; and for each q, i.e., $q_1$, $q_2$ and $q_3$, n and p are 1 in each instances; and for $q_1$ and $q_2$, m is 1; and for $q_3$, m is 0; and Bxk is cytosine; and each BxJ and Bxi is thymine.

EXAMPLE 82
3'-Deoxy-3'-C-formyl-5'-O-t-butyldiphenylsilyl-thymidine

A mixture of thymidine (400 g, and 1.65 mol), 4-dimethylaminopyridine (0.8 g, 6.5 mmol) and t-butyldiphenylchlorosilane (347.2 g, 1.26 mol) in anhydrous pyridine (3.0 lt) was stirred at room temperature for 48 hr. To the stirred reaction mixture two lots of t-butyldiphenyl chlorosilane (129.4 g, 0.47 mol and 22.7 g, 0.082 mol) were added 12 hr. apart and stirring continued for an additional 48 hr. The reaction mixture was concentrated under vacuum and the residue redissolved in ethanol (2.5 lt). The product was precipitated by pouring the reaction mixture into a cold stirred ice-water (5.0 lt) suspension. The aqueous suspension was stirred at room temperature for 3 hr. to quench traces of unreacted chlorosilane. The granular white precipitate was filtered and washed with distilled water (5×1 it) and air dried to furnish 876 g of 5'-O-t-butyldiphenylsilyl thymidine (slightly contaminated with bissilyated product, about 5%).

The impurity was removed by suspending finely powdered 5'-O-t-butyldiphenylsilyl thymidine in ether (600 ml) and pouring into stirred hexanes (1.5 lt).

The hexanes:ether slurry was stirred for 1 hr and filtered to furnish 5'-O-t-butyldiphenylsilyl thymidine as fine white solid. The product was free of bissilyated impurity (judged by tiC; EtOAC:hexanes, 1:1, v/v) and on drying under vacuum furnished 718.9 g (90.7%) of 5'-O-t-butyldiphenylsilyl thymidine, which was pure according to thin-layer chromatography. $^1$HNMR (DCl$_3$) d 1.0 (s, 9H, t BuH), 1.62 (s, 3H, C5, CH$_3$), 2.3 (m, 2H, C2, CH$_2$), 2.7 (br S, 1H, 3'OH), 3.8–4.1 (m, 3H, C4, H and (5'CH$_a$), 4.6 (m, 1H, 3'H), 6.45 (5, 1H, 1'H), 7.36–7.67 (m, 11H, (6H and Ar H), and 9.05 (br S, 1H, NH).

To a suspension of 5'-O-i-butyldiphenylsilylthymidine (96.0 g, 0.2 mol) in dry toluene (1.1 lt) was added pyridine (19.15 g, 0.24 mol) and N-hydroxysuccimidine (4.6 g, 0.039 mol). The mixture was stirred at 55° C. under arogon while a solution of phenylchlorothioanoformate (38.28 g, 0.22 mol in dry toluene, 100 ml) was added dropwise over a period of 1 hr. The internal temperature of the reaction mixture rose to 70° C. while it became clear. After 24 hr, the reaction mixture pyridine (1.6 g, 0.02 mol) followed by phenylchlorothionoformate (3.48 g, 0.02 mol) were added. The stirring was continued at room temperature for 24 hr. The resulting pyridinium hydrochloride salt was precipitated by addition of ether (400 ml) and filtered again. The filtrate was concentrated under vacuum and the residue was used for subsequent radical reaction without any further purification.

A mixture of the 5'-O-t-butyl diphenylsilyl-3'-O-phenoxythiocarbonyl-thymidine (152.8 g, 0.24 mol), tri-n-butyltin styrene (245 g, 0.62 mol) and aza-bis (isobutyronitrile) (5.95 g, 0.036 mol) in dry benzene (800 ml) were degassed with argon (3 times) and heated at 75° C. for 8 hr while stirring. Over next 60 hr, AIBN (6×5.95 g, 0.036 mol) was added in portions to the reaction mixture under argon and stirring was continued at 75° C. After completion of the reaction (about 70–80 hr; detected by complete consumption of the 5'-O-t-butyl diphenylsilyl-3'-O-phenoxythiocarbonyl-thymidine), the solution was cooled to room temperature and transferred on the top of a pre-packed silica gel (1 mg) column. Elution with EtOAC:Hexanes (7:5, v/v) gave the desired 3'-styryl nucleoside as homogenous material. Appropriate fractions were pooled and evaporated to furnish 67.49 (49.5%) of the 3'-styryl nucleoside as an oil. $^1$HNMR (CDCl$_3$) d 1.1 (S, 9H, tBu-H), 1.60 (S, 3H, C$_5$CH$_3$), 2.4 (m, 2H, C$_2$,CH$_2$) 3.25 (m, 1H, C$_3$,H), 3.8 (m, 1H, C4'H), 4.15 (m, 2H, ($_{5'}$ CH$_2$), 6.21 (dd, 1, C$_{1'}$, H), 6.0 and 6.5 (2m, 2H, CH=CH-ph), 7.3–7.7 (m, 11H, C$_6$H, and Ar H), 8.8 (S, 1H, OH).

A mixture of the 3'-styryl nucleoside (2.19 g, 3.86 mmol), N-methyl morpholine-N-oxide (0.68 g, 5.6 mmol), OsO$_4$ (3.9 ml of 2.5% solution in t-BuOH, 0.38 mmol) in dioxane: water (30 ml, 2:1) was stirred at room temperature. The reaction mixture was protected from light and stirred for 1 hr. To the dark colored reaction mixture NaIO$_4$ (1.82 g, 8.5 mmol) in water (8 ml) was added in one portion and stirring continued for 3 hr. After completion of the reaction, the reaction mixture was diluted with EtOAC (100 ml) and extracted with saturated NaCl solution (3×60 ml). The organic layer was dried (MgSO$_4$) and concentrated to furnish oily residue. The residue was purified by silica gel column chromatography to furnish 0.94 (50%) of 5'-O-t-butyldiphenylsilyl-3'-c-formylthymidine as white foam. $^1$HNMR (CDCl$_3$) d 1.1 (s, 9H, t-BuH), 1.61 (S, 3H, C$_5$ CH$_3$), 2.3 and 2.75 (2m, 2H, C2, CH$_2$), 3.4 (m, 1H, C$_{3'}$, H), 4.0 (m, 2H, C$_{5'}$, CH$_2$), 4.35 (m, 1H, C$_{4'}$H), 6.11 (t, 1, C$_{1'}$H), 7.26–7.67 (m, 11H, C$_6$H, Ar H), 8.2 (brS, 1H, NH), and 9.70 (s, 1H, CHO).

EVALUATION
PROCEDURE 1—Nuclease Resistance

A. Evaluation of the resistance of oligonucleotide-mimicking macromolecules to serum and cytoplasmic nucleases.

Oligonucleotide-mimicking macromolecules of the invention can be assessed for their resistance to serum nucleases by incubation of the oligonucleotide-mimicking macromolecules in media containing various concentrations of fetal calf serum or adult human serum. Labelled oligonucleotide-mimicking macromolecules are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide-mimicking macromolecules it is possible to determine the effect on nuclease degradation by the particular modification. For the cytoplasmic nucleases, an HL 60 cell line can be used. A post-mitochondrial supernatant is prepared by differential centrifugation and the labelled macromolecules are incubated in this supernatant for various times. Following the incubation, macromolecules are assessed for degradation as outlined above for serum nucleolytic degradation. Autoradiography results are quantitated for evaluation of the macromolecules of the invention. It is expected that the macromolecules will be completely resistant to serum and cytoplasmic nucleases.

B. Evaluation of the resistance of oligonucleotide-mimicking macromolecules to specific endo- and exo-nucleases.

Evaluation of the resistance of natural oligonucleotides and oligonucleotide-mimicking macromolecules of the invention to specific nucleases (ie, endonucleases, 3',5'-exo-, and 5',3'-exonucleases) can be done to determine the exact effect of the macromolecule linkage on degradation. The oligonucleotide-mimicking macromolecules are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the macromolecules linkage are determined for specific nucleases and compared with the results obtained from the serum and cytoplasmic systems. As with the serum and cytoplasmic nucleases, it is expected that the oligonucleotide-mimicking macromolecules of the invention will be completely resistant to endo- and exo-nucleases.

PROCEDURE 2—5-Lipoxygenase Analysis and Assays

A. Therapeutics

For therapeutic use, an animal suspected of having a disease characterized by excessive or abnormal supply of 5-lipoxygenase is treated by administering the macromolecule of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotide-mimicking macromolecules of this invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 300° to about 500° C. The cleaved 5-lipoxygenase RNA can be analyzed by agarose gel electrophoresis and hybridization with radiolabeled DNA probes or by other standard methods.

C. Diagnostics

The oligonucleotide-mimicking macromolecules of the invention will also be useful in diagnostic applications, particularly for the determination of the expression of specific mRNA species in various tissues or the expression of abnormal or mutant RNA species. In this example, while the macromolecules target a abnormal mRNA by being designed complementary to the abnormal sequence, they would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the MRNA would bind to the solid support. The 3' region of the abnormal RNA, which is cleaved, would not be bound to the support and therefore would be separated from the normal mRNA.

Targeted MRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various knowns agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotide-mimicking macromolecules which interfere with 5-lipoxygenase synthesis in these cells.

A second test system for oligonucleotide-mimicking macromolecules makes use of the fact that 5-lipoxygenase is a "suicide" enzyme in that it inactivates itself upon reacting with substrate. Treatment of differentiated HL-60 or other cells expressing 5 lipoxygenase, with 10 $\mu$M A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotide-mimicking macromolecules can exert on intact cells and which can be easily be quantitated is specific inhibition of 5-lipoxygenase protein synthesis. To perform this technique, cells can be labelled with $^{35}$S-methionine (50 ACi/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 μM, 10 μM, and 30 μM of the macromolecules of the invention for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 μM $^{14}$C-arachidonic acid, 2 mM ATP, 50 μM free calcium, 100 μg/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 μM, 10 μM, and 30 μM would be as follows. Control cells oxidize 200 pmol arachidonic acid/5 min/10$^6$ cells. Cells treated with 1 μM, 10 μM, and 30 μM of an effective oligonucleotide-mimicking macromolecule would oxidize 195 pmol, 140 pmol, and 60 pmol of arachidonic acid/5 min/10$^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris·HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 μL in the microtiter wells for 90 min. The antibodies are prepared by immunizing rabbits with purified human recombinant 5-lipoxygenase. The wells are washed with TBS containing 0.05% tween 20 (TBST), then incubated with 100 μL of a 1:1000 dilution of peroxidase conjugated goat anti-rabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer oligonucleotide-mimicking macromolecule at 1 μM, 10 μM, and 30 μM would be 30 ng, 18 ng and 5 ng of 5-lipoxygenase per 10$^6$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells (2×10$^5$ cells/mL) will be treated with increasing concentrations of the macromolecule for 48–72 hours in the presence of 1.3% DMSO. The cells are washed and resuspended at a concentration of 2×10$^6$ cell/mL in Dulbecco's phosphate buffered saline containing 1% delipidated bovine serum albumin. Cells are stimulated with 10 μM calcium ionophore A23187 for 15 min and the quantity of LTB4 produced from 5×10$^5$ cell determined by radioimmunoassay as described by the manufacturer.

Using this assay the following results would likely be obtained with an oligonucleotide-mimicking macromolecule directed to the 5-LO MRNA. Cells will be treated for 72 hours with either 1 μM, 10 μM or 30 μM of the macromolecule in the presence of 1.3% DMSO. The quantity of LTB$_4$ produced from 5×10$^5$ cells would be expected to be about 75 pg, 50 pg, and 35 pg, respectively with untreated differentiated cells producing 75 pg LTB$_4$.

E. In Vivo Assay

Inhibition of the production of 5-lipoxygenase in the mouse can be demonstrated in accordance with the following protocol. Topical application of arachidonic acid results in the rapid production of leukotriene B$_4$, leukotriene C$_4$ and prostaglandin E$_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene B$_4$ produced in biopsy specimens is performed as a direct measurement of 5-lipoxygenase activity in the tissue. oligonucleotide-mimicking macromolecules will be applied topically to both ears 12 to 24 hours prior to administration of arachidonic acid to allow optimal activity of the compounds. Both ears are pretreated for 24 hours with either 0.1 μmol, 0.3 μmol, or 1.0 μmol of the macromolecule prior to challenge with arachidonic acid. Values are expressed as the mean for three animals per concentration. Inhibition of polymorphonuclear cell infiltration for 0.1 μmol, 0.3 μmol, and 1 μmol is expected to be about 10%, 75% and 92% of control activity, respectively. Inhibition of edema is expected to be about 3%, 58% and 90%, respectively while inhibition of leukotriene B$_4$ production would be expected to be about 15%, 79% and 99%, respectively.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having the structure:

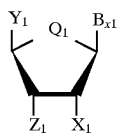

wherein:

$Z_1$ is C(O)H, $CH_2C(O)H$, $CH_2R_ANH_2$, or $R_ANH_2$;

$R_A$ is O or $NR_1$;

$Y_1$ is hydroxymethyl, a nucleoside attached via a linking group, a nucleotide, an oligonucleotide, an oligonucleoside, or a hydroxyl-protected or amine-protected derivative thereof;

$R_1$ is H; alkyl or substituted alkyl having 1 to about 10 carbon atoms; alkenyl or substituted alkenyl having 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms;

$B_{X1}$ is a nucleosidic base;

$Q_1$ is O, S, or $CH_2$; and $X_1$ is H; OH; alkyl or substituted alkyl having 1 to about 10 carbon atoms; alkaryl, substituted alkaryl, aralkyl, or substituted aralkyl having 7 to about 14 carbon atoms; F; Cl; Br; CN; $CF_3$; $OCF_3$; OCN; O-alkyl; S-alkyl; N-alkyl; O-alkenyl; S-alkenyl; N-alkenyl; $SOCH_3$; $SO_2C_3$; $ONO_2$; $NO_2$; $N_3$; $NH_2$; heterocycloalkyl; heterocycloalkaryl; aminoalkylamino; or polyalkylamino or substituted silyl.

2. The compound of claim 1 wherein $R_A$ is O.

3. The compound of claim 1 wherein $R_A$ is NH.

4. The compound of claim 1 wherein $Z_1$ is C(O)H or $CH_2C(O)H$.

5. The compound of claim 1 wherein $Z_1$ is $CH_2R_ANH_2$ or $R_ANH_2$.

6. The compound of claim 1 wherein $Y_1$ is hydroxymethyl.

7. The compound of claim 1 wherein $Y_1$ is an oligonucleotide or an oligonucleoside.

8. The compound of claim 1 wherein $X_1$ is H or OH.

9. The compound of claim 1 wherein $X_1$ is alkyl or substituted alkyl having 1 to about 10 carbon atoms.

10. The compound of claim 1 wherein $X_1$ is F.

11. A compound having the structure:

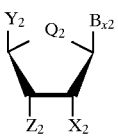

wherein:

$Y_2$ is C(O)H, $CH_2C(O)H$, $CH_2R_ANH_2$, or $R_ANH_2$;

$R_A$ is O or $NR_1$;

$Z_2$ is hydroxymethyl, a nucleoside attached via a linking group, a nucleotide, an oligonucleotide, an oligonucleoside, or a hydroxyl-protected or amine-protected derivative thereof;

$R_1$ is H; alkyl or substituted alkyl having 1 to about 10 carbon atoms; alkenyl or substituted alkenyl having 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms;

$B_{X1}$ is a nucleosidic base;

$Q_2$ is O, S, or $CH_2$; and $X_2$ is H; OH; alkyl or substituted alkyl having 1 to about 10 carbon atoms; alkaryl, substituted alkaryl, aralkyl, or substituted aralkyl having 7 to about 14 carbon atoms; F; Cl; Br; CN; $CF_3$; $OCF_3$; OCN; O-alkyl; S-alkyl; N-alkyl; O-alkenyl; S-alkenyl; N-alkenyl; $SOCH_3$; $SO_2CH_3$; $ONO_2$; $NO_2$; $N_3$; $NH_2$; heterocycloalkyl; heterocycloalkaryl; aminoalkylamino; or polyalkylamino or substituted silyl.

12. The compound of claim 11 wherein $R_A$ is O.

13. The compound of claim 11 wherein $R_A$ is NH.

14. The compound of claim 11 wherein $Y_2$ is C(O)H or $CH_2C(O)H$.

15. The compound of claim 11 wherein $Y_2$ is $CH_2R_ANH_2$ or $R_ANH_2$.

16. The compound of claim 11 wherein $Z_2$ is hydroxymethyl.

17. The compound of claim 11 wherein $Z_2$ is an oligonucleotide or an oligonucleoside.

18. The compound of claim 11 wherein $X_2$ is H or OH.

19. The compound of claim 11 wherein $X_2$ is alkyl or substituted alkyl having 1 to about 10 carbon atoms.

20. The compound of claim 11 wherein $X_2$ is F.

* * * * *

UNITED STATES PATENT AND TRADEMARK OFFICE
CERTIFICATE OF CORRECTION

PATENT NO.   : 5,808,023
DATED        : September 15, 1999
INVENTOR(S)  : Yogesh S. Sanghvi et al.

It is certified that error appears in the above-identified patent and that said Letters Patent is hereby corrected as shown below:

Column 9,
Line 15, after "support" next line starting with "Moffatt, et al" should not begin a new paragraph.

Column 10
Line 34, "=13" is not in the specification.

Column 36,
Line 58, "$CH_3$ - 5" should be -- $CH_2$-5 --.

Column 38,
Line 30, "diner" should be -- dimer --.
Line 31, "diner" should be -- dimer --.

Column 40,
Line 19, "(h," should be -- (s, --.

Column 41,
Line 53, "witig" should be -- Witig --.

Column 49,
Line 62, "pmol" should be -- μmol --.

Column 50,
Line 32, "diner" should be dimer --.

Column 51,
Line 45, "(5x1 it)" should be -- (5x1 1t) --.
Line 54, "tiC" should be -- t1C --.

UNITED STATES PATENT AND TRADEMARK OFFICE
CERTIFICATE OF CORRECTION

PATENT NO.    : 5,808,023
DATED         : September 15, 1999
INVENTOR(S)   : Yogesh S. Sanghvi et al.

It is certified that error appears in the above-identified patent and that said Letters Patent is hereby corrected as shown below:

Column 54,
Line 59, "(50ACi/ml)" should be -- 50μCi/ml --.

Column 56,
Line 46, "oligonucleotide" should be -- Oligonucleotide -- beginning of a new sentence.

Signed and Sealed this

Thirteenth Day of August, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

| | | |
|---|---|---|
| PATENT NO. | : 5,808,023 | |
| APPLICATION NO. | : 08/335046 | |
| DATED | : September 15, 1998 | |
| INVENTOR(S) | : Yogesh S. Sanghvi et al. | |

It is certified that error appears in the above-identified patent and that said Letters Patent is hereby corrected as shown below:

Column 9,
Line 15, after "support" next line starting with "Moffatt, et al" should not begin a new paragraph.

Column 10
Line 34, "=13" is not in the specification.

Column 36,
Line 58, "$CH_3$ - 5" should be -- $CH_2$-5 --.

Column 38,
Line 30, "diner" should be -- dimer --.
Line 31, "diner" should be -- dimer --.

Column 40,
Line 19, "(h," should be -- (s, --.

Column 41,
Line 53, "witig" should be -- Witig --.

Column 49,
Line 62, "pmol" should be -- µmol --.

Column 50,
Line 32, "diner" should be dimer --.

Column 51,
Line 45, "(5x1 it)" should be -- (5x1 1t) --.
Line 54, "tiC" should read -- t1C --.

UNITED STATES PATENT AND TRADEMARK OFFICE
CERTIFICATE OF CORRECTION

PATENT NO.        : 5,808,023
APPLICATION NO. : 08/335046
DATED              : September 15, 1998
INVENTOR(S)       : Yogesh S. Sanghvi et al.

It is certified that error appears in the above-identified patent and that said Letters Patent is hereby corrected as shown below:

Column 54,
Line 59, "(50ACi/ml)" should be -- 50μCi/ml --.

Column 56,
Line 46, "oligonucleotide" should be -- Oligonucleotide -- beginning of a new sentence.

This certificate supersedes Certificate of Correction issued August 13, 2002.

Signed and Sealed this

Twenty-first Day of November, 2006

JON W. DUDAS
*Director of the United States Patent and Trademark Office*